United States Patent [19]
Boger

[11] Patent Number: 6,060,608
[45] Date of Patent: May 9, 2000

[54] ANALOGS OF CC-1065 AND THE DUOCARMYCINS

[75] Inventor: Dale L. Boger, La Jolla, Calif.

[73] Assignee: The Scripps Research Institute, La Jolla, Calif.

[21] Appl. No.: 09/194,467

[22] PCT Filed: May 30, 1997

[86] PCT No.: PCT/US97/09076

§ 371 Date: Sep. 7, 1999

§ 102(e) Date: Sep. 7, 1999

[87] PCT Pub. No.: WO97/45411

PCT Pub. Date: Dec. 4, 1997

Related U.S. Application Data

[60] Provisional application No. 60/018,860, May 31, 1996, and provisional application No. 60/023,346, Sep. 12, 1996.

[51] Int. Cl.[7] ..................... C07D 209/56; C07D 403/06; C07D 417/04; C07D 487/04

[52] U.S. Cl. ............................ 548/420; 548/181; 548/421

[58] Field of Search ..................................... 548/187, 420, 548/421

[56] References Cited

U.S. PATENT DOCUMENTS 5,258,383  11/1993  Nagamura et al. ..................... 514/253

*Primary Examiner*—Laura L. Stockton
*Attorney, Agent, or Firm*—Donald G. Lewis

[57] ABSTRACT

Analogs of antitumor antibiotics CC-1065 and the duocarmycins are synthesized which possess systematic and extensive modifications in the DNA binding subunits attached to a 1,2,9,9a-tetra-hydro-cyclo-propa[c]benz[e]indol-4-one (CBI) alkylation subunit. The analogs have potent cytotoxic activity and are efficacious antitumor compounds.

7 Claims, 35 Drawing Sheets

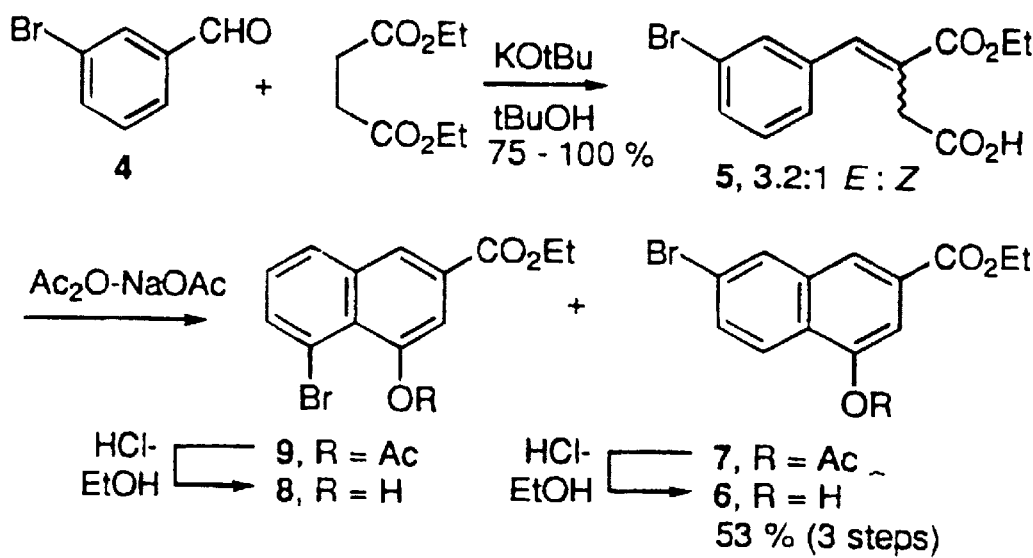
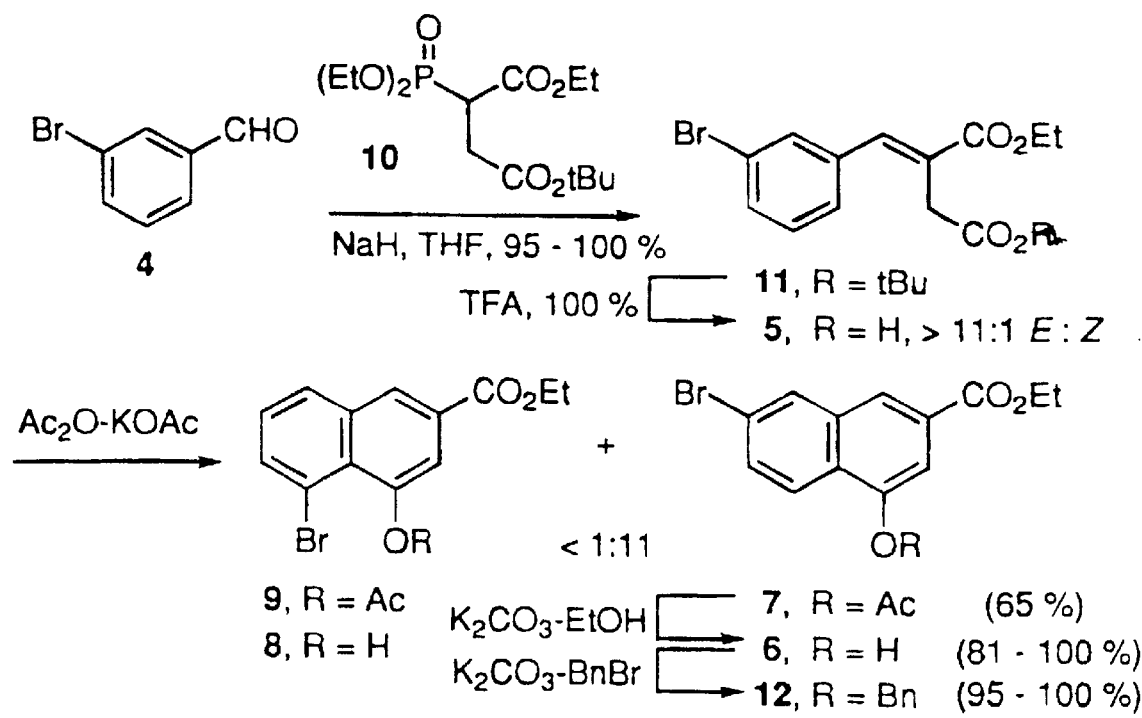
FIG. 2

| agent | IC$_{50}$(L1210) | agent | IC$_{50}$(L1210) | agent | IC$_{50}$(L1210) |
|---|---|---|---|---|---|
| Natural Enantiomers | | | | | |
| 25, (+)-CCBI | 2 μM | (+)-CBI | nd | (+)-MCBI | 5 μM |
| 26, (+)-N-BOC-CCBI | 20 nM | (+)-N-BOC-CBI | 80 nM | (+)-N-BOC-MCBI | 90 nM |
| 35, (+)-CCBI-TMI | 7 pM | (+)-CBI-TMI | 30 pM | (+)-N-MCBI-TMI | 8 pM |
| 37, (+)-CCBI-indole$_2$ | 7 pM | (+)-CBI-indole$_2$ | 10 pM | (+)-MCBI-indole$_2$ | 10 pM |
| 39, (+)-CCBI-CDPI$_1$ | 6 pM | (+)-CBI-CDPI$_1$ | 5 pM | (+)-MCBI-CDPI$_1$ | 6 pM |
| 41, (+)-CCBI-CDPI$_2$ | nd | (+)-CBI-CDPI$_2$ | 5 pM | (+)-MCBI-CDPI$_2$ | 6 pM |
| Unnatural Enantiomers | | | | | |
| 25, (−)-CCBI | 3 μM | (−)-CBI | 11 μM | (−)-MCBI | 30 μM |
| 26, (−)-N-BOC-CCBI | 80 nM | (−)-N-BOC-CBI | 900 nM | (−)-N-BOC-MCBI | 200 nM |
| 35, (−)-CCBI-TMI | 450 pM | (−)-CBI-TMI | 2000 pM | (−)-MCBI-TMI | 400 pM |
| 37, (−)-CCBI-indole$_2$ | 400 pM | (−)-CBI-indole$_2$ | 4000 pM | (−)-MCBI-indole$_2$ | 30 pM |
| 39, (−)-CCBI-CDPI$_1$ | 80 pM | (−)-CBI-CDPI$_1$ | 380 pM | (−)-MCBI-CDPI$_1$ | 10 pM |
| 41, (−)-CCBI-CDPI$_2$ | nd | (−)-CBI-CDPI$_2$ | 40 pM | (−)-MCBI-CDPI$_2$ | 10 pM |

FIG. 6

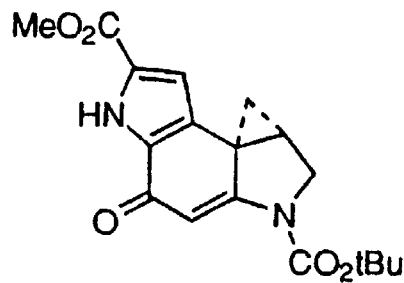
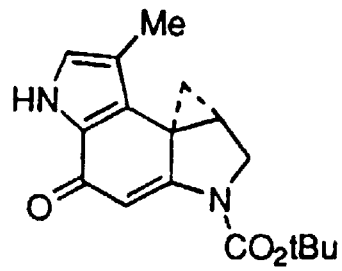
44, (+)-N-BOC-DSA    45, (+)-N-BOC-CPI
46, (+)-N-BOC-DA    47, (-)-N-BOC-CBQ    48, (+)-N-BOC-CI
|  | $k$ (s$^{-1}$, pH 3) | $t_{1/2}$ (pH 3) | IC$_{50}$ (L1210) |
|---|---|---|---|
| 44 | 1.08 x 10$^{-6}$ | 177 h | 6 nM |
| 41 | 1.45 x 10$^{-6}$ | 133 h | 80 nM |
| 45 | 5.26 x 10$^{-6}$ | 37 h | 330 nM |
| 46 | 1.75 x 10$^{-5}$ | 11 h | 1000 nM |
| 47 | 9.07 x 10$^{-5}$ | 2.1 h | 2000 nM |
| 48 | 1.98 x 10$^{-2}$ | 0.01 h | 18000 nM |
pH = 3
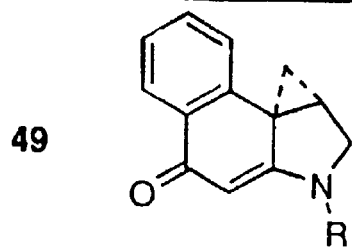
49
| R | $k$ (s$^{-1}$) | $t_{1/2}$ | IC$_{50}$ (L1210) | σ |
|---|---|---|---|---|
| SO$_2$Et | 0.5 x 10$^{-6}$ | 383 h | 24 nM | 0.72 |
| COEt | 2.0 x 10$^{-6}$ | 96 h | 110 nM | 0.48 |
| CO$_2$Me | 3.4 x 10$^{-6}$ | 57 h | 140 nM | 0.45 |
| CONHMe | 5.3 x 10$^{-6}$ | 36 h | 200 nM | 0.36 |
FIG. 9

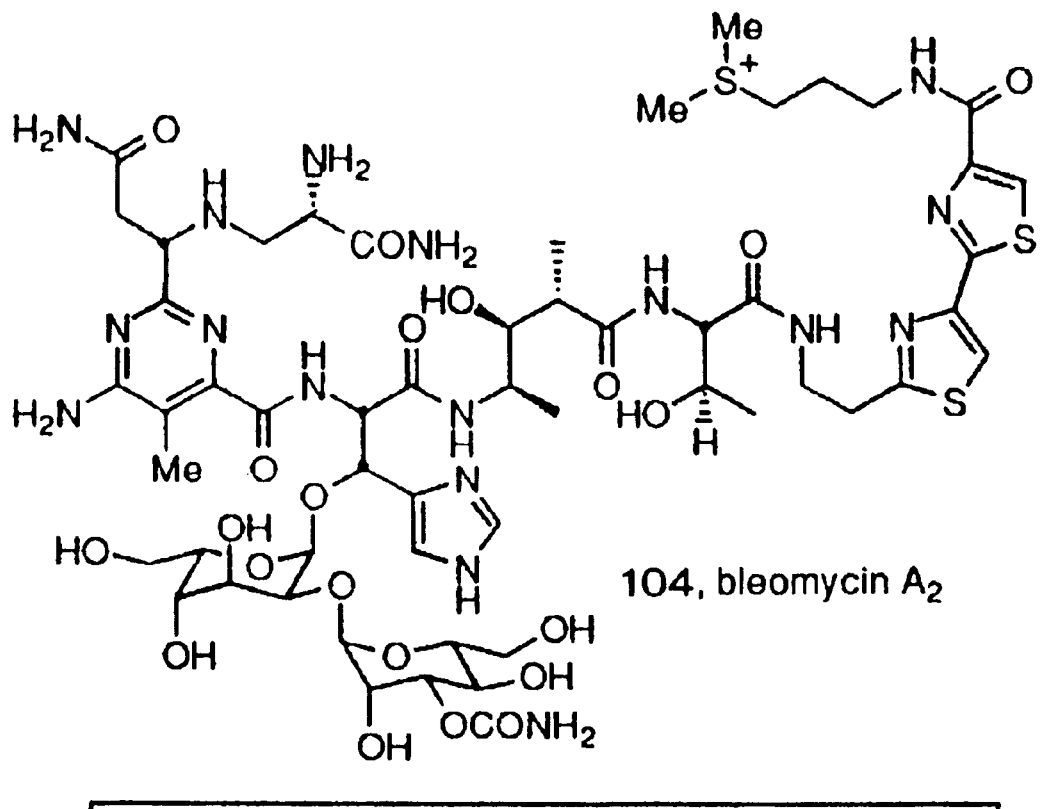
104, bleomycin A₂
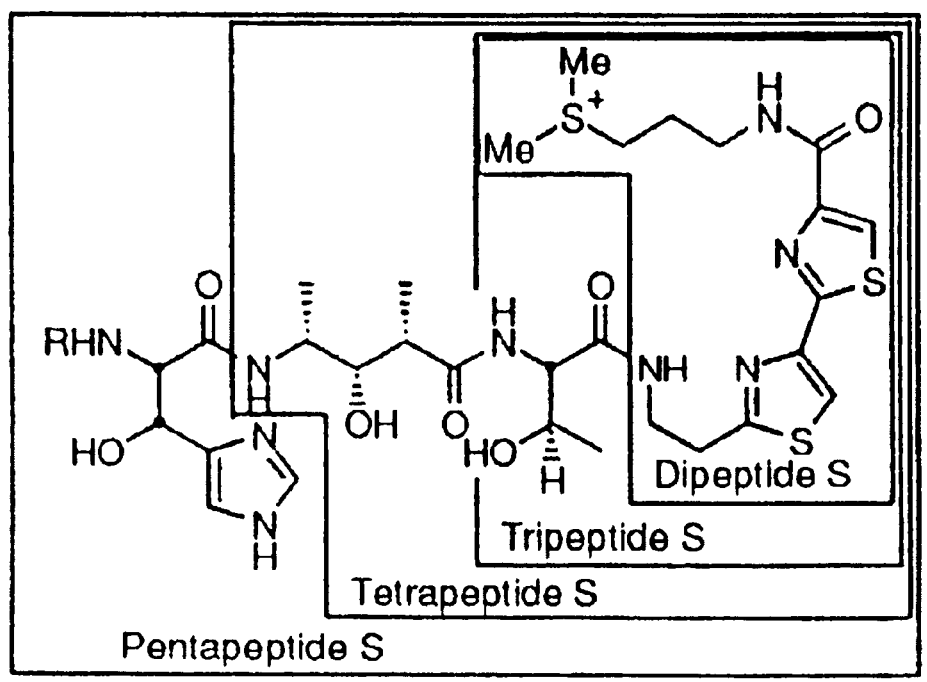
FIG. 15

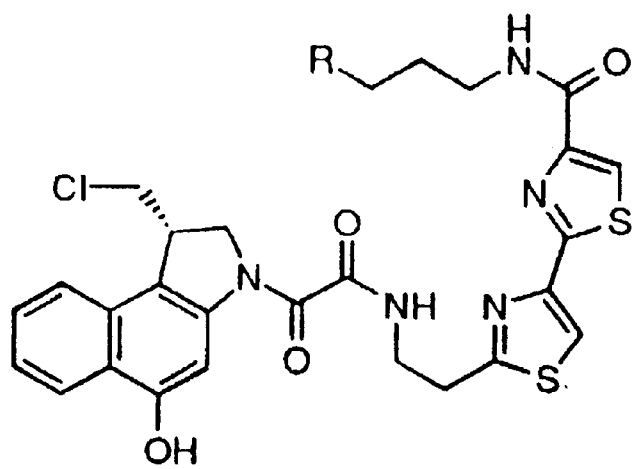
105, R = SMe
106, R = S(O)Me
107, R = +SMe₂
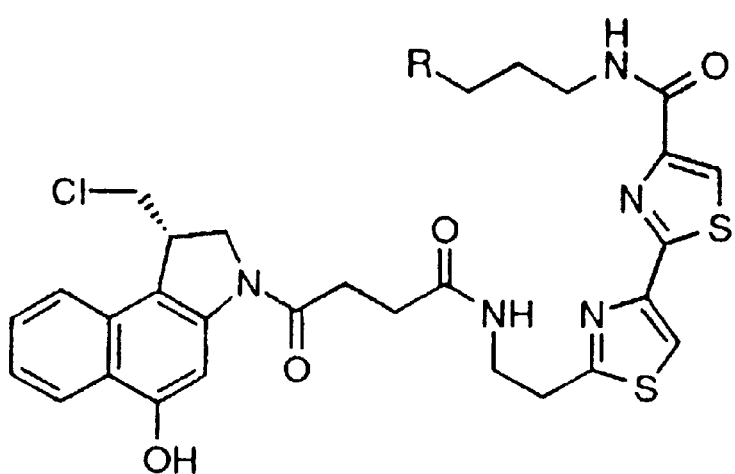
108, R = SMe
109, R = +SMe₂
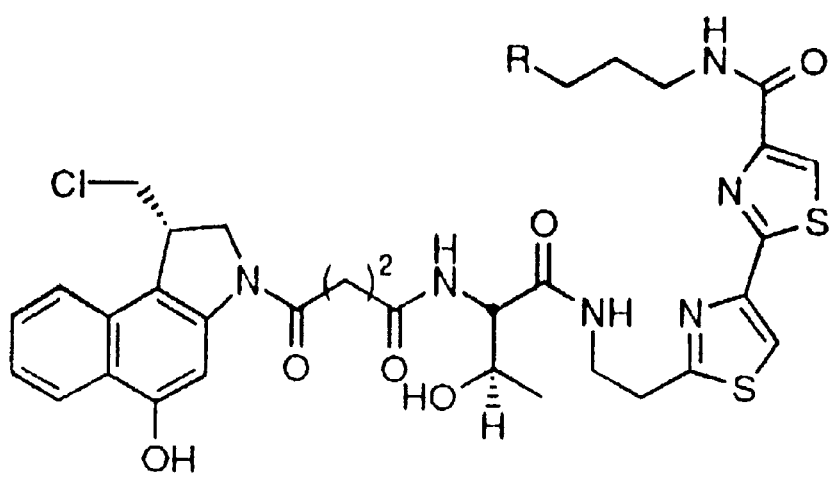
110, R = SMe
111, R = +SMe₂
FIG. 16

| Agent | Configuration | IC$_{50}$ (L1210, |
|---|---|---|
| (+)-1 | Natural | 0.02 |
| ent-(−)-1 | Unnatural | 0.02 |
| (+)-2 | Natural | 0.01 |
| ent-(−)-2 | Unnatural | 0.10 |
| (+)-3 | Natural | 0.5 |
| ent-(−)-3 | Unnatural | ≥22 |
| (1S)-105 | Natural | 500 |
| ent-(1R)-105 | Unnatural | 500 |
| (1S)-106 | Natural | >1500 |
| ent-(1R)-106 | Unnatural | >1500 |
| (1S)-107 | Natural | >1300 |
| ent-(1R)-107 | Unnatural | >1300 |
| (1S)-108 | Natural | 1000 |
| (1S)-109 | Natural | 2100 |
| (1S)-110 | Natural | 3100 |
| (1S)-111 | Natural | 7700 |
| (1S)-114 | Natural | 250 |
| ent-(1R)-114 | Unnatural | 600 |
| (1S)-115 | Natural | 6 |
| ent-(1R)-115 | Unnatural | 200 |
| (+)-116 | Natural | 5 |
| ent-(−)-116 | Unnatural | 200 |
| (+)-123 | Natural | 80 |
| ent-(−)-123 | Unnatural | 1000 |
| (+)-124 | Natural | 200 |
| (+)-125 | Natural | 140 |
| (+)-126 | Natural | 110 |
| (+)-127 | Natural | 25 |

FIG. 21

123, R = CO$_2$tBu
124, R = CONHMe
125, R = CO$_2$Me
126, R = COEt
127, R = SO$_2$Et

| Agent | (1) % Recovery ($\lambda_{max}$, A)[b] | (2) % Recovery ($\lambda_{max}$, A)[b] | Control[c] ($\lambda_{max}$, A)[b] |
|---|---|---|---|
| 105 | 95% (298 nm, 0.39) | 88% (297 nm, 0.36) | (297 nm, 0.41) |
| ent 105 | 100% (296 nm, 0.60) | 100% (296 nm, 0.61) | (297 nm, 0.55) |
| 106 | 100% (298 nm, 0.42) | 100% (298 nm, 0.39) | (299 nm, 0.33) |
| ent 106 | 100% (298 nm, 0.44) | 100% (298 nm, 0.42) | (297 nm, 0.38) |
| 108 | 100% (296 nm, 0.76) | 100% (297 nm, 0.77) | (297 nm, 0.68) |
| 109 | 63% (291 nm, 0.32) | nd | (294 nm, 0.51) |
| 110 | 90% (297 nm, 0.47) | 80% (298 nm, 0.41) | (298 nm, 0.52) |
| 111 | 72% (290 nm, 0.33) | nd | (295 nm, 0.46) |

[a]Incubation carried out at 37 °C, 48-72 h. Unreacted agent recovered by extraction or DNA precipitation, see text. [b]UV $\lambda_{max}$ and absorbance. [c]Control recovery without DNA following identical incubation conditions.

FIG. 25

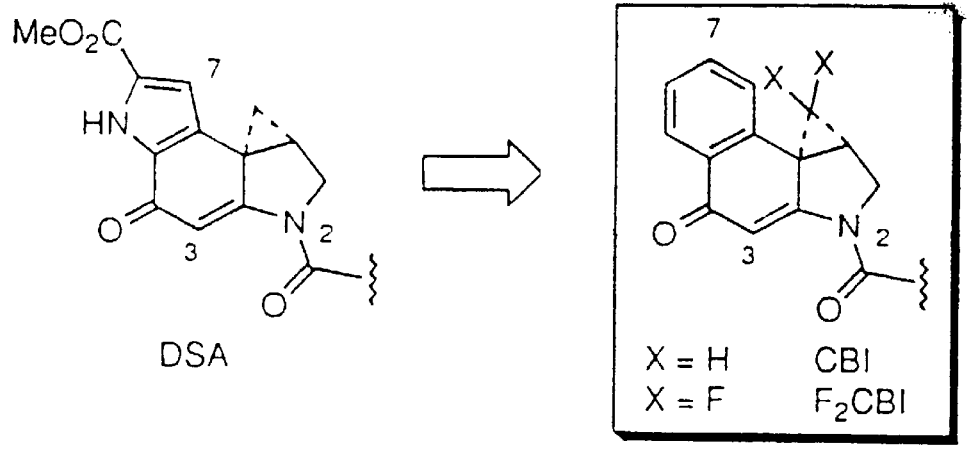

FIG. 26

| agent | $t_{1/2}$(h, pH 3) | $k$ (s$^{-1}$, pH3) | $t_{1/2}$(h, pH 7) | $k$ (s$^{-1}$, pH 7) |
|---|---|---|---|---|
| N-BOC-F$_2$CBI(219) | 0.26 | 7.05 × 10$^{-4}$ | 2.3 | 8.27 × 10$^{-5}$ |
| N-BOC-CBI | 133 | 1.45 × 10$^{-6}$ | stable | stable |
| F$_2$CBI(218) | 4.2 | 4.54 × 10$^{-5}$ | 422 | 4.56 × 10$^{-7}$ |
| CBI | 930 | 2.07 × 10$^{-7}$ | stable | stable |
| N-acetyl-F$_2$CBI (217) | 0.27 | 7.25 × 10$^{-4}$ | 2.0 | 9.80 × 10$^{-5}$ |

FIG. 32

| agent | IC$_{50}$(L1210) | agent | IC$_{50}$(L1210) |
|---|---|---|---|
| (±) 217 | 60 µM | (+)-N-acetyl-CBI | 110 nM |
| (±)-218 | 140 µM | (+)-CBI | nd |
| (±)-219 | 110 µM | (+)-N-BOC-CBI | 80 nM |
| (±)-233 | 36 nM | (+)-CBI-TMI | 30 pM |

FIG. 34

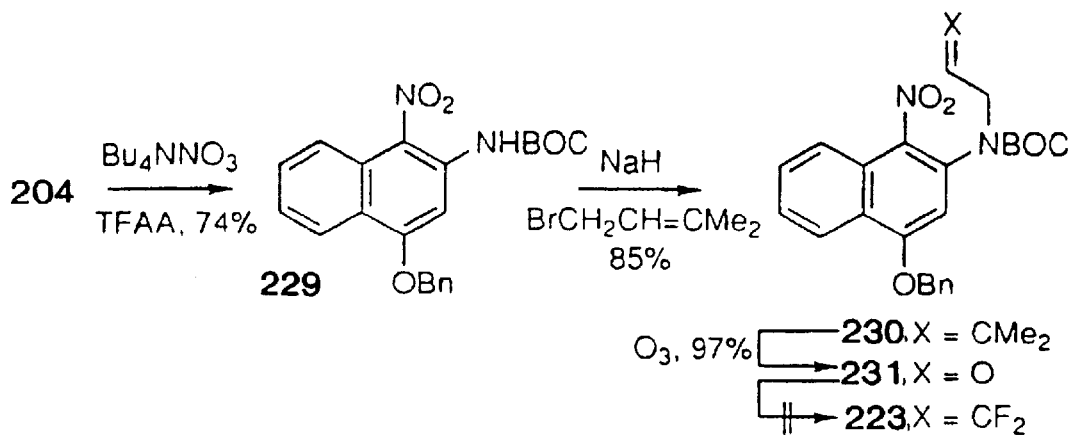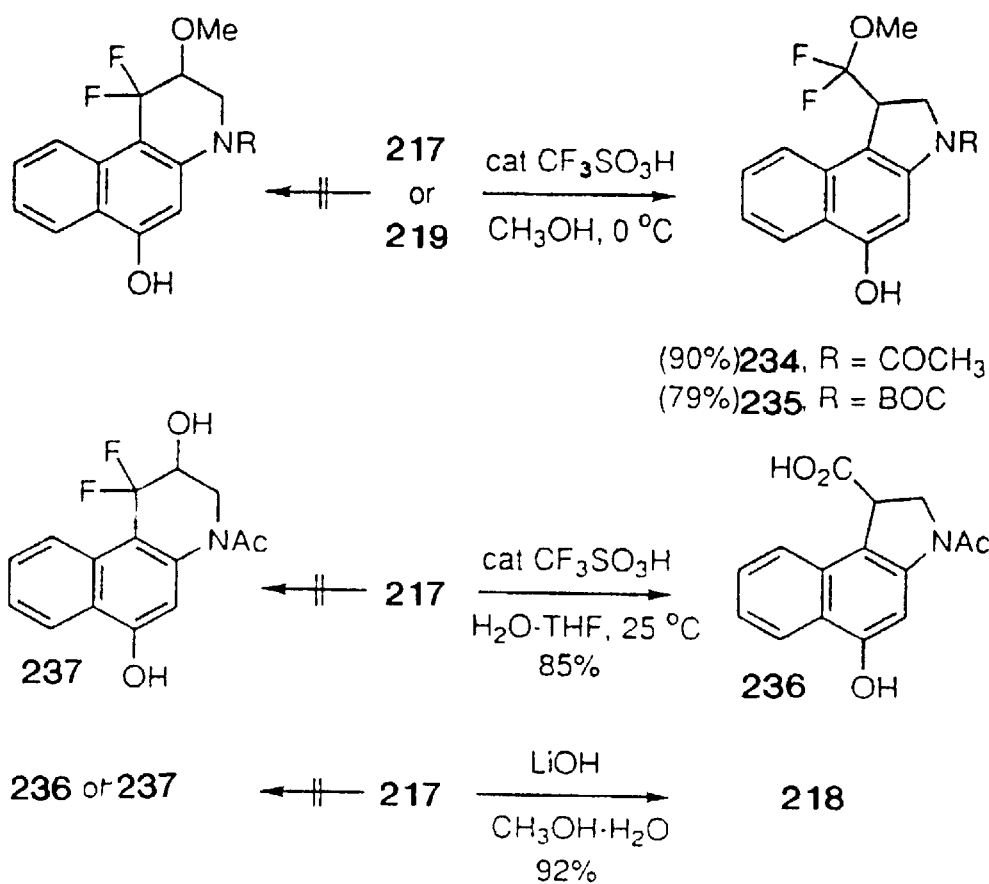
FIG.33

| Agent | IC$_{50}$ (pM, L1210) | Rel. DNA Alkyl. Efficiency | Agent | IC$_{50}$ (pM, L1210) |
|---|---|---|---|---|
| natural enantiomers | | | unnatural enantiomers | |
| (+)-1 | 10 | 1.0 | (-)-1 | 100 |
| (+)-305 | 10-12 | 1.0 | (-)-305 | 300 |
| (+)-306 | 25 | 0.2 | (-)-306 | 1300 |
| (+)-307 | 60 | 0.1 | (-)-307 | 1800 |
| (+)-304 | 65 | 0.05 | (-)-304 | 1700 | ns of CC-1065 AND THE
DUOCARMYCINS

This application is a 371 of PCT/US97/09076 filed May 30, 1997 which claims the benefit of U.S. Provisional Application No. 60/018,860 filed May 31, 1996 and U.S. Provisional Application No. 60/023,346 filed Sep. 12, 1996.

DESCRIPTION

1. Field of Invention

The invention relates to antitumor antibiotics. More particularly, the invention relates to analogs of CC-1065 and the duocarmycins having antitumor antibiotic activity.

2. Background (+)-CC-1065 (1) and the duocarmycins represent the initial members of a class of exceptionally potent antitumor antibiotics. Members of this class of antitumor antibiotic derive their biological effects through the reversible, stereoelectronically-controlled sequence selective alkylation of duplex DNA. (H. Sugiyama, et al., *Tetrahedron Lett.* 1990, 31, 7197; C. H. Lin, et al., *J. Am. Chem. Soc.* 1992, 114, 10658; H. Sugiyama, et al., *Tetrahedron Lett.* 1993, 34, 2179; K. Yamamoto, et al., *Biochemistry* 1993, 32, 1059; A. Asai, et al., *J. Am. Chem. Soc.* 1994, 116, 4171; and D. L. Boger, et al., *Tetrahedron* 1991, 47, 2661.) (+)-CC-1065 (1) was first disclosed in 1981 by L. J. Hanka, et al. (*J. Am. Chem. Soc.* 1981, 103, 7629.) The duocarmycins were first disclosed in 1988 and 1990. (Takahashi, et al. *J. Antibiot.* 1988, 41, 1915; T. Yasuzawa, et al., *Chem. Pharm. Bull.* 1988, 36, 3728; M. Ichimura, et al., *J. Antibiot.* 1988, 41, 1285; M. Ichimura, et al., *J. Antibiot.* 1990, 43, 1037; M. H. Ichimura, et al., *J. Antibiot.* 1991, 44, 1045; K. Ohba, et al., *J. Antibiot.* 1988, 41, 1515; and S. Ishii, *J. Antibiot.* 1989, 42, 1713.)

Subsequent to their disclosure, extensive efforts have been devoted to establish their duplex DNA alkylation selectivity and its structural origin. (D. L. Boger, *Acc. Chem. Res.* 1995, 28, 20; D. L. Boger, *Proc. Natl. Sci. U.S.A.* in press; D. L. Boger, *Chemtracts: Org. Chem.* 1991, 4, 329; D. L. Boger, In *Proceed. R. A. Welch Found. Conf. on Chem. Res., XXXV. Chem. at the Frontiers of Medicine* 1991, 35, 137; D. L. Boger, In *Advances in Heterocyclic Natural Products Synthesis*, Vol. 2, Pearson, W. H. Ed.; JAI Press: Greenwich, Conn., 1992, 1–188; D. L. Boger, *Pure Appl. Chem.* 1993, 65, 1123; D. L. Boger, *Pure Appl. Chem.* 1994, 66, 837; R. S. Coleman, In *Studies in Nat. Prod. Chem.*, Vol 3, Rahman, A.-u.-, Ed.; Elsevier: Amsterdam, 1989, 301; and D. L. Boger, In *Heterocycles in Bioorganic Chemistry*; J. Bergman , H. C. van der Plas, and M. Simonyl, Eds; Royal Society of Chemistry: Cambridge, 1991, 103.) Progress has also been made with respect to characterizing the link between DNA alkylation and the ensuing biological properties. (D. L. Boger, et al., *Bioorg. Med. Chem. Lett.* 1994, 4, 631.) Extensive efforts have also been devoted to define the fundamental principles underlying the relationships between structure, chemical reactivity, and biological properties. (W. Wierenga, et al., *Adv. Enzyme Regul.* 1986, 25, 141; M. A. Warpehoski, et al., *J. Med. Chem.* 1988, 31, 590; D. L. Boger, et al., *J. Am. Chem. Soc.* 1993, 115, 9025; D. L. Boger, et al., *J. Am. Chem. Soc.* 1992, 114, 10056; H. Muratake, et al., *Tetrahedron Lett.* 1994, 35, 2573; Y. Fukuda, et al., *Tetrahedron* 1994, 50, 2793; Y. Fukuda, et al., *Tetrahedron* 1994, 50, 2809; Y. Fukuda, et al., *Bioorg. Med. Chem. Lett.* 1992, 2, 755; Y. Fukuda, et al., *Tetrahedron Lett.* 1990, 31, 6699; W. Wierenga, *J. Am. Chem. Soc.* 1981, 103, 5621; P. Magnus, et al., *J. Am. Chem. Soc.* 1987, 109, 2706; G. A. Kraus, et al., *J. Org. Chem.* 1985, 50, 283; D. L. Boger, et al., *J. Am. Chem. Soc.* 1988, 110, 1321, 4796; R. E. Bolton, et al., *J. Chem. Soc., Perkin Trans.* 1 1988, 2491; R. J. Sundberg, et al., *J. Org. Chem.* 1988, 53, 5097; R. J. Sundberg, et al., *J. Org. Chem.* 1991, 56, 3048; V. P. Martin, *Helv. Chim. Acta* 1989, 72, 1554; M. Toyota, et al., *J. Chem. Soc., Perkin Trans.* 1 1992, 547; and L. F. Tietze, et al., *J. Org. Chem.* 1994, 59, 192.) The relationships between structure, chemical reactivity, and biological properties of CI-based analogs have also been characterized. (D. L. Boger, et al., *Proc. Natl. Acad. Sci. U.S.A.* 1991, 88, 1431; D. L. Boger, et al., *J. Am. Chem. Soc.* 1991, 113, 3980; D. L. Boger, et al., *J. Org. Chem.* 1989, 54, 1238; D. L. Boger, et al., *J. Am. Chem. Soc.* 1990, 112, 5230; K. J. Drost, et al., *J. Org. Chem.* 1989, 54, 5985; J. H. Tidwell, et al., *J. Org. Chem.* 1992, 57, 6380; .J. Sundberg, et al., *Tetrahedron Lett.* 1986, 27, 2687; Y. Wang, et al., *Heterocycles* 1993, 36, 1399; Y. Wang, et al., *J. Med. Chem.* 1993, 36, 4172; L. F. Tietze, et al., *Chem. Ber.* 1993, 126, 2733; and T. Sakamoto, et al., *J. Chem. Soc., Perkin Trans.* 1 1993, 1941.) The relationships between structure, chemical reactivity, and biological properties of $C_2BI$-based analogs have also been characterized. (D. L. Boger, et al., *J. Am. Chem. Soc.* 1992, 114, 9318; and D. L. Boger, et al., *Bioorg. Med. Chem.* 1993, 1, 27.) The relationships between structure, chemical reactivity, and biological properties of CBQ-based analogs have also been characterized. (D. L. Boger, et al., *J. Am. Chem. Soc.* 1994, 116, 6461; and D. L. Boger, et al., *J. Am. Chem. Soc.* 1994, 116, 11335.) F. Mohamadi et al. have characterized the relationships between structure, chemical reactivity, and biological properties of CFI-based analogs (*J. Med. Chem.* 1994, 37, 232.) A p-quinonemethide analog was characterized by D. L. Boger, et al. (*J. Org. Chem.* 1994, 59, 4943.)

Concurrent with the above structure/function studies, substantial efforts have been devoted to developing potential clinical candidates based on the natural product structures having enhanced in vivo efficacy. (D. L. Boger, et al., *J. Org. Chem.* 1984, 49, 2240; M. A. Warephoski, M. A. *Tetrahedron Lett.* 1986, 27, 4103; Li, L. H.; *Invest. New Drugs* 1991, 9, 137; B. K. Bhuyan, et al., *Cancer Res.* 1992, 52, 5687; B. K. Bhuyan, et al., *Cancer Res.* 1993, 53, 1354; L. H. Li, et al., *Cancer Res.* 1992, 52, 4904; M. A. Mitchell, et al., *J. Am. Chem. Soc.* 1991, 113, 8994. Lee, C.-S.; Gibson, N. W. *Cancer Res.* 1991, 51, 6586. Lee, C.-S.; Gibson, N. W. *Biochemistry* 1993, 32, 9108; Wierenga, W. *Drugs Fut.* 1991, 16, 741; K. Gomi, et al., *Jpn. J. Cancer Res.* 1992, 83, 113. Okamoto, A.; Okabe, M.; Gomi, K. *Jpn. J. Cancer Res.* 1993, 84, 93; E. Kobayashi, et al., *Cancer Res.* 1994, 54, 2404; and H. Ogasawara, *Jpn. J. Cancer Res.* 1994, 85, 418.) A Phase I clinical trial one one drug candidate in this class is described by G. F. Fleming, et al., (*J. Natl. Cancer Inst.* 1994, 86, 368.) Efforts have also focused on the development of analogs having decreased delayed toxicity as compared to the natural form of (+)-CC-1065. (J. P. McGovren, et al., *Cancer Res.* 1993, 53, 5690.) Importantly, this unusual property has not been observed with ent-(−)-CC-1065, although it is equally cytotoxic, and is not observed with the naturally-derived duocarmycins as well as simplified analogs of the natural products.

The first preparation and examination of agents containing the 1,2,9,9a-tetrahydrocyclopropa[c]benz[e]indol-4-one (CBI) alkylation subunit were described in connection with efforts to evaluate CC-1065 and duocarmycin analogs bearing deep-seated structural alterations in the alkylation subunit. (D. L. Boger, et al., *J. Am. Chem. Soc.* 1989, 111, 6461; and D. L. Boger, et al., *J. Org. Chem.* 1990, 55, 5823.) These agents were employed as tools to identify the structural features associated with their sequence selective alkylation of duplex DNA and to define the fundamental relationships between structure, chemical or functional reactivity and biological properties.

Prior to the present invention, it had been assumed that the unique alkylating activity of the naturally occurring CPI subunit of CC-1065 would be degraded if this portion of the molecule were structurally altered. (L. H. Hurley, et al., *Science* 1984, 226, 843; V. L. Reynolds, et al., *Biochemistry* 1985, 24, 6228.

L. H. Hurley, et al., *Biochemistry* 1988, 27, 3886; L. H. Hurley, et al., *J. Am. Chem. Soc.* 1990, 112, 4633; M. A. Warpehoski, et al., *J. Biochemistry* 1992, 31, 2502; D. L. Boger, et al., *Bioorg. Med. Chem.* 1994, 2, 115; D. L. Boger, et al., *J. Am. Chem. Soc.* 1990, 112, 4623; M. A. Warpehoski, et al., In *Advances in DNA Sequence Specific Agents*; Hurley, L. H., Ed.; JAI Press: Greenwich, Conn., 1992, Vol 1, 217; M. A. Warpehoski, *Drugs Fut.* 1991, 16, 131; M. A. Warpehoski, et al., in *Molecular Basis of Specificity in Nucleic Acid-Drug Interactions*; B. Pullman and J. Jortner, Eds.; Kluwer: Netherlands; 1990, 531; M. A. Warpehoski, et al., *Chem. Res. Toxicol.* 1988, 1, 315; Hurley, L. H.; In *Molecular Aspects of Anticancer Drug-DNA Interactions*; Neidle, S., Waring, M., Eds.; CRC Press: Ann Arbor, Mich. 1993, Vol 1, 89; and L. H. Hurley, et al., *Acc. Chem. Res.* 1986, 19, 230.) The above assumption is disclosed herein to be inaccurate. Furthermore, the natural enantiomers of the CBI-based analogs of (+)-CC-1065, have been shown to be approximately four times more stable chemically and approximately four times more potent biologically as compared to the corresponding agents incorporating the natural CPI alkylation subunit of CC-1065. (D. L. Boger, et al., *Tetrahedron Lett.* 1990, 31, 793; D. L. Boger, et al., *J. Org. Chem.* 1992, 57, 2873; and D. L. Boger, et al., *J. Org. Chem.* 1995, 60, 0000.) The CBI analogs are also considerably more synthetically accessible as compared to the naturally occurring CPI compounds. (+)-CBI-indole$_2$ exhibits cytotoxic potency comparable to that of the (+)-CC-1065 and greater (4x) than that of the potential clinical candidate (+)-CPI-indole$_2$ (U71,184) introduced by Upjohn. (+)-CBI-indole$_2$ also exhibits potent and efficacious In vivo antitumor activity. (D. L. Boger, et al., *Bioorg. Med. Chem. Lett.* 1991, 1, 115.) (+)-CBI-indole$_2$ (27) was the first efficacious antitumor activity by a CC-1065 analog possessing a structurally altered and simplified DNA alkylation subunit. Moreover, the agent further lacked the delayed fatal toxicity characteristic of (+)-CC-1065.

The natural enantiomers of the CBI-based analogs have been shown to alkylate DNA with an unaltered sequence selectivity as compared to the corresponding CPI analog. (D. L. Boger, et al., *J. Am. Chem. Soc.* 1994, 116, 7996; and P. A. Aristoff, et al., *J. Med. Chem.* 1993, 36, 1956.) Furthermore, the DNA alkylation of CBI-based analogs occurs at an enhanced rate as compared to the corresponding CPI analogs (D. L. Boger, et al., *J. Am. Chem. Soc.* 1991, 113, 2779) and with a greater efficiency than the corresponding CPI analog. (D. L. Boger, et al., *J. Am. Chem. Soc.* 1992, 114, 5487).

Refined models of the DNA alkylation reactions of the duocarmycins have been developed which accommodate the reversed and offset AT-rich adenine N3 DNA alkylation selectivity of the enantiomeric agents and their structural analogs. (D. L. Boger, et al., *J. Org. Chem.* 1990, 55, 4499; D. L. Boger, et al., *J. Am. Chem. Soc.* 1990, 112, 8961; D. L. Boger, et al., *J. Am. Chem. Soc.* 1991, 113, 6645; D. L. Boger, et al., *J. Am. Chem. Soc.* 1993, 115, 9872; D. L. Boger, et al., *Bioorg. Med. Chem. Lett.* 1992, 2, 759; and D. L. Boger, et al., *J. Am. Chem. Soc.* 1994, 116, 1635.) A similar refined model of the DNA alkylation reactions of CC-1065 have been developed which also accommodate the reversed and offset AT-rich adenine N3 DNA alkylation selectivity of the enantiomeric agents and their structural analogs. (D. L. Boger, et al., *Bioorg. Med. Chem.* 1994, 2, 115; and D. L. Boger, et al., *J. Am. Chem. Soc.* 1990, 112, 4623.) These models teach that the diastereomeric adducts derived from the unnatural enantiomers suffer a significant destabilizing steric interaction between the CPI C7 center (CH$_3$) or the CBI C8 center with the base adjacent to the alkylated adenine which is not present with the natural enantiomer adducts. Moreover, the distinguishing features of the natural and unnatural enantiomers diminish or disappear as the inherent steric bulk surrounding this center is reduced or removed. Because of the unnatural enantiomer sensitivity to destabilizing steric interactions surrounding the CPI C7 or CBI C8 center, the unnatural enantiomers of the CBI-based analogs are particularly more effective than the corresponding CPI analog displaying an even more enhanced relative rate and efficiency of DNA alkylation.

What is needed is an alternative alkylating agent having an altered reactivity as compared to CBI which may be incorporated into analogs of CC-10665 and the duocarmycins.

SUMMARY OF THE INVENTION

A first aspect of the invention is directed to DNA alkylating agents represented by the following structure:

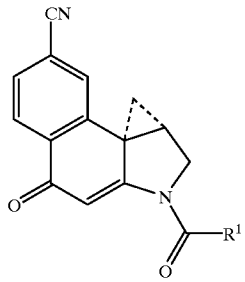

In the above structure $R_1$ is selected from the group consisting of alkyl (C1–C6) and a radical represented by the following structure:

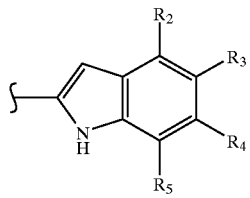

In a first embodiment of the above structure $R_2$ and $R_3$, together with the carbon atoms of the depicted vinylene group, form a group W that is an N-substituted pyrrolidine ring containing the vinylene group with the proviso that $R_4$ and $R_5$ are hydrogen. More particularly, the N-substituted pyrrolidine ring may be represented by the following structure:

wherein $R_2$ is C-linked and $R_3$ is N-linked to form the depicted pyroline ring and $R_6$ is selected from the group consisting of $NH_2$ and the compound represented by the following structure:

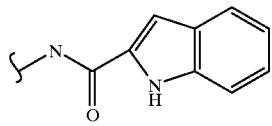

In a second embodiment, $R_2$ is hydrogen and $R_3$ is an N-substituted subgroup represented by the following compound:

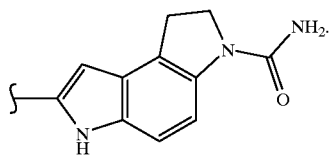

with the proviso that $R_4$ and $R_5$ are hydrogen.

In a third embodiment, $R_2$ is hydrogen; $R_3$ is selected from the group consisting of hydrogen and $OCH_3$; $R_4$ is selected from the group consisting of hydrogen and $OCH_3$; and $R_5$ is selected from the group consisting of hydrogen and $OCH_3$.

A second aspect of the invention is directed to DNA alkylating agents represented by the following structure:

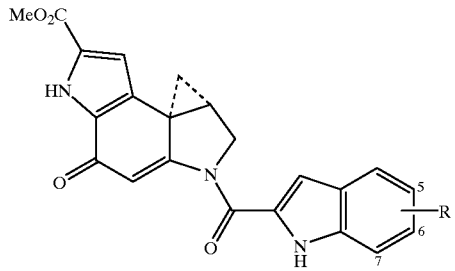

wherein R is selected from the group consisting of H and —OMe.

A third aspect of the invention is directed to DNA alkylating agents represented by the following structure:

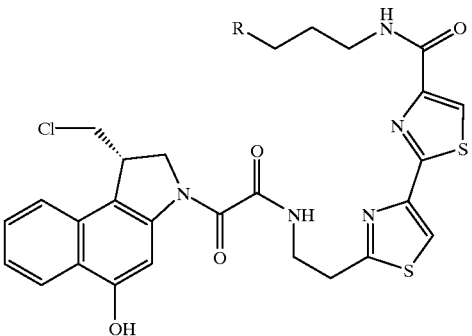

wherein R is selected from the group consisting of —SMe, —S(O)Me, and —$^+$SMe$_2$.

A fourth aspect of the invention is directed to DNA alkylating agents represented by the following structure:

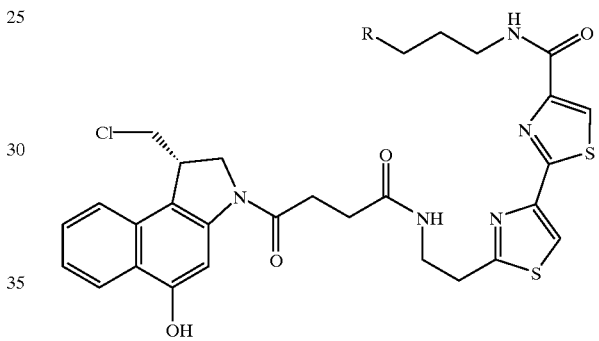

wherein R is selected from the group consisting of —SMe and —$^+$Sme$_2$.

A fifth aspect of the invention is directed to DNA alkylating agents represented by the following structure:

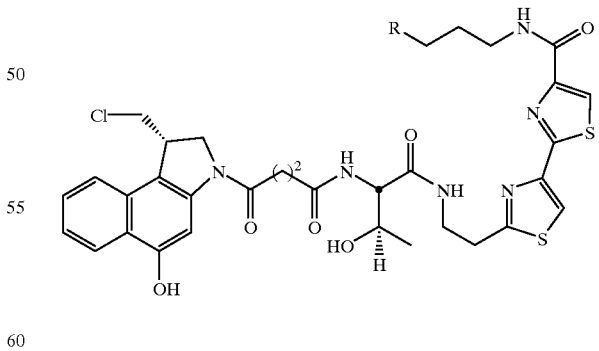

wherein R is selected from the group consisting of —SMe and —$^+$Sme$_2$.

A sixth aspect of the invention is directed to DNA alkylating agents represented by the following structure:

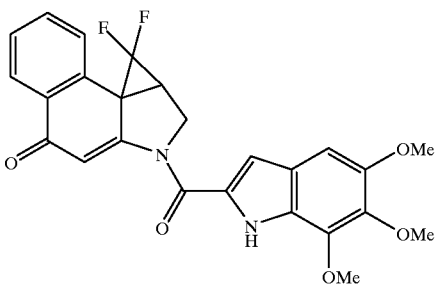

A seventh aspect of the invention is directed to the process of alkylating DNA with each of the above indicated DNA alkylating agents.

BRIEF DESCRIPTION OF THE DRAWINGS

FIG. 2 illustrates the synthesis of intermediate 6 (top scheme) and intermediate 12 (bottom scheme).

FIG. 6 shows a table of cytotoxic activity comparing CCBI-based agents alongside corresponding CBI and MCBI agents.

FIG. 9 illustrates comparisons made on three presently available agents which follow trends of 44–49.

FIG. 15 illustrates the bleomycins, a family of clinically effective glycopeptide antitumor antibiotics of which bleomycin A$_2$ (4) is the major constituent).

FIG. 16 illustrates a series of hybrid agents 105–111 of CC-1065/duocarmycins and the bleomycins which incorporate the CBI analog of the DNA alkylation subunits of the former natural products linked to the C-terminus di- and tripeptide S DNA binding domain of bleomycin A$_2$.

FIG. 21 summarizes the L1210 cytotoxic activity of the agents 105–111, the comparison samples 114–116 of CBI acylated with the linkers only, and a representative range of additional comparison agents including the natural products 1–3.

FIG. 25 shows a table of agents outlining calf thymus DNA alkylation and recovery.

FIG. 26 illustrates the 9,9-difluoro-1,2,9,9a-tetrahydrocyclopropa[c]benzo[e]indol-4-one ($F_2CBI$), a difluoro substituted cyclopropane analog of the alkylation subunits of 1–3 which represents the first such analog containing substitution or functionalization of the reactive center in the natural products.

FIG. 32 illustrates solvolysis reactivity of selected agents.

FIG. 33 illustrates nucleophilic addition under basic conditions to provide 218.

FIG. 34 illustrates in vitro cytotoxic activity of selected agents.

DETAILED DESCRIPTION

Figure 1:
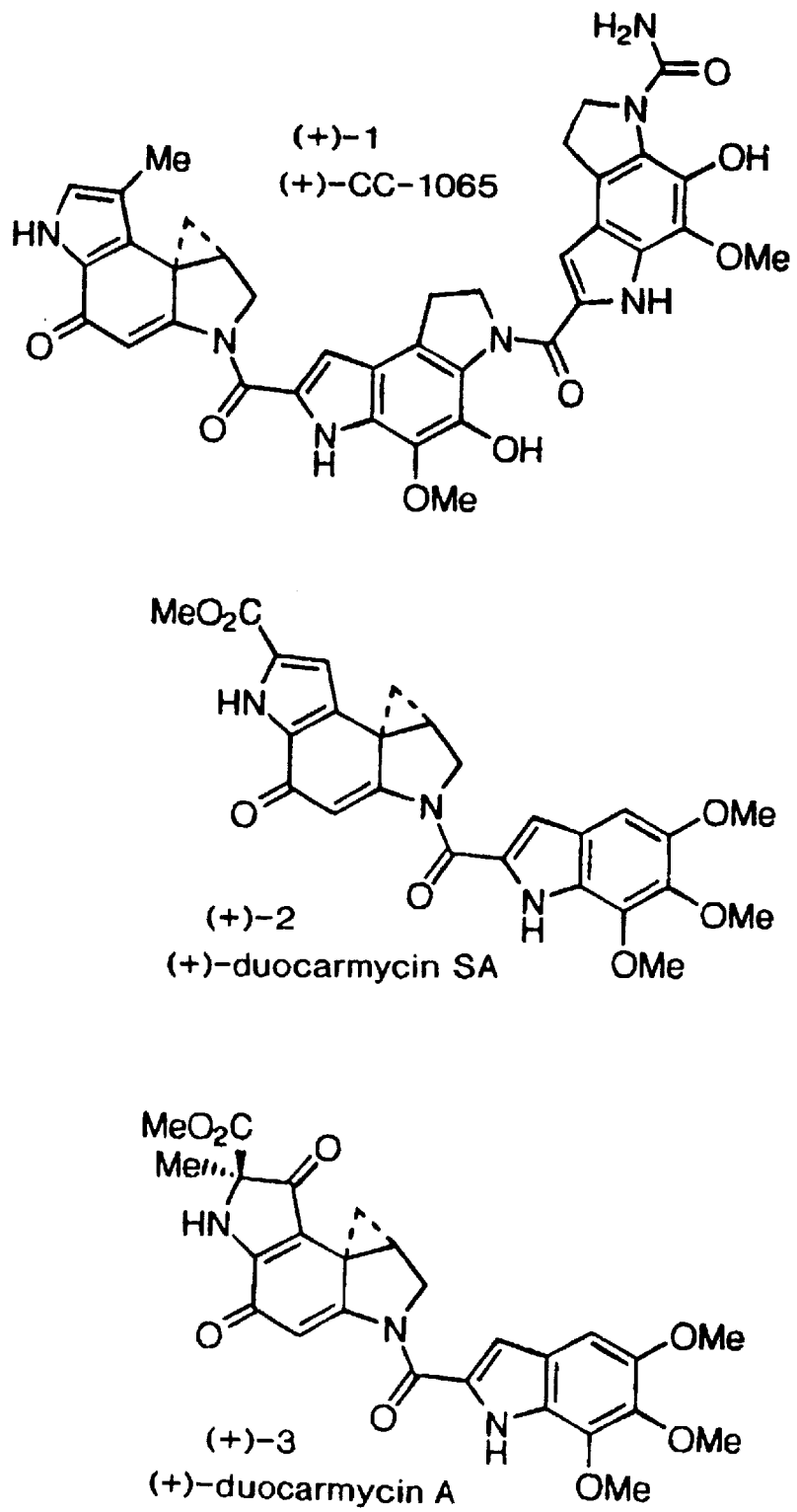
FIG. 1 illustrates the structures of (+)CC-1065 (1) and the duocarmycins 2–3.

The invention relates to analogs of antitumor antibiotics CC-1065 and the duocarmycins. The analogs are synthesized and possess systematic and extensive modifications in the DNA binding subunits attached to a 1,2,9,9a-tetra-hydrocyclo-propa[c]benz[e]indol-4-one (CBI) alkylation subunit. The analogs have potent cytotoxic activity and are efficacious antitumor compounds. One embodiment of the invention relates to the synthesis of substituted CCBI derivatives: 7-cyano-1,2,9,9a-tetra-hydrocyclo-propa[c]benz[e]-indol-4-one (CCBI), bearing a C7 cyano substituent para to the C4 carbonyl. A second embodiment of the invention comprises the synthesis of hybrid agents containing the C-terminus DNA binding domain of bleomycin linked to an analog of the CC-1065/duocarmycin DNA alkylation subunit. A third embodiment of the invention relates to the synthesis of cluorocyclopropane analogs of the duocarmycins incorporating the 9,9-difluoro-1,2,9,9a-tetrahydrrocycloprop[c]benz[e]indol4-one ($F_2$CBI) alkylation subunit. A fourth embodiment of the invention comprises the synthesis of Duocarmycin SA methoxy substituted analogs.

EXAMPLE 1

Synthesis of CCBI derivatives, 7-cyano-1,2,9,9a-tetra-hydrocyclo-propa[c]benz[e]-indol-4-one (CCBI)

In this example, the synthesis of 7-cyano-1,2,9,9a-tetrahydrocyclopropa[c]benz[e]indol-4-one (CCBI), a substituted CBI derivative bearing a C7 cyano group is described. The CCBI alkylation subunit was prepared by a modified Stobbe condensation/Friedel-Crafts acylation for generation of the appropriately functionalized naphthalene precursors followed by 5-exo-trig aryl radical-alkene cyclization for synthesis of the 1,2-dihydro-3H-benz[e] indole skeleton and final Ar-3' alkylation for introduction of the activated cyclopropane. The most concise approach provided the CCBI subunit and its immediate precursor in 14–15 steps in superb overall conversions (15–20%). Resolution of an immediate CCBI precursor and its incorporation into both enantiomers of 34–39, analogs of CC-1065 and the duocarmycins, are detailed infra. A study of the solvolysis reactivity and regioselectivity of N-BOC-CCBI (25) revealed that introduction of the C7 nitrile slowed the rate of solvolysis but only to a surprisingly small extent. Classical Hammett quantitation of the effect provided a remarkably small p (−0.3) indicating an exceptionally small C7 substituent electronic effect on functional reactivity. Additional kinetic studies of acid-catalyzed nucleophilic addition proved inconsistent with C4 carbonyl protonation as the slow and rate determining step but consistent with a mechanism in which protonation is rapid and reversible followed by slow and rate determining nucleophilic addition to the cyclopropane requiring both the presence and assistance of a nucleophile ($S_N2$ mechanism). No doubt this contributes to the DNA alkylation selectivity of this class of agents and suggests that the positioning of an accessible nucleophile (adenine N3) and not C4 carbonyl protonation is the rate determining step controlling the sequence selectivity of the DNA alkylation reaction. This small electronic effect on the solvolysis rate had no impact on the solvolysis regioselectivity and stereoelectronically-controlled nucleophilic addition to the least substituted carbon of the activated cyclopropane was observed exclusively. Consistent with past studies, a direct relationship between solvolysis stability and cytotoxic potency was observed with the CCBI-derived agents providing the most potent analogs in the CBI series and these observations were related to the predictable Hammett substituent effects. For the natural enantiomers, this unusually small electronic effect on functional reactivity had no perceptible effect on their DNA alkylation selectivity. Similar effects of the C7 cyano substituent on the unnatural enantiomers were observed and they proved to be 4–10× more effective than the corresponding CBI-based unnatural enantiomers and 4–70× less potent than the CCBI natural enantiomers.

Synthesis of CCBI (26) and N-BOC-CCBI (25)

Stobbe condensation of 3-bromobenzaldehyde (4) with diethyl succinate (1.5 equiv) affected by treatment with t-BuOK (1.1 equiv, t-BuOH, reflux, 2 h, 75–100%) provided a 3.2:1 mixture of the half esters 5 in excellent conversion (FIG. 2). Subjection of this mixture of 5 to Friedel-Crafts acylation (1–1.1 equiv of NaOAc, $Ac_2O$, reflux, 6 h) provided a mixture of 6, its O-acylation product 7 and significant amounts of the isomeric products 8 and 9. The best conversions were observed when the Friedel-Crafts acylation was conducted under moderately dilute reaction conditions (0.1 M versus 0.5 M). Subsequent ethanolysis (3M HCl—EtOH) of the resulting mixture served to hydrolyze the O-acetates 7 and 9 providing a 7:1 mixture of 6 and its isomer 8. Both 6 and 8 were readily separated by chromatography or more conveniently by simple recrystallization of the mixture. Although this procedure has provided 6 in conversions as high as 53% overall yield for the three steps, it generally provided the material in lower conversions of 20–30%. This diminished conversion may be attributed to the mixture of E- and Z-5 taken into the Friedel-Crafts acylation reaction and the vigorous reaction conditions and time required to affect the Z to E isomerization for productive cyclization.

This was improved significantly by conducting the Stobbe condensation in a more controlled manner. Condensation of 4 with the Wadsworth-Horner-Emmons reagent 10 (1.03 equiv, 1.1 equiv NaH, THF, 0 to 25° C., 12 h, 95–100%) provided 11 in which the required E-isomer predominated (>11:1 E:Z), FIG. 2, second scheme. Acid-catalyzed deprotection of 11 (100%) followed by Friedel-Crafts acylation of 5 affected by treatment with $Ac_2O$-KOAc (reflux, 1 h, 30 min) provided 7 in 65% recrystallized yield free of minor amounts of 9. In part, the improved conversions to provide 7 may be attributed to the facile closure of the correct E isomer of 5 and the milder reaction conditions and shorter reaction times employed since Z to E isomerization under the reaction conditions was no longer required. Hydrolysis of the O-acetate 7 by treatment with $K_2CO_3$-EtOH (reflux, 0.5–1 h, 81–100%) cleanly provided 6. This approach dependably provided 6 in overall conversions of 45–50% for the four steps and offered the additional advantages of the clean generation of the required E-5 and the ability to purify and characterize intermediates in route to 6. Protection of the free phenol 6 as its benzyl ether provided 12 (100%) (FIG. 2).

Figure 3:
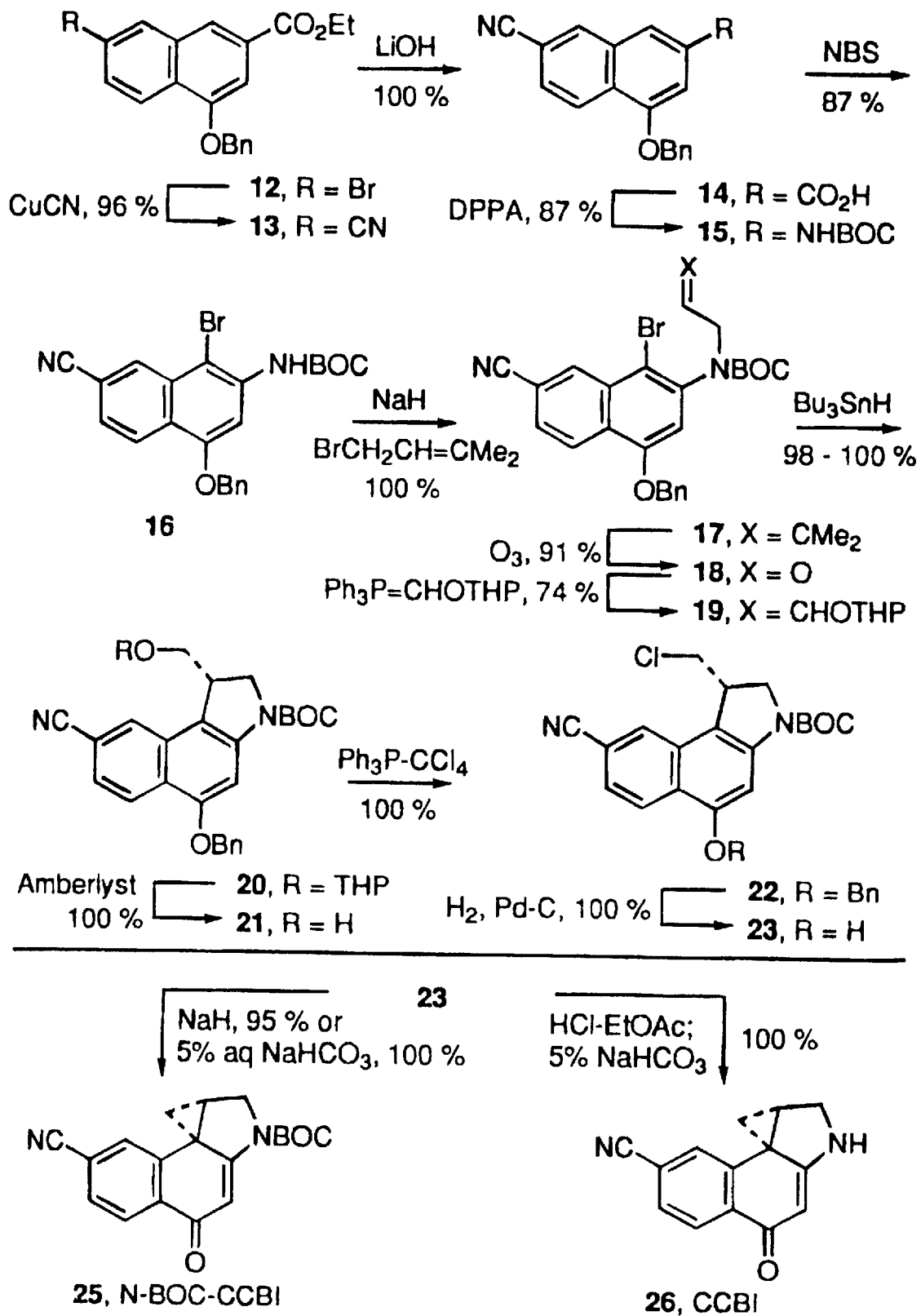
FIG. 3 illustrates the synthesis of advanced N-BOC CCBI intermediate 25 and CCBI intermediate 26.

At this stage, the C6 nitrile was introduced in a remarkably clean and effective reaction by simply treating 12 with CuCN in refluxing DMF to provide 13 (96%), FIG. 3. Hydrolysis of the ethyl ester (99–100%) followed by Curtius rearrangement of 14 effected by treatment of the carboxylic acid with the Shioiri-Yamada reagent (1.2 equiv DPPA, 1.2 equiv $Et_3N$, t-BuOH, reflux, 14 h, 87%) cleanly provided 15. In the optimization of this latter reaction, it was determined that use of rigorously dried t-BuOH, the use of dilute (0.005 M) or moderately dilute reaction conditions (0.025 M), and the maintenance of anhydrous reaction conditions through addition of 4 Å molecular sieves served to significantly reduce the amount of competitive symmetrical urea generation. Preliminary efforts to reverse the order of the steps in the conversion of 12 to 15 by first converting the ethyl ester to the corresponding t-butylcarbamate followed by CuCN replacement of the C6 bromide failed to provide 15 cleanly. Low-temperature, acid-catalyzed C4 bromination of 15 (1.2 equiv NBS, cat $H_2SO_4$, THF, −60° C., 4 h, 87%) cleanly provided 16 and alkylation of the sodium salt of 16 (1.3 equiv NaH, DMF, 25° C., 30 min) with 1-bromo-3-methyl-2-butene (3 equiv, DMF, 0–25° C., 12 h, 99–100%) afforded 17. Low temperature ozonolysis of 17 under carefully controlled reaction conditions followed by immediate reductive workup ($Me_2S$) of the crude ozonide provided the aldehyde 18 (91%). The use of extended reaction times or the failure to immediately quench the excess $O_3$ led to the rapid generation of a further oxidation product. Introduction of the vinyl ether 19 (74%) proved most effective with low temperature generation of $Ph_3P=CHOTHP$ in THF followed by reaction with 18 in THF-HMPA over a sustained reaction period. Treatment of 19 with $Bu_3SnH$ (2 equiv, 0.2 equiv AIBN, $C_6H_6$, 80° C., 2 h, 98–100%) provided the product of clean 5-exo-trig aryl radical-alkene cyclization 20 in excellent yield. Subsequent THP deprotection (100%), conversion of the primary alcohol 21 to the chloride 22 (100%) and phenol deprotection (100%) provided 23. Spirocyclization of 23 to provide N-BOC-CCBI (25) was effected by treatment with NaH (3 equiv, 0° C., 30 min, 95%) and acid-catalyzed deprotection of 23 (4 M HCl-EtOAc, 25° C., 30 min) followed by treatment of the crude indoline hydrochloride salt 24 with 5% aqueous $NaHCO_3$-THF (1:1, 25° C., 1.5 h, 100%) cleanly provided CCBI (26). Notably and because of the enhanced acidity of the phenol, simple treatment of 23 with 5% aqueous $NaHCO_3$-THF (1:1, 25° C., 9 h, 100%) led to clean spirocyclization to provide 25 without evidence of subsequent hydrolysis of the labile BOC (FIG. 3).

Figure 4:
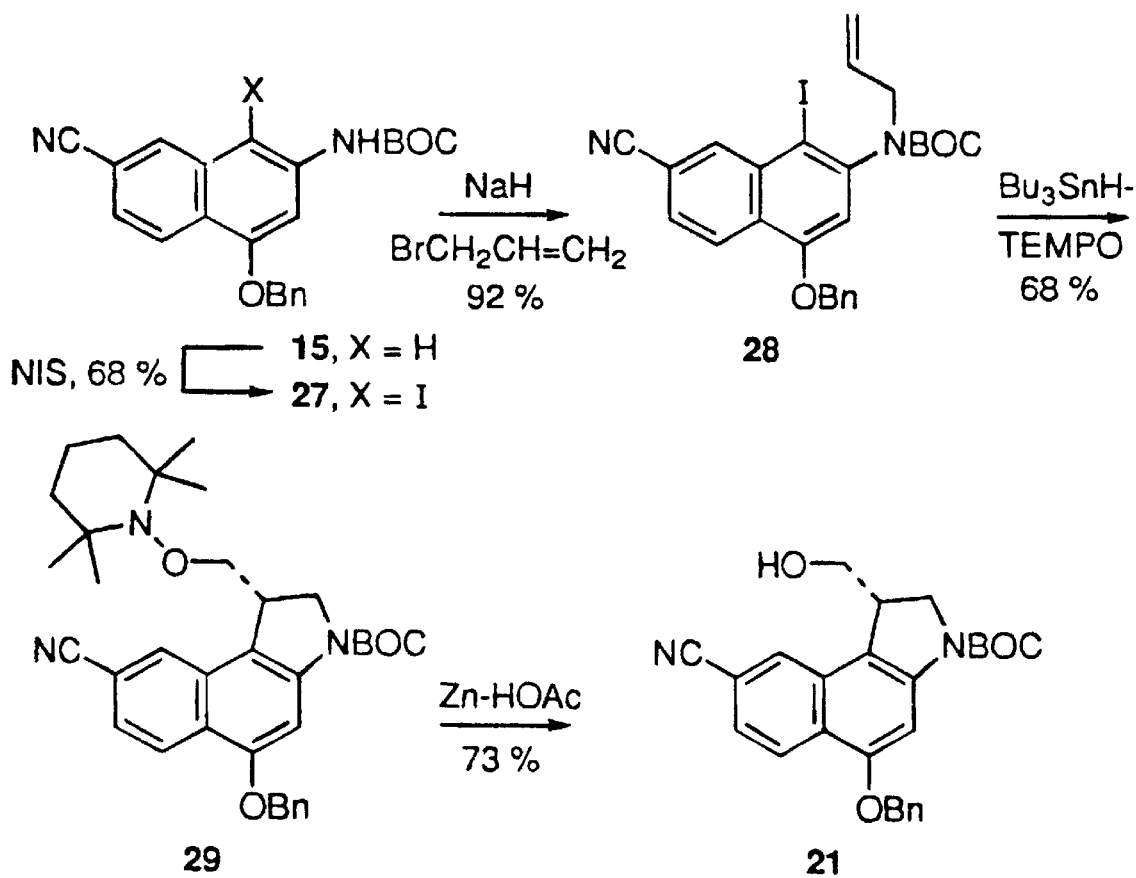
FIG. 4 illustrates the synthesis of advanced intermediate 21.

This approach to 25–26 was further shortened and improved with implementation of the Tempo trap of the 5-exo-trig aryl radical-alkene cyclization of the substrate 28 containing an unactivated and unfunctionalized acceptor alkene. Selective, acid-catalyzed C4 iodination of 15 effected by low-temperature treatment with NIS followed by alkylation of the sodium salt of 27 (1.5 equiv NaH, DMF, 25° C., 2 h) with allyl bromide (5 equiv, DMF, 25° C., 2 h, 92%) provided 28. Treatment of 28 with $BU_3SnH$ (5 equiv, 60° C., 1.5–2 h) in benzene in the presence of Tempo (5 equiv) cleanly provided 29. Reductive cleavage of 29 to provide 21 was effected by treatment with Zn (80 equiv, 3:1:1 THF-HOAc-$H_2O$, 70° C., 7 h, 73%) (FIG. 4).

The resolution of a late stage synthetic intermediate was accomplished by the chromatographic separation of the enantiomers of 22 on a Chiralcel-OD semipreparative HPLC column (2×25 cm) using a 7% i-PrOH-hexane eluent (7 mL/min), α=1.38. This routinely provided the two enantiomers of 22 in greater than 99.9% ee and with a 97% recovery. The intermediate 22 proved to be the only late stage intermediate which was effectively resolved on a Chiracel-OD column and similar efforts to separate 21 or 23 as well as N-BOC-CCBI (25) itself were not as successful. Subjection of both enantiomers of 22 to the conditions of catalytic hydrogenation for removal of the benzyl ether provided the enantiomers of 23 which were incorporated into the optically active agents 25–26 and 34–39. The assignment of the absolute configuration was tentatively based on the optical rotations of the final agents 25, 26, 33, 37, and 39 for which the strong positive rotation was assigned the natural configuration in analogy to all closely related studies and unambiguously established in the subsequent biological studies. Most notably, the distinct DNA alkylation selectivities characteristic of the natural and unnatural enantiomers for which prior stereochemical assignments have been unambiguously established were found to be in agreement with the initial assignments see Table 1 vida infra.

TABLE 1

Chromatographic Resolution[a]

| agent | solvent | α |
|---|---|---|
| 21 | 3–7% i-PrOH/hexane gradient | 1.09 |
| 22 | 5% i-PrOH/hexane | 1.33 |
| 22 | 7% i-PrOH/hexane | 1.38 |
| 23 | 2 or 3% i-PrOH/hexane | 1 |
| 25 | 15, 25 or 30% i-PrOH/hexane | 1 |

[a]Analytical 4.6 × 250 mm, 10 μm Chiralcel-OD column, 1 mL/min

Figure 5:
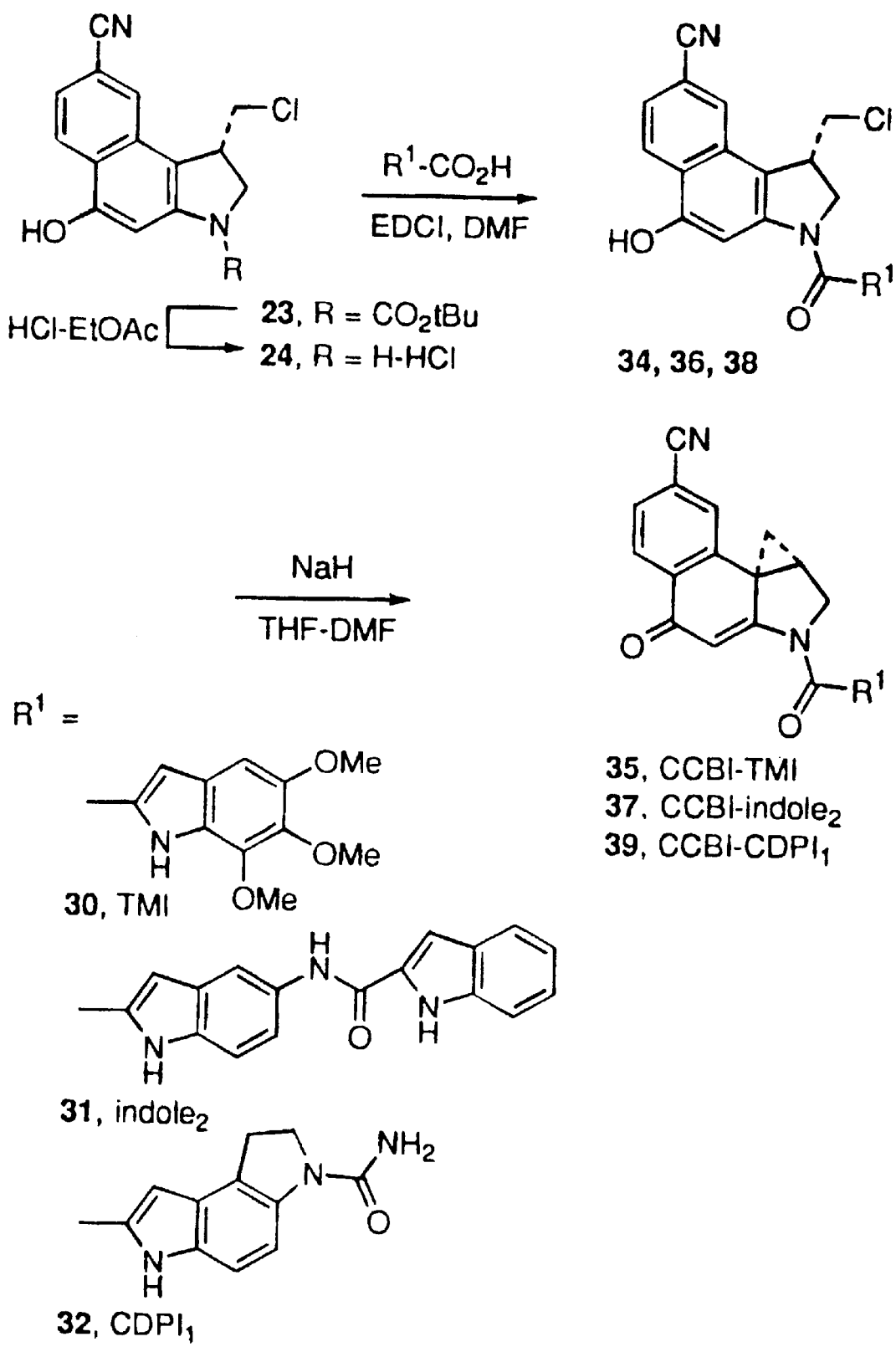
FIG. 5 illustrates the synthesis of CCBI duocarmycin analogs CCBI-TMI 35, CCBI-indole$_2$ 37 and CCBI-CDPI$_1$ 39.

CCBI-TMI (35), CCBI-indole$_2$ (37), and CCBI-CDPI (39). The CCBI alkylation subunit was incorporated into the CC-1065 and duocarmycin analogs 34–39 as detailed in FIG. 5. Acid-catalyzed deprotection of 23 (4 M HCl-EtOAc, 25° C., 30 min, quantitative) followed by coupling of the unstable indoline hydrochloride salt 24 with 5,6,7-trimethoxyindole-2-carboxylic acid (30, 3 equiv EDCI, DMF, 25° C., 14 h, 85%), 31 (3 equiv EDCI, DMF, 25° C., 16 h, 87%), and CDPI$_1$ (32, 3 equiv EDCI, DMF, 25° C., 16 h, 81%) conducted in the absence of added base provided the agents 34, 36 and 38, respectively. Interestingly, the agent 24 was found to couple less effectively than prior agents and the slower coupling reactions in the series (e.g., CDPI$_2$) were less successful. These slower coupling reactions, which can be attributed principally to the insolubility of the carboxylic acids even in DMF, suffered competitive ring closure of 24 to CCBI (26). In part, this distinction of 24 may be attributed to the increased phenol acidity leading to a more facile deprotonation and spirocyclization competitive with coupling. Subsequent treatment of the coupled agents with NaH (3 equiv, 20% DMF-THF, 0° C., 30 min) provided CCBI-TMI (35, 99%) and CCBI-indole$_2$ (37, 66%) in good conversion. More remarkable, simple exposure of 36 to 3% aqueous NaHCO$_3$-THF (1:1, 25° C., 3 h, 68%) or 38 to KHCO$_3$ in DMF-H$_2$O (5:2, 25° C., 9–10 h, 69%) provided spirocyclization to provide 37 and 39 without evidence of significant subsequent hydrolysis of the labile amide.

In Vitro Cytotoxic Activity. The results of a study of the comparative cytotoxic properties of the CCBI-based agents alongside the corresponding CBI and MCBI agents are detailed in FIG. 6. In preliminary studies, the natural enantiomers of the CCBI-based agents have been found to exhibit the most potent cytotoxic activity in CBI series (FIG. 6).

Figure 7A:
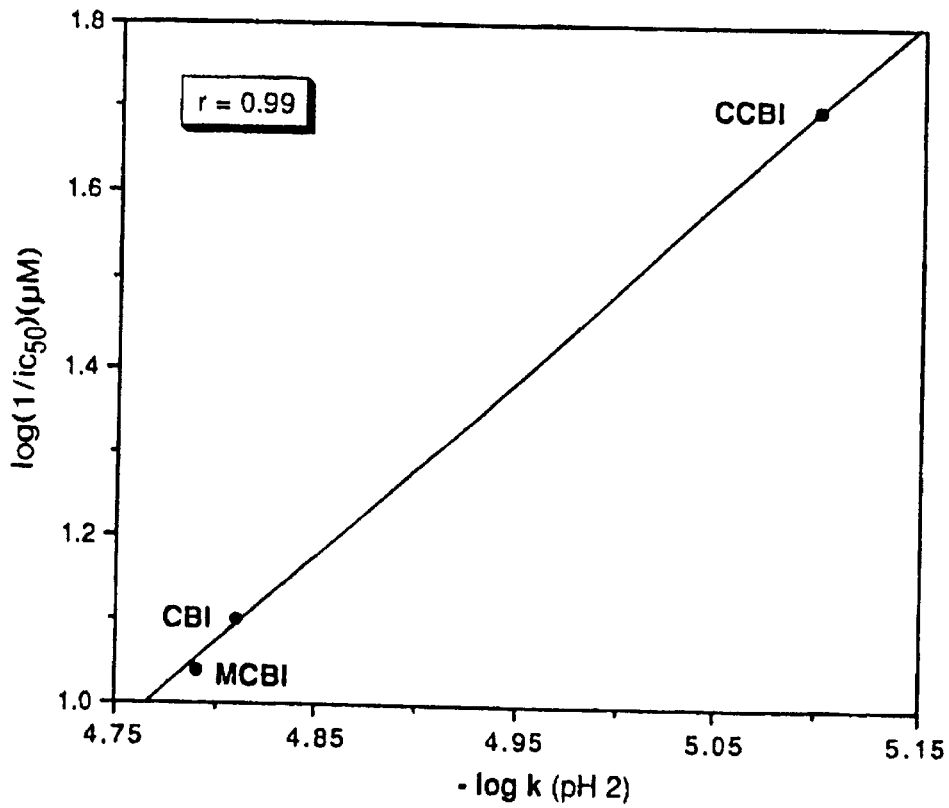
FIG. 7 illustrates a direct relationship between chemical stability (−log k) and in vitro cytotoxic potency (L1210, log 1/IC$_{50}$) over the narrow range of reactivity examined by the series.
Figure 7B:
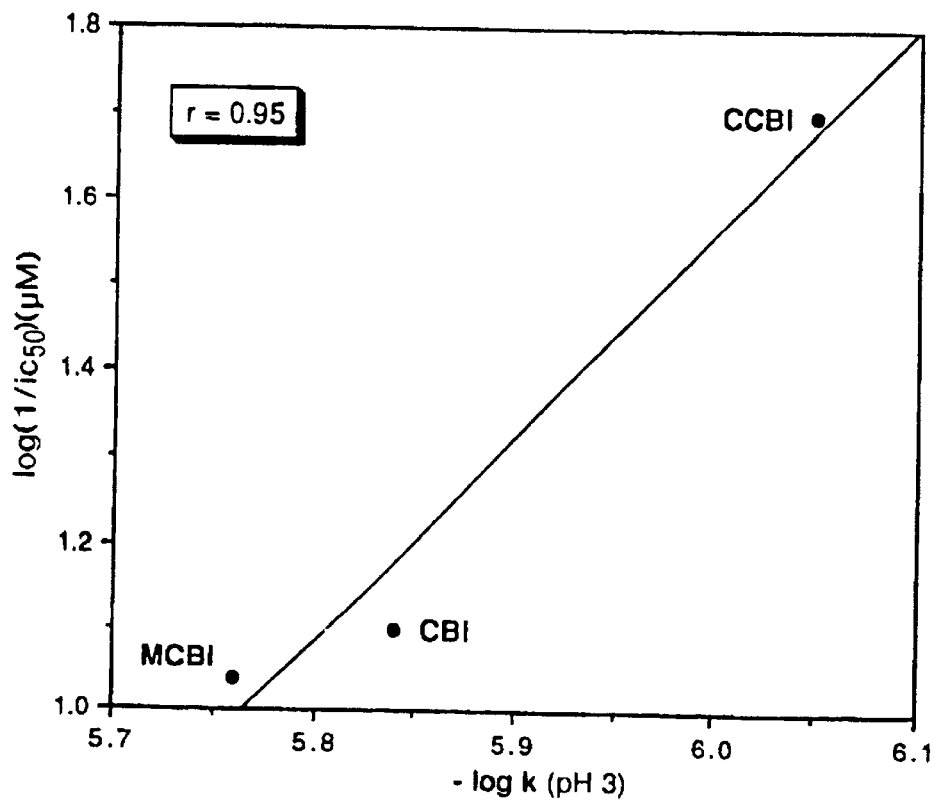

Consistent with past observations, the agents were found to follow a direct relationship between chemical stability (-log k) and in vitro cytotoxic potency (L1210, log 1/IC$_{50}$) over the narrow range of reactivity examined by the series. This is illustrated in FIG. 7 with the N-BOC derivatives. Presumably this may be attributed to the more effective delivery of the more stable agents to their intracellular target and the solvolysis rates may be taken to accurately represent the relative functional reactivity/stability of the agents.

Figure 8:
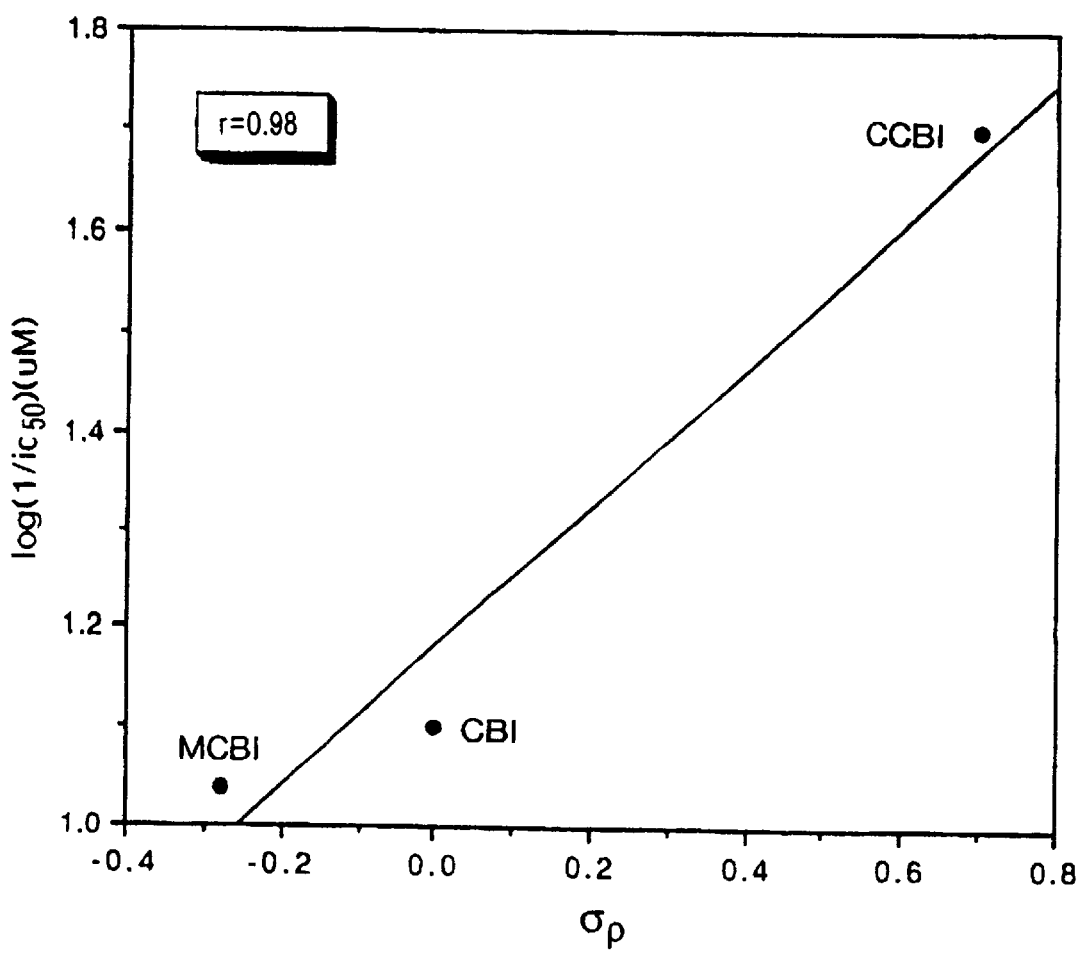
FIG. 8 illustrates a direct relationship between in vitro cytotoxic activity and the Hammet σ$_p$ constant of the C7 substituent with CCBI providing the most potent agent.

Less obvious, but more fundamental, the observations were found to follow a predictable direct relationship between in vitro cytotoxic activity and the Hammett σ$_p$ constant of the C7 substituent with CCBI providing the most potent agent (FIG. 8). This fundamental relationship should prove useful in the design of new analogs possessing further enhanced properties.

Figure 10A:
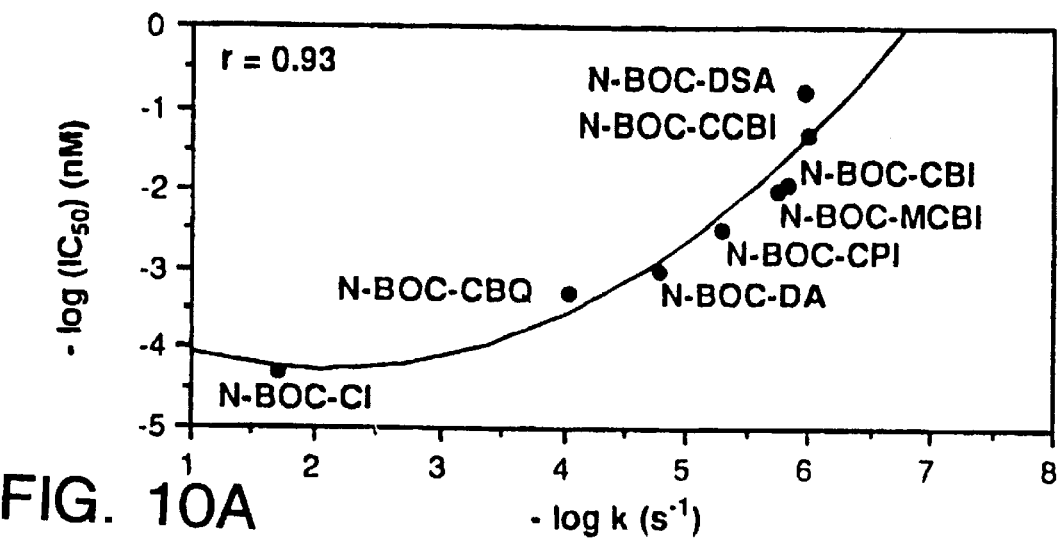
FIG. 10 illustrates comparisons made on three presently available agents which follow trends of related full structure analogs.
Figure 10B:
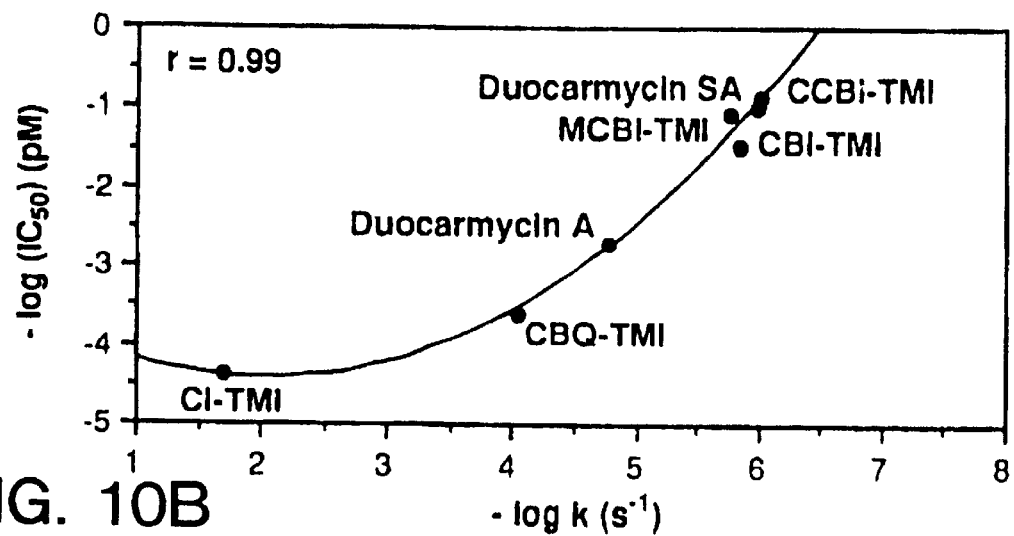
Figure 10C:
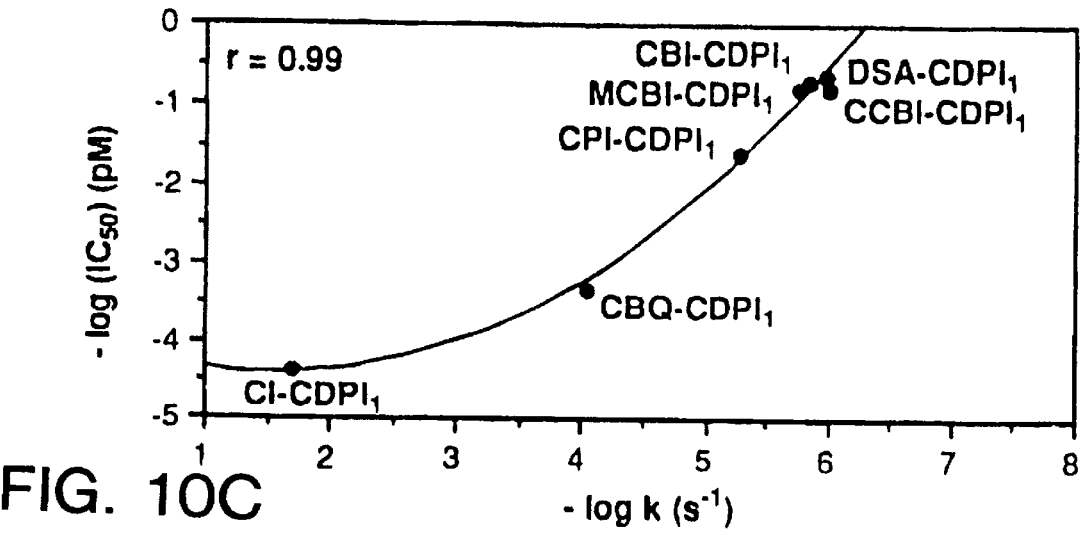

While the latter two correlations are limited to the comparisons made on the three presently available agents, they also follow trends established in the examination of 44–49 (FIG. 9) and their related full structure analogs (FIG. 10) further supporting their potential generality. Notably, 25 is the most stable and one of the most synthetically accessible alkylation subunits disclosed to date.

Analogous to prior observations, the corresponding seco precursors 23, 34, 36, and 38 exhibited cytotoxic activity indistinguishable from the cyclopropane containing agents.

DNA Alkylation Selectivity and Efficiency. The DNA alkylation properties of the agents were examined within w794 duplex DNA, a 144 base-pair segment of duplex DNA for which comparative results are available for related agents. The alkylation site identification and the assessment of the relative selectivity among the available sites were obtained by thermally-induced strand cleavage of the singly 5' end-labeled duplex DNA after exposure to the agents. Following treatment of the end-labeled duplex DNA with a range of agent concentrations, the unbound agent was removed by EtOH precipitation of the DNA. Redissolution of the DNA in aqueous buffer, thermolysis (100° C., 30 min) to induce strand cleavage at the sites of DNA alkylation, denaturing high resolution polyacrylamide gel electrophoresis (PAGE) adjacent to Sanger dideoxynucleotide sequencing standards, and autoradiography led to identification of the DNA cleavage and alkylation sites. The DNA alkylation reaction selectivities observed under the incubation conditions for the agents detailed herein have proven identical to the alkylation selectivities observed with shorter or extended reaction periods or when the reactions were conducted at different temperatures (37 or 4° C., 0.5–7 d). As discussed below, the rates and efficiencies but not final relative efficiencies of DNA alkylation were altered by changing the reaction temperatures.

Figure 11:
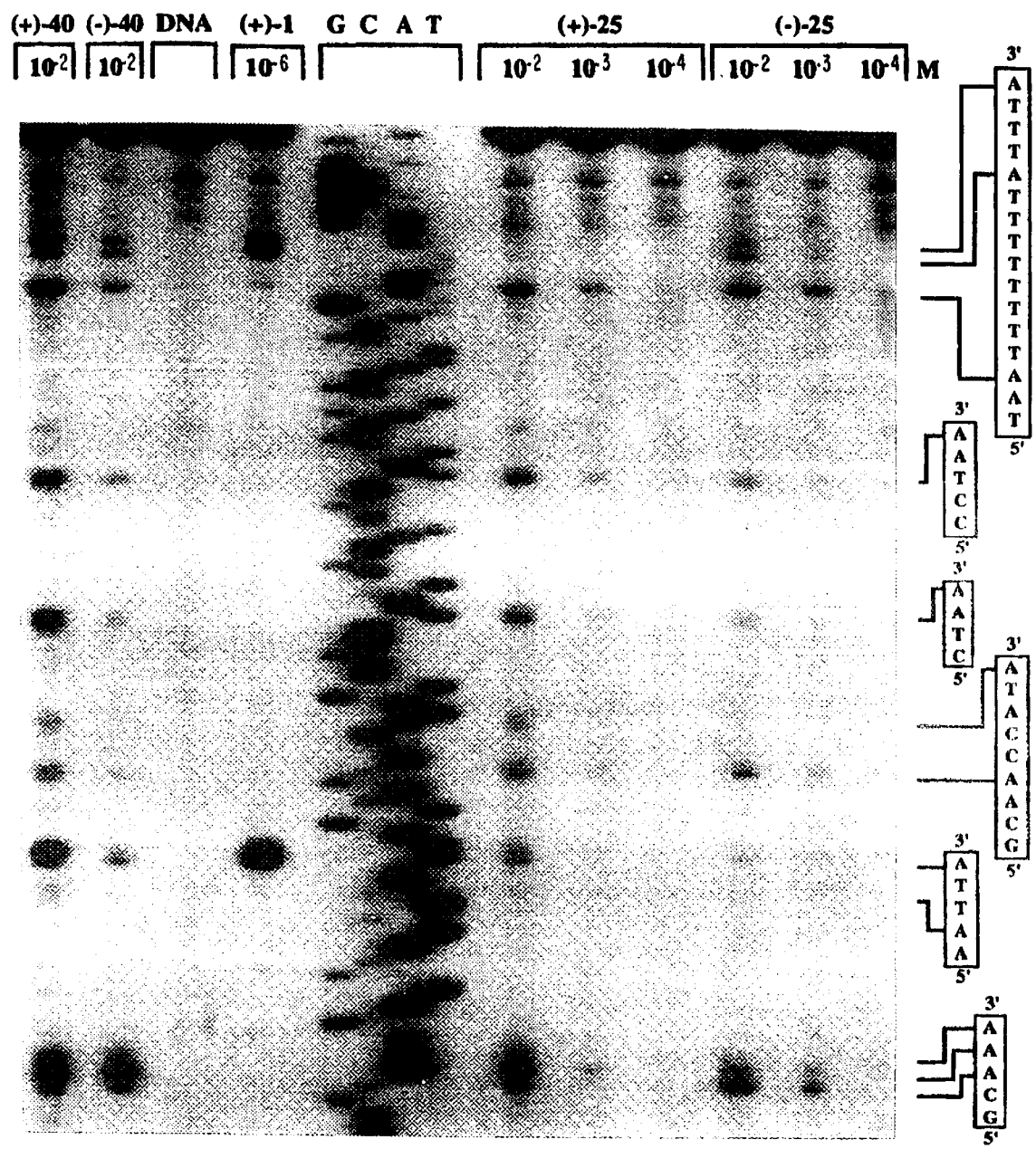
FIG. 11 illustrates thermally-induced strand cleavage of double-stranded DNA (SV40 DNA fragment, 144 bp, nucleotide no. 5238-138, clone w794) after 72 h incubation of agent with DNA at 37° C. followed by removal of unbound agent, and 30 min incubation at 100° C., 8% denaturing PAGE and autoradiography. Lane 1, (+)-N-BOC-MCBI (1×10$^{-2}$ M); lane 2, ent-(−)-N-BOC-MCBI (1×10$^{-2}$ M); lane 3, control DNA; lane 4, (+)-CC-1065 (1×10$^{-6}$ M); lanes 5–8, Sanger G, C, A and T reactions; lanes 9–11 (+)-N-BOC-CCBI (1×10$^{-2}$ to 1×10$^{-4}$ M); lanes 12–14, ent-(−)-N-BOC-CCBI (1×10$^{-2}$ to 1×10$^{-4}$ M).

DNA Alkylation Properties of (+)- and ent-(−)-N-BOC-CCBI. A representative comparison of the DNA alkylation properties of both enantiomers of N-BOC-CCBI (25) alongside both enantiomers of N-BOC-MCBI (40) within w794 DNA is illustrated in FIG. 11. No substantial distinctions between N-BOC-CCBI (25) and N-BOC-MCBI (40) were detected. Both natural enantiomers exhibited comparable efficiences of DNA alkylation detectable at 10$^{-3}$ M (37° C., 72 h) and prominent at 10$^{-2}$ M and both were only slightly more efficient than the corresponding unnatural enantiomers (1–2×). This efficiency of DNA alkylation proved analogous to that of (+)-N-BOC-CBI (41) but distinct from the unnatural enantiomer of N-BOC-CBI: (+)-N-BOC-CBI/ent-(−)-N-BOC-CBI (5–10×) versus (+)-N-BOC-CCBI/ent-(−)-N-BOC-CCBI and (+)-N-BOC-MCBI/ent-(−)-N-BOC-MCBI (1–2×). This distinction between the enantiomers of 41 which was not observed with 40 or 25 was also accurately reflected in the relative cytotoxic potencies of the agents where the unnatural enantiomers of both N-BOC-CCBI (4×) and N-BOC-MCBI (2×) more closely approach that of the corresponding natural enantiomers than that of N-BOC-CBI (11×). Like the preceding BOC derivatives examined, the two enantiomers of 25 alkylated DNA much less efficiently than 34–39 (10$^4$×) providing detectable alkylation at 10$^{-2}$ to 10$^{-3}$ M (37° C., 24–72 h), much less selectively than 34–39 exhibiting a two base-pair AT-rich alkylation selectivity (5'-AA>5'-TA), and did so with alkylation of the same sites. This unusual behavior of the two enantiomers alkylating the same sites is analogous to past observations. It is a natural consequence of the reversed binding orientations of the two enantiomers and the diastereomeric relationship of the two adducts which result in the two enantiomers covering the exact same binding site surrounding the alkylated adenine.

DNA Alkylation Properties of the Natural Enautiomers of CCBI-TMI (35), CCBI-indole$_2$ (37), and CCBI-CDPI (39).

Figure 12:
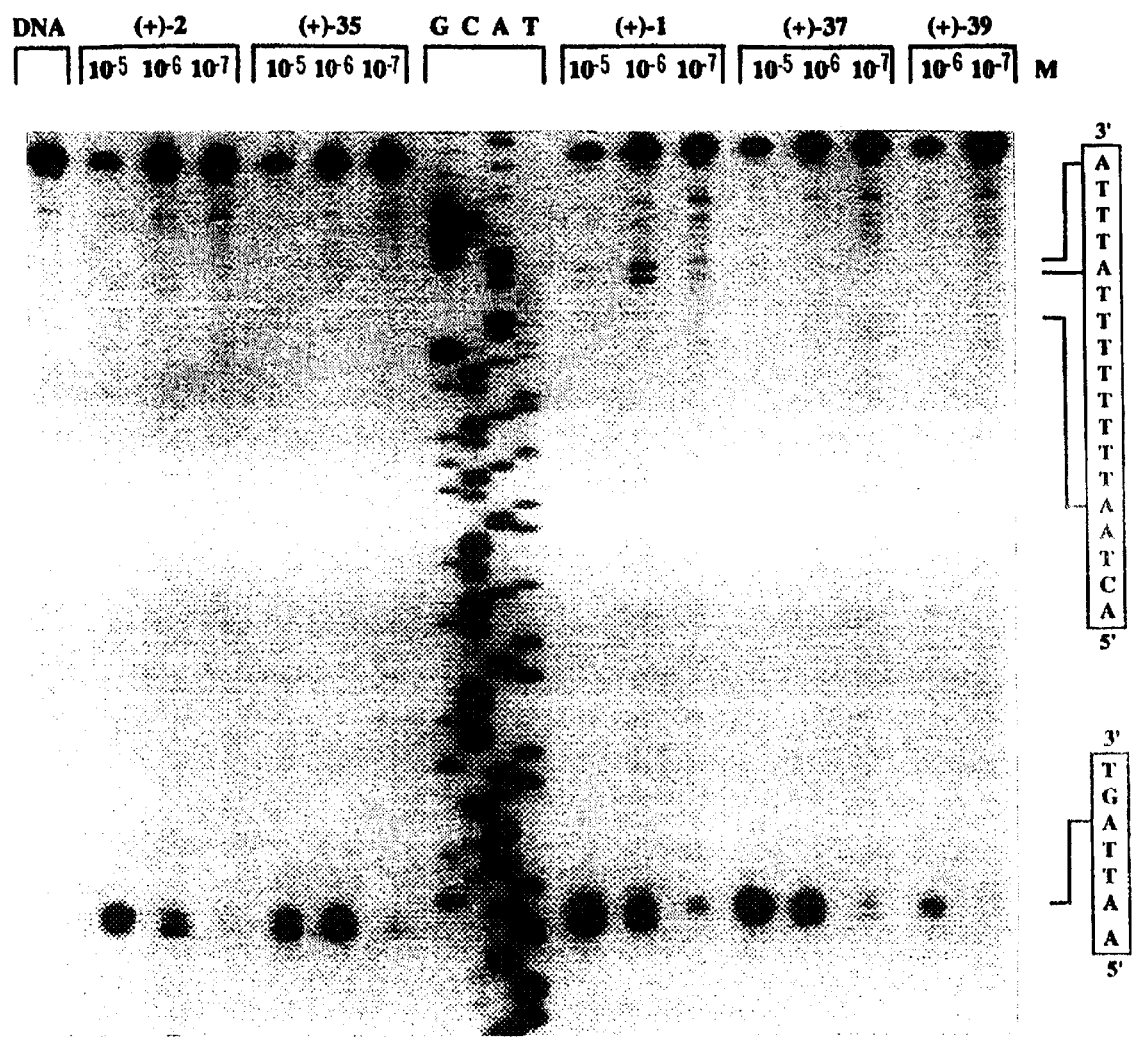
FIG. 12 illustrates thermally-induced strand cleavage of double-stranded DNA (SV40 DNA fragment, 144 bp, nucleotide no. 5238-138, clone w794) after 24 h incubation of agent-DNA at 25° C. followed by removal of unbound agent, 30 min incubation at 100° C., 8% denaturing PAGE and autoradiography. Lane 1, control DNA; lanes 2–4, (+)-duocarmycin SA (2, 1×10$^{-5}$ to 1×10$^{-7}$ M); lanes 5–7, (+)-CCBI-TMI (1×10$^{-5}$ to 1×10$^{-7}$ M); lanes 8–11, Sanger G, C, A and T reactions; lanes 12–14, (+)-CC-1065 (1, 1×10$^{-5}$ to 1×10$^{-7}$ M); lanes 15–17, (+)-CCBI-indole$_2$ (1×10$^{-5}$ to 1×10$^{-7}$ M); lanes 18–19, (+)-CCBI-CDPI$_1$ (1×10$^{-6}$ and 1×10$^{-7}$ M).

A comparison of the DNA alkylation by the natural enantiomers of 35, 37, and 39 alongside (+)-duocarmycin SA (2) and (+)-CC-1065 (1) within w794 DNA is illustrated in FIG. 12 and is representative of comparisons that have been made with the agents. (+)-Duocarmycin SA (2) and (+)-CCBI-TMI (35) were indistinguishable and the two agents exhibited the same selectivity and efficiency of DNA alkylation. This is illustrated nicely in FIG. 12 where the two agents detectably alkylate the same high affinity site of 5'-AATTA at $10^{-6}$ to $10^{-7}$ M (25° C., 24 h). This is analogous to the observations made in our prior comparisons of duocarmycin SA (2) and CBI-TMI or MCBI-TMI.

Each alkylation site detected was adenine followed by two 5' A or T bases in a three base-pair site that follows the following preference: 5'-AA<u>A</u>>5'-TTA>5'-TA<u>A</u>>5'-ATA. For the shorter agents CCBI-TMI and CCBI-CDPI$_1$, there was also a strong preference but not absolute requirement for the fourth 5' base to be A or T versus G or C and this preference distinguished many of the high versus low affinity sites (e.g., 5'-AAA<u>A</u>). For the longer agent, CCBI-indole$_2$, not only was there a stronger preference for the fourth base to be A or T but that preference extended to include a fifth 5' A or T base (e.g., 5'-AAAA<u>A</u>). Thus, like the preceding agents, the CCBI-based agents exhibited AT-rich adenine N3 alkylation selectivities that start at the 3' adenine N3 alkylation site with agent binding in the minor groove in the 3'-5' direction covering 3.5 or 5 base pairs.

Figure 13:
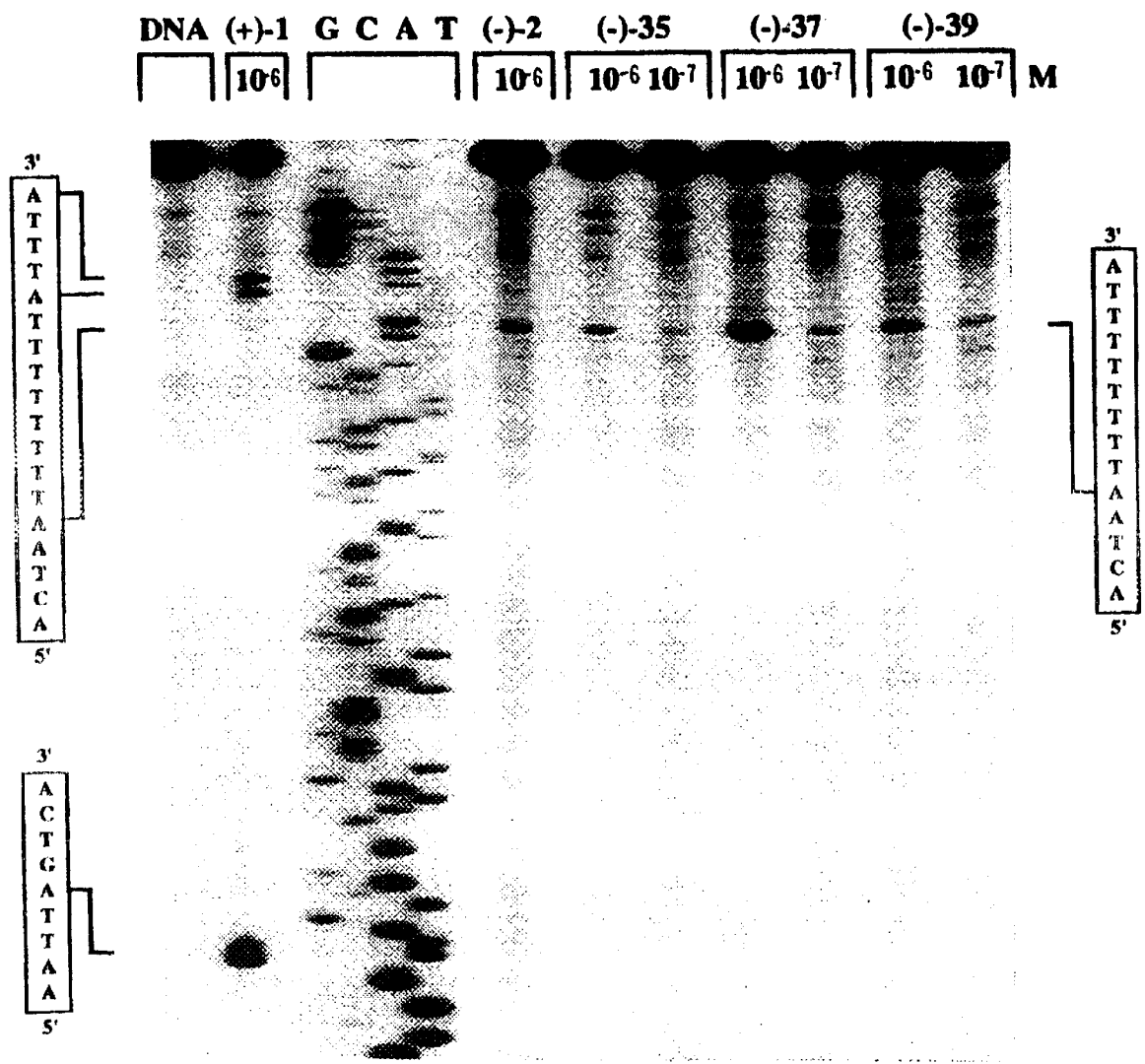
FIG. 13 illustrates thermally-induced strand cleavage of duplex DNA (SV40 DNA segment, 144 bp, nucleotide no. 5238-138, clone w794) after 72 h incubation at 25° C. followed by removal of unbound agent, 30 min incubation at 100° C., 8% denaturing PAGE and autoradiography. Lane 1, control DNA; lane 2, (+)-CC-1065 (1×10$^{-6}$ M); lanes 3–6, Sanger G, C, A, and T sequencing reactions; lane 7, ent-(−)-duocarmycin SA (1×10$^{-6}$ M); lanes 8–9, ent-(−)-CCBI-TMI (1×10$^{-6}$ and 10$^{-7}$ M); lanes 10–11, ent-(−)-CCBI-indole$_2$ (1×10$^{-6}$ and 10$^{-7}$ M); lanes 12–13, ent-(−)-CCBI-CDPI$_1$ (1×10$^{-6}$ and 10$^{-7}$ M).

DNA Alkylation Properties of the Unnatural Enantiomers of CCBI-TMI (35), CCBI-indole$_2$ (37), and CCBI-CDPI$_1$ (39). A representative comparison of the DNA alkylation by the unnatural enantiomers of the CCBI-based agents alongside the unnatural enantiomer of duocarmycin SA (1) and the natural enantiomer of CC-1065 (1) in w794 of DNA is illustrated in FIG. 13. Several important findings analogous to those made in our prior studies with the CBI-based agents are also observed with the CCBI-based agents. First, the unnatural enantiomer DNA alkylation is considerably slower and the results shown in FIG. 13 for the unnatural enantiomers were obtained only with incubation at 25° C. (72 h) versus incubation at 25° C. (24 h, FIG. 12) for the natural enantiomers. Even with the more vigorous reaction conditions (37° C.) or the more extended reaction periods, the extent of alkylation by the unnatural enantiomers is lower requiring higher agent concentrations to detect. This distinguishing difference in the rate and efficiency of DNA alkylation was most prominent with the smaller agents CCBI-TMI (35) and duocarmycin SA (2) and readily perceptible but less prominent with the intermediate sized agents CCBI-CDPI$_1$ (39) and CCBI-indole$_2$ (37). This trend is similar to that observed in the relative cytotoxic potency of the enantiomeric pairs.

The DNA alkylation selectivity and efficiency observed with ent-(−)-CCBI-TMI (35) and ent-(−)-duocarmycin SA (2) were nearly indistinguishable with the latter agent being slightly more effective. This observation is analogous to that made in our prior comparisons with (−)-MCBI-TMI but different from that made with (−)-CBI-TMI where the distinction was even larger (10×). The larger agents were more effective at alkylating DNA, (−)-CCBI-indole$_2$>(−)-CCBI-CDPI$_1$>(−)-CCBI-TMI, and even with incubation at 25° C. for 72 h the more effective agents did not achieve the efficiency observed with the natural enantiomers. This is illustrated nicely in FIG. 13 with the comparison of the unreacted DNA observed at $10^{-6}$ M for (+)-CC-1065 (1) versus the full set of CCBI unnatural enantiomers. Again, no distinctions in the DNA alkylation selectivity of the unnatural enantiomers of the CCBI-based agents and the agents described previously were perceptible. Each of the alkylation sites proved to be adenine which was flanked on both sides nearly always by an A or T base and the preference for this three base AT-rich site was 5'-A<u>A</u>A>5'-T<u>A</u>A>5'-AAT>5'-TAT. For the shorter agents, there was a strong preference for the second 3' base to be A or T (e.g., 5'-A<u>A</u>AA) which for the larger agents extended to the third 3' base as well (e.g., 5'-A<u>A</u>AAA). Thus, each alkylation site for the unnatural enantiomers proved consistent with adenine N3 alkylation with agent binding in the minor groove in the revers 5'-3' direction across a 3.5 or 5 base-pair AT-rich site surrounding the alkylation site. This is analogous to the natural enantiomer alkylation selectivity except that it extends in the reverse 5'-3' direction in the minor groove and, because of the diastereomeric nature of the adducts, is offset by one base-pair relative to the natural enantiomers.

Figure 14A:
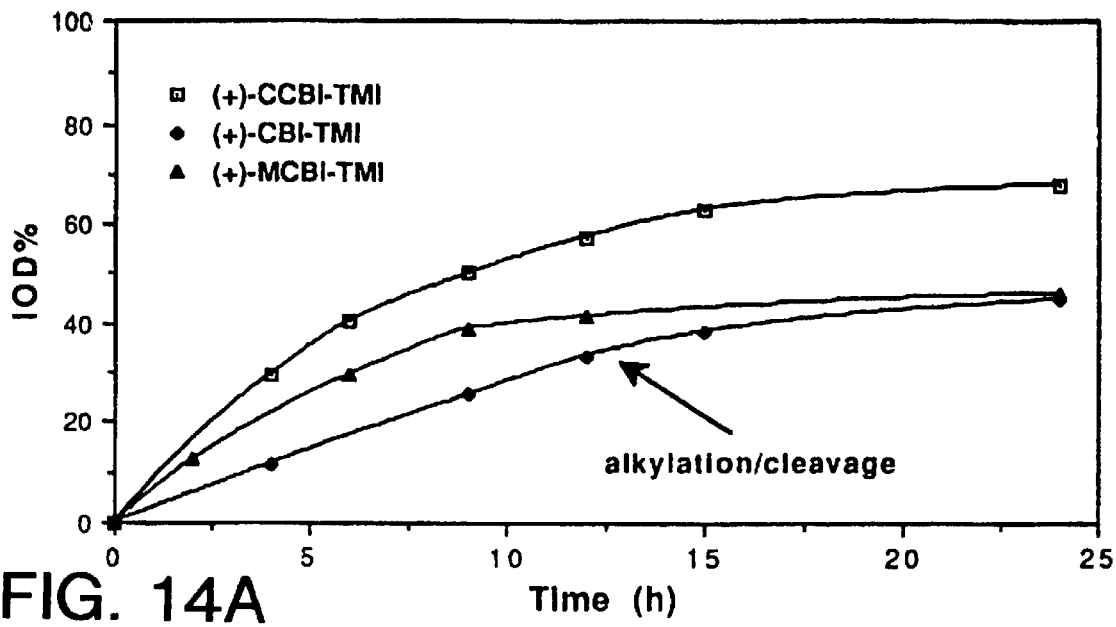
FIG. 14 illustrates a plot of percent integrated optical density (IOD %) versus time established through autoradiography of 5'-$^{32}$P end-labeled DNA and used to monitor the relative rate of w794 alkylation at the 5'-AATTA high affinity site for 35, 37, (+)-CBI-TMI, (+)-MCBI-TMI, (+)-CBI-indole$_2$, and (+)-MCBI-indole$_2$.
Figure 14B:
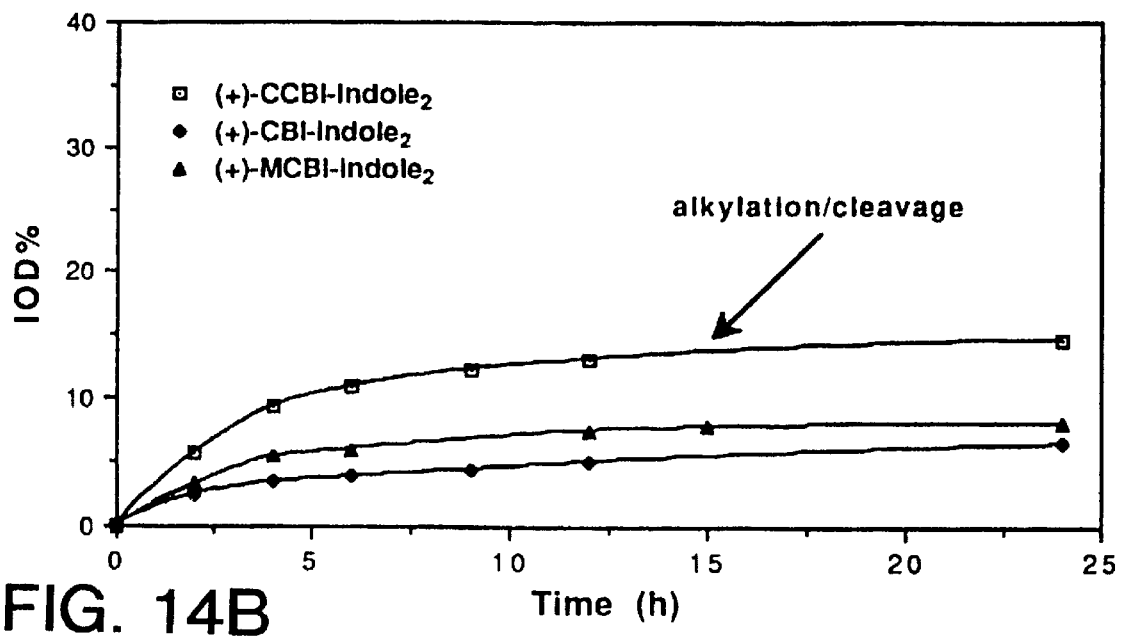
Figure 17:
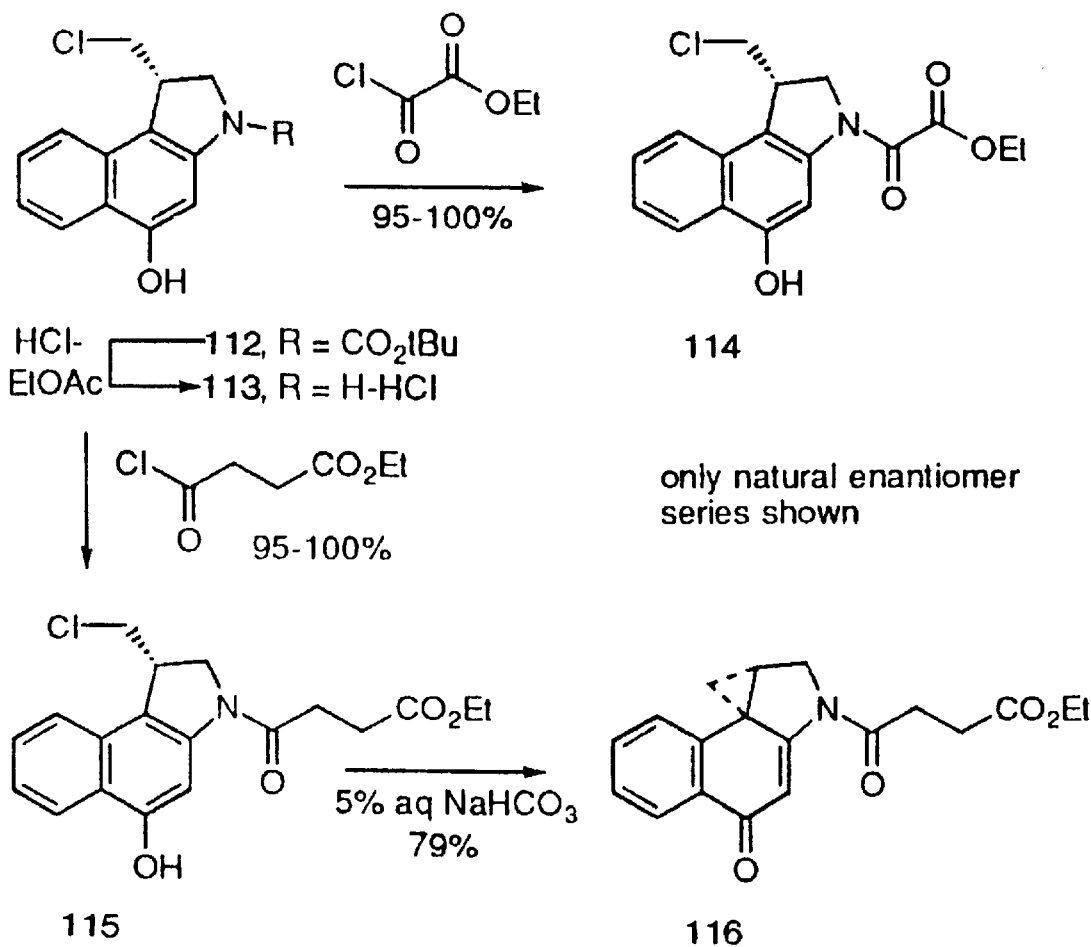
FIG. 17 illustrates the synthesis of intermediate 16.

Rate of DNA Alkylation. The relative rates of DNA alkylation for the natural enantiommers of CCBI-TMI (35) and CCBI-indole$_2$ (37) versus those of the corresponding CBI and MCBI agents were measured at the single high affinity site in w794, 5'-AATTA. The relative rates earlier studies of DNA alkylation for MCBI-TMI, CBI-TMI, and duocarmycin SA were determined to be quite similar at 4° C., 1.8:1.0:0.9, respectively. The same relative rates were observed in the present study now extended to include CCBI-TMI (35) and this latter agent proved to alkylate DNA with the fastest relative rate ($10^{-6}$ M, 25° C.): CCBI-TMI (2.5×)>MCBI-TMI (1.9×)>CBI-TMI (1.0)>duocarmycin SA (0.9×) (FIG. 14). The relative rates of DNA alkylation CCBI-indole$_2$ (2.5×), MCBI-indole$_2$ (1.4×), and CBI-indole$_2$ (1.0) at 25° C. were determined to exhibit nearly identical trends. Although the studies are limited to a very narrow reactivity range difficult to distinguish, the rate DNA alkylation did not correlate with the relative reactivity of the agents toward acid-catalyzed solvolysis suggesting that other or additional factors may contribute to the rate or are responsible for the catalysis of the DNA alkylation reaction. In prior studies, we have highlighted similar observations with agents that span a much larger range of relative reactivities.

More interestingly, the final relative efficiency of DNA alkylation observed under these reaction conditions did more closely follow the trends of the relative reactivities of the agents. The chemically more stable CCBI based agents 35 and 37 alkylated DNA 1.5–2× more efficiently than the MCBI or CBI based agents which in turn were essentially indistinguishable. Nearly identical trends were observed in the relative stability of the agents with CCBI being 1.6–2.1× more stable than CBI or MCBI which in turn were very close in stability 1.06–1.2×. Such observations are consistent with our prior studies that suggest it is not the rate of DNA alkylation that may be related to the cytotoxic potency of the agents, but rather the ultimate efficiency of DNA alkylation that may be more relevant to the expression of their biological properties. Just as importantly, they also suggest that other factors are contributing to the DNA alkylation reaction and that other or additional features beyond C4 carbonyl protonation or Lewis acid complexation may be responsible for catalysis. Most prevalent among these possibilities is activation by ground state destabilization derived through a DNA binding induced conformational change that activates the agent for nucleophilic addition. Studies which address such issues are in progress and will be reported in due course.

Figure 18:
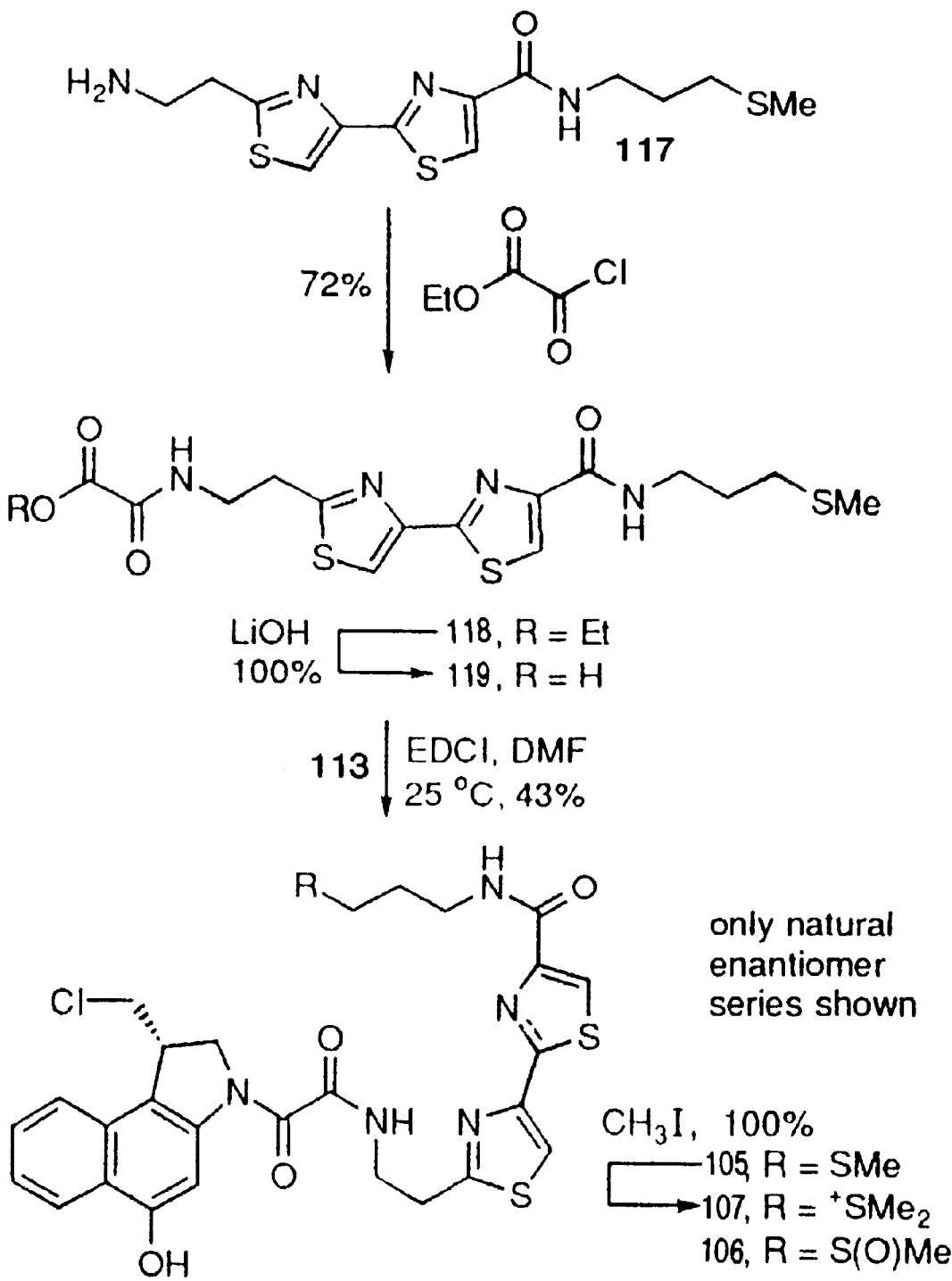
FIG. 18 illustrates the synthesis of analogs 6 and 7.

Conclusions. A short and efficient synthesis of CCBI and its immediate precursors is detailed. Its evaluation permitted an accurate assessment of the electronic effect of substituents on the chemical and functional reactivity of the agents and the impact this may have on their biological properties. A study of the solvolysis reactivity of N-BOC-CCBI and its comparison with related agents revealed that the introduction of a strong electron-withdrawing C7 cyano group slowed the rate of solvolysis but the effect was very small. Classical Hammett quantitation of the effect provided a remarkably small p (−0.3) indicating an exceptionally small C7 substituent electronic effect on functional reactivity. Additional kinetic studies demonstrated that protonation of the C4 carbonyl is not the rate determining step of solvolysis or acid-catalyzed nucleophilic addition, but rather that it is rapid and reversible followed by slow and rate determining nucleophilic addition to the cyclopropane requiring the presence and assistance of a nucleophile ($S_N2$ mechanism). No doubt this contributes to the DNA alkylation selectivity and suggests that the positioning of an accessible nucleophile (adenine N3) and not C4 carbonyl protonation or Lewis acid complexation is the rate determining step controlling the sequence selectivity of DNA alkylation. This exceptionally small electronic effect on the solvolysis rate had no impact on the solvolysis regioselectivity and stereoelectronically-controlled nucleophilic addition to the least substituted carbon of the activated cyclopropane was observed exclusively. Consistent with past studies, a direct relationship between solvolysis stability and cytotoxic potency was demonstrated and related to the predictable Hammett substituent effects. For the natural enantiomers, this very small electronic effect on functional reactivity had no perceptible effect on their DNA alkylation selectivity. Although the range of reactivity spanned by the agents is quite small and the effects difficult to distinguish, the efficiencies but not the rates of DNA alkylation were found to correlate with the relative reactivities of the agents with the most stable agent in the series providing the most efficient DNA alkylation as well as most potent cytotoxic activity. Similar effects of the C7 cyano group on the unnatural enantiomers were detected and they proved to be 4–10× more effective than the corresponding CBI-based unnatural enantiomer and 4–70× less potent than the corresponding CCBI natural enantiomer.

EXAMPLE 2

CC-1065/Duocarmycin and Bleomycin A2 Hybrid Agents: Lack of Enhancement of DNA Alkylation by Attachment to Noncomplementary DNA Binding Subunits Hybrid agents 105–111 containing the C-terminus DNA binding domain of bleomycin $A_2$ linked to the CBI analog of the CC-1065 and duocarmycin DNA alkylation subunits were prepared and evaluated. The agents exhibited little or no enhancement of the DNA alkylation efficiency and in some cases the linkage resulted in diminished properties relative to the simple alkylation subunit itself. Moreover, the DNA alkylation selectivity (5'-AA>5'-TA) of the resulting agents proved identical to that of simple derivatives of the CBI alkylation subunit, e.g. N-BOC-CBI. Thus, the linkage to the DNA binding domain of bleomycin $A_2$ did not alter this inherent DNA alkylation selectivity to reflect a DNA binding or cleavage selectivity of bleomycin $A_2$ nor did it reflect the greater 5- or 3.5-base-pair AT-rich selectivities observed with CC-1065 or the duocarmycins, respectively. Consistent with these observations, the cytotoxic properties of 105–111 were diminished relative to those of even simple derivatives of the CC-1065/duocarmycin alkylation subunits, e.g. N-BOC-CBI.

The bleomycins are a family of clinically effective glycopeptide antitumor antibiotics of which bleomycin $A_2$ (104) is the major constituent (FIG. 15). It is generally accepted that they derive their therapeutic effects through the ability to mediate the oxidative cleavage of duplex DNA or RNA by a process that is metal ion and oxygen dependent. The C-terminus tripeptide S subunit of bleomycin $A_2$ including the sulfonium cation and the bithiazole provide the majority of the DNA binding affinity ($K_{app}$=0.26 vs. 1.0×$10^5$ $M^1$) while the amino terminus pyrimidoblamic acid subunit in conjunction with the adjacent erythro- -hydroxy-L-histidine provides the metal chelation/oxygen activation and polynucleotide recognition. DNA binding properties of N-BOC di-, tri-, tetra- and pentapeptide S and related structures (Kpp=0.1, 0.26, 0.21 and 0.23×$10^5$ $M^{-1}$) including a determination of their apparent binding site sizes (2.2, 3.6, 3.7, and 4.2 vs. 3.8 base-pairs for 104) suggested that the natural agent adopts a bent bound conformation with tripeptide S fully bound to DNA incorporating a reverse turn and swivel point in the peptide backbone at the tripeptide S-tetrapeptide S junction. Structural NMR of bleomycin $A_2$ bound to a cleavage site within an oligonucleotide were found to embody the basic tenants of this nonstructural model (FIG. 15).

In this example, we describe the preparation and evaluation of the series of hybrid agents 105–111 of CC-1065/duocarmycins and the bleomycins which incorporate the CBI analog of the DNA alkylation subunits of the former natural products linked to the C-terminus di- and tripeptide S DNA binding domain of bleomycin $A_2$ (FIG. 16). The agents 105–111 incorporate the precursor to the CBI alkylation subunit which has been shown to function in an equivalent manner to the agents containing the preformed cyclopropane. In addition to the potentially interesting biological properties of the resulting agents, the examination of 105–111 was expected to provide further insights into the polynucleotide recognition inherent in the CC-1065/duocarmycin alkylation subunits and/or the bleomycin $A_2$ C-terminus. (FIG. 16).

Preparation of 114–116: The Non-linked CBI-based Agents. For a direct comparison with the di- and tripeptide S linked agents, the CBI agents 114–116 were prepared and incorporate the full acyl group used to join the CBI precursor to the bleomycin $A_2$ DNA binding domains. Acid-catalyzed deprotection of 112 (3.6 N HCl-EtOAc, 25° C., 30 min) followed direct coupling of 113 with ethyl oxalyl chloride (2 equiv, 3 equiv $NaHCO_3$, THF, 25° C., 2 h, 95–100%) cleanly provided 114 (FIG. 17). Similarly, direct coupling of freshly generated 113 with ethyl succinyl chloride (1 equiv, 2.5 equiv $NaHCO_3$, THF, 25° C., 1 h, 95–100%) followed by treatment of 115 with 5% aqueous $NaHCO_3$-THF (1:1, 25° C., 9 h, 79%) provided 116. Although this is illustrated in FIG. 17 with only the natural enantiomer series, both enantiomers of the agents 114–116 were prepared for comparative examination. (FIG. 17).

Preparation of 105–107: CBI Joined with Dipeptide S Employing a Rigid Dicarbonyl Linker. The first series of agents prepared include 105–107 in which the precursor to the CBI alkylation subunit was joined with dipeptide S through a rigid dicarbonyl linker (FIG. 18). Acylation of 117 with ethyl oxalyl chloride (2 equiv, DMF, 25° C., 20 h, 72%) followed by ethyl ester hydrolysis of 118 (5 equiv LiOH, 3:1:1 THF—$CH_3OH$—$H_2O$, 25° C., 2 h, 100%) and direct coupling of 119 with freshly generated 113 (1.5 equiv ECDI, DMF, 25° C., 17 h) deliberately conducted in the absence of added base cleanly provided 105. On occasions of prolonged exposure of 105 to air in the course of its purification, significant amounts of the corresponding sulfoxide 106 were isolated (20–25%) and independently characterized. This interesting variant of 105 and 107 embodies the DNA binding domain of bleomycin $A_1$, a minor constituent of the naturally occurring bleomycins. S-Methylation of 105 (100 equiv $CH_3I$, DMF, 25° C., 67 h, 100%) cleanly provided the sulfonium salt 107 (FIG. 18).

Figure 19:
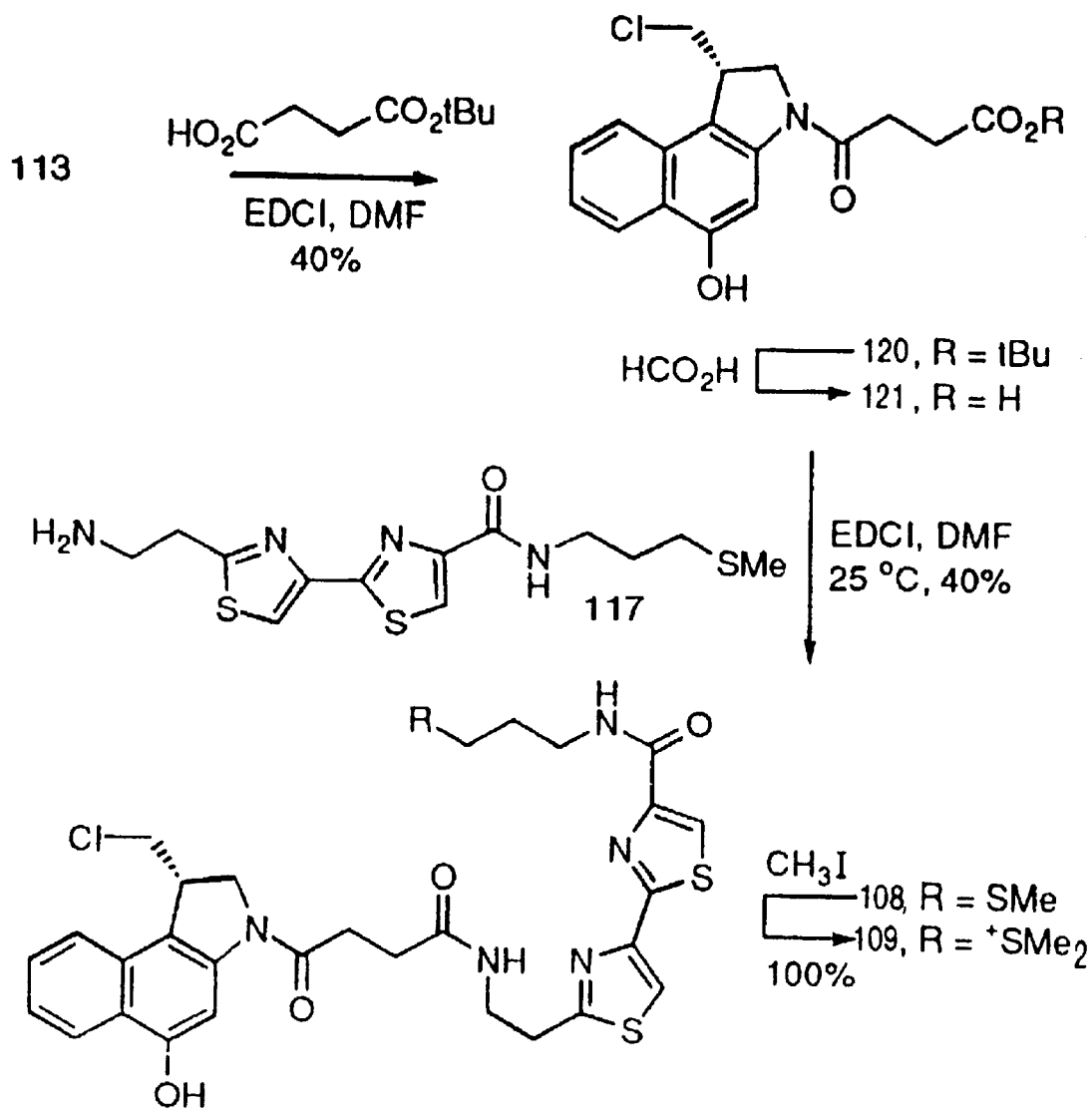
FIG. 19 illustrates the synthesis of analog 9.

Preparation of 108 and 109: CBI Joined with Dipeptide S Employing a Flexible Four Carbon Linker. In efforts to ensure that the rigid and potentially labile dicarbonyl linker of 105–107 might not be uniquely influencing the properties of the agents, 108 and 109 were prepared in which the precursor to the CBI alkylation subunit was joined with dipeptide S through a flexible four carbon linker (FIG. 19). Without optimization, coupling of freshly generated 113 with t-butyl hemisuccinate (3 equiv EDCI, DMF, 25° C., 21 h) deliberately conducted in the absence of added base provided 120. Acid-catalyzed deprotection of 120 ($HCO_2H$, 25° C., 3 h) followed by coupling of crude carboxylic acid 21 with 17 (3 equiv EDCI, DMF, 25° C., 17 h, 40%) again conducted in the deliberate absence of added base provided 108. Subsequent S-methylation of 108 (100 equiv $CH_3I$, DMF, 25° C., 144 h, 100%) cleanly provided 109.

The alternative approach of first coupling 117 with succinic anhydride (2.5 equiv, cat $CoCl_2$, 2 equiv $i-Pr_2NEt$, $CH_3CN$, 25° C., 58 h, 70%) followed by coupling of the resulting carboxylic acid with freshly generated 113 necessarily conducted in the absence of added base failed to provide 108 due to competitive internal iminolactone formation.

Figure 20:
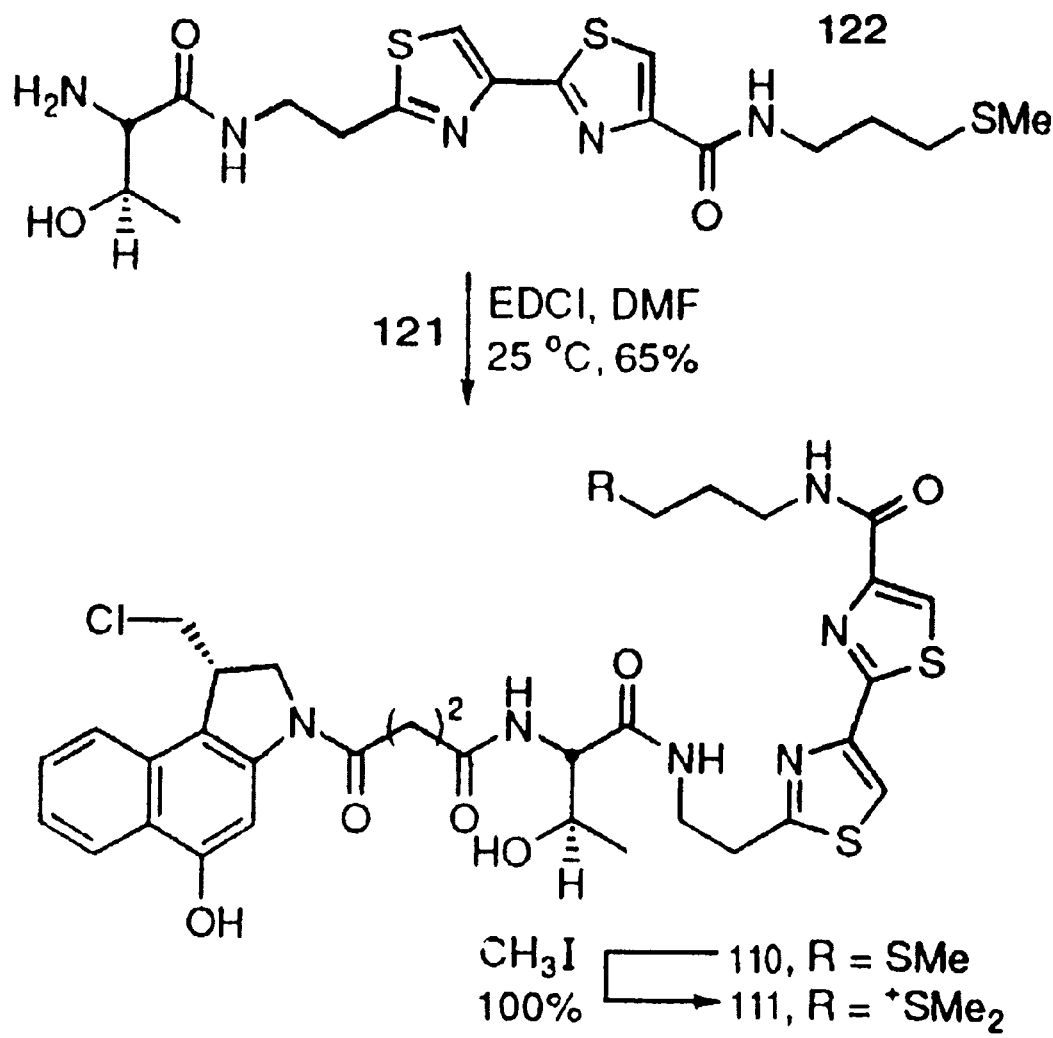
FIG. 20 illustrates the synthesis of analog 11.

Preparation of 110 and 111: CBI Joined with Tripeptide S Employing a Flexible Four Carbon Linker. The final series of agents prepared for examination include 110 and 111 in which the precursor to the CBI alkylation subunit was joined with tripeptide S through a flexible four carbon linker. Following an approach analogous to that detailed for 108 and 109, the acid-catalyzed deprotection of 120 ($HCO_2H$, 25° C., 1.5 h) and immediate coupling of 121 with 122 (2.5 equiv EDCI, 1.1 equiv HOBt, 25° C., 47 h, 65%) cleanly provided 110 (FIG. 20). Subsequent S-methylation of 110 (100 equiv $CH_3I$, DMF, 25° C., 88 h, 100%) cleanly provided 111.

Figure 22:
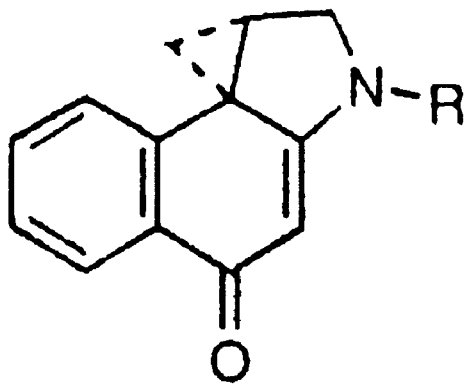
FIG. 22 illustrates natural enantiomers of 115 and 116 exhibiting low nM cytotoxic activity (5–6 nM IC$_{50}$, L1210) and are among the most potent simple derivatives disclosed to date, cf. 123–127.

In Vitro Cytotoxic Activity. Summarized in FIG. 21 is the L1210 cytotoxic activity of the agents 105–111, the comparison samples 114–116 of CBI acylated with the linkers only, and a representative range of additional comparison agents including the natural products 1–3. The comparison agents 114–16 exhibited properties consistent with past observations in which the simple N-acyl CBI derivatives exhibited cytotoxic activity in the 200–5 nM range approximately $10^3$–$10^4\times$ less potent than the natural products or the more advanced CBI-based analogs and the natural enantiomers were found to be 2–50× more potent than the corresponding unnatural enantiomers. Analogous to prior observations, no distinctions were observed between the ring opened precursor 115 and the corresponding agent 116 containing the cyclopropane. Interestingly, the natural enantiomers of 115 and 116 exhibited low nM cytotoxic activity (5–6 nM $IC_{50}$, L1210) and are among the most potent simple derivatives disclosed to date, cf. 123–127 (FIG. 22).

In sharp contrast, the agents 105–111 incorporating the di- or tripeptide S DNA binding domain of bleomycin $A_2$ linked to the agents 114–116 exhibited much lower cytotoxic activity typically being $10^2$–$10^3\times$ less potent than 114–116 themselves and $10^5$–$10^6\times$ less potent than the natural products. Only the two enantiomers of 105 approached the cytotoxic potency of 114, its corresponding CBI building block, and its structure represents that of the series which incorporates the least essential components of the bleomycin $A_2$ DNA binding domain. The remainder exhibited substantially diminished properties.

Figure 23:
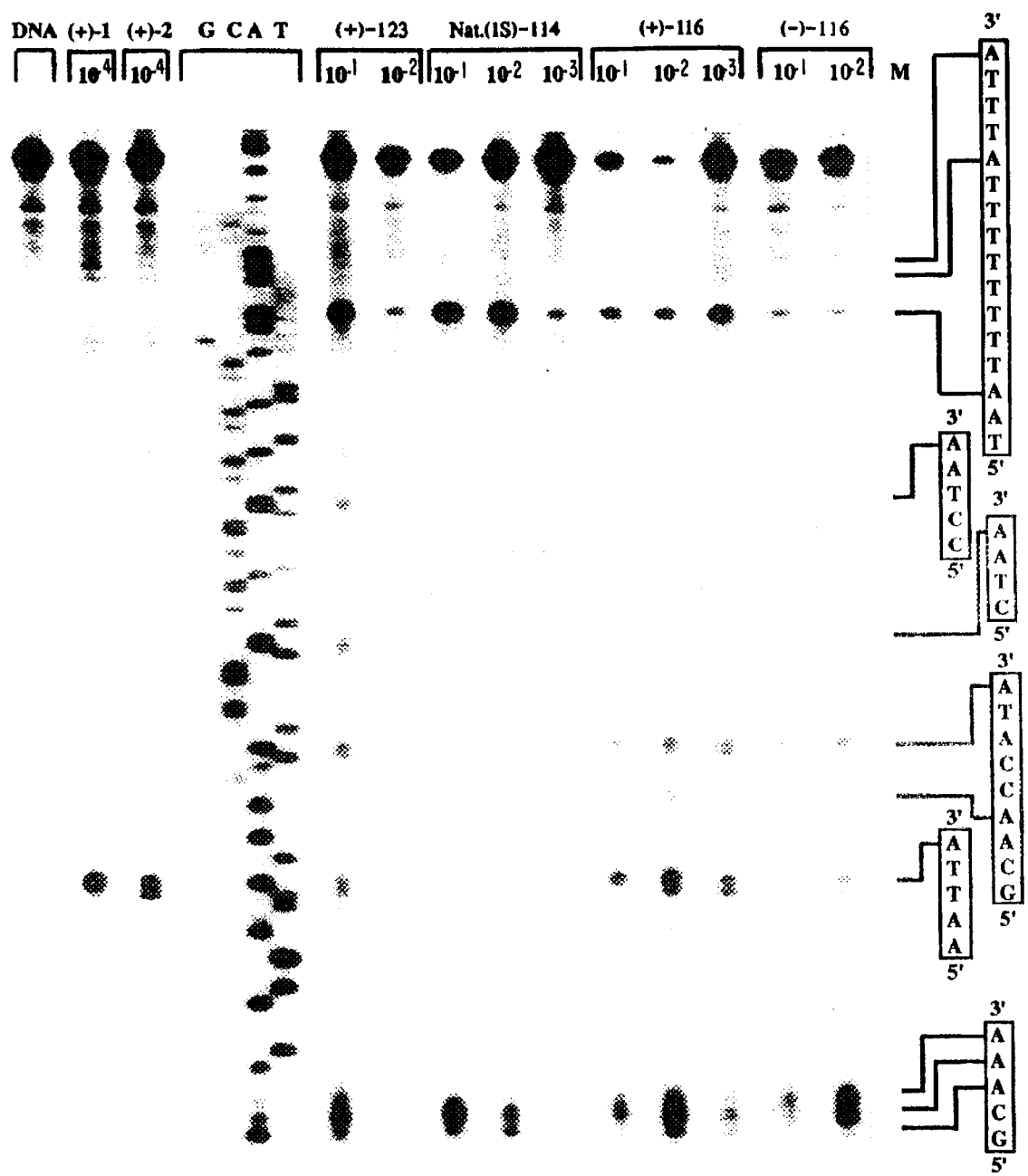
FIG. 23 illustrates thermally-induced strand cleavage of double-stranded DNA (SV40 DNA fragment, 144 bp, nucleotide no. 5238-138, clone w794) after 72 h incubation of agent with DNA at 37° C. followed by removal of unbound agent, and 30 min incubation at 100° C., 8% denaturing PAGE, and autoradiography: lane 1, control DNA; lane 2, (+)-CC-1065 (1, 1×10$^{-6}$ M); lane 3, (+)-duocarmycin SA (2, 1×10$^{-6}$ M); lanes 4–7, Sanger G, C, A, and T sequencing reactions; lanes 8 and 9, (+)-N-BOC-CBI ((+)-123, 1×10$^{-1}$ and 1×10$^{-2}$ M); lanes 10–12, (1S)-114 (1×10$^{-1}$ to 1×10$^{-3}$ M); lanes 13–15, (+)-116 (1×10$^{-1}$ and 1×10$^{-3}$ M); lanes 16 and 17, (−)-116 (1×10$^{-1}$ and 1×10$^{-2}$ M).

DNA Alkylation Properties. The agents 114–116 exhibited DNA alkylation properties analogous to those of N-BOC-CBI (FIG. 23). Within w794 DNA, the agents alkylated DNA at concentrations of $10^{-1}$–$10^{-3}$ M which is $10^3$–$10^4\times$ less efficient than 1–3 and did so with alkylation of the same sites (5'-AA>5'-TA) independent of the absolute configuration. Analogous to their relative cytotoxic potencies, the natural enantiomers were approximately 10× more effective than the corresponding unnatural enantiomers. Further consistent with its cytotoxic properties, the natural enantiomer of 116 was 10–100× more effective at alkylating DNA than N-BOC-CBI (123) and 114 was also found to be more effective. Thus, the attached linkers did not diminish, and in fact enhanced, the DNA alkylation efficiencies.

Figure 24:
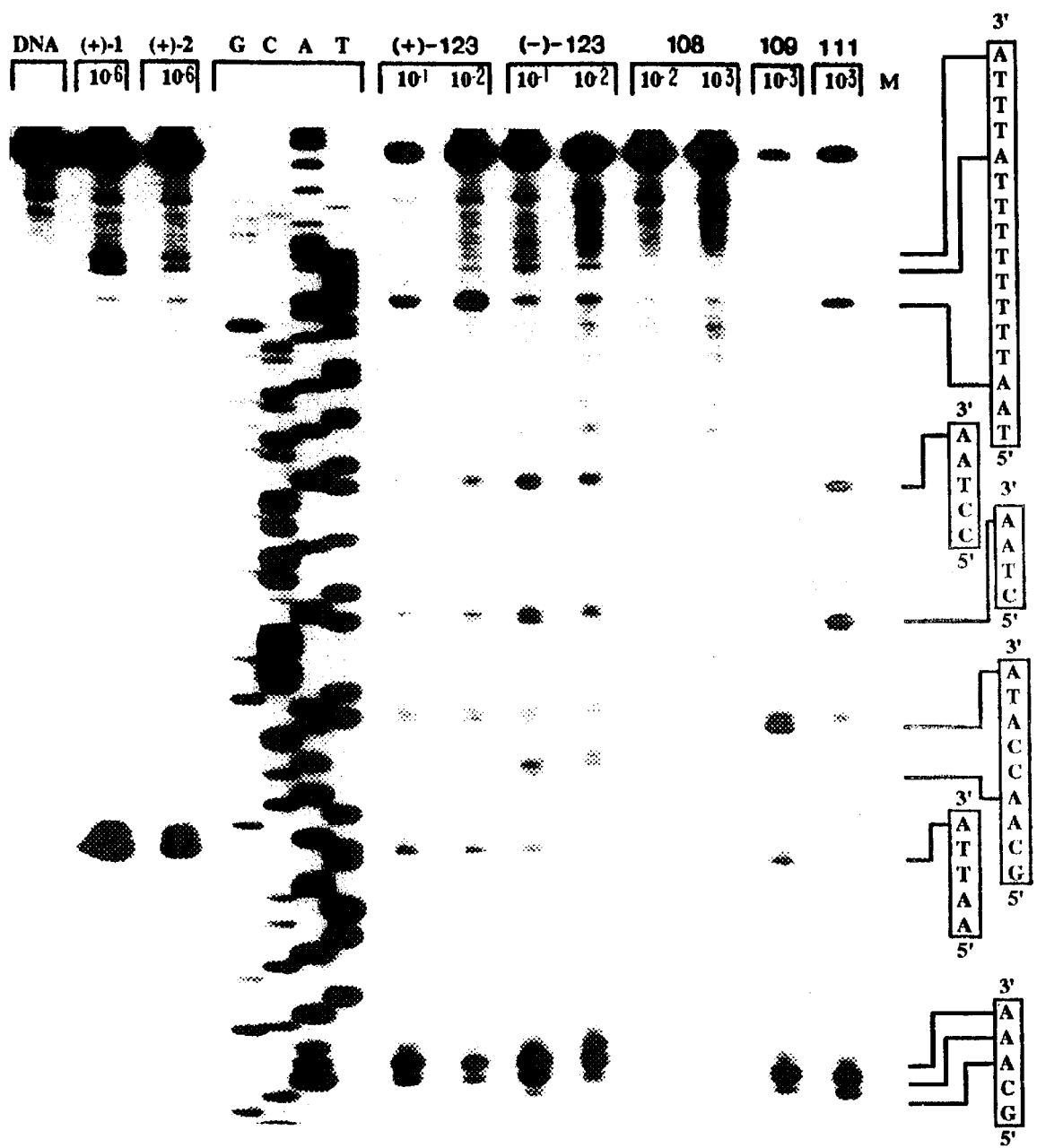
FIG. 24 illustrates thermally-induced strand cleavage of double-stranded DNA (SV40 DNA fragment, 144 bp, nucleotide no. 5238-138, clone w794) after 48 h incubation of agent with DNA at 37° C. followed by removal of unbound agent, and 30 min incubation at 100° C., 8% denaturing PAGE, and autoradiography: lane 1, control DNA; lane 2, (+)-CC-1065 (1, 1×10$^{-6}$ M); lane 3, (+)-duocarmycin SA (2, 1×10$^{-6}$ M); lanes 4–7, Sanger G, C, A, and T sequencing reactions; lanes 8 and 9, (+)-N-BOC-CBI ((+)-123, 1×10$^{-1}$ and 1×10$^{-2}$ M); lanes 10 and 11, (−)-N-BOC-CBI ((−)-123, 1×10$^{-1}$ and 1×10$^{-2}$ M); lanes 12 and 13, 108 (1×10$^{-2}$ and 1×10$^{-3}$ M); lane 14, 109 (1×10$^{-3}$ M); lane 15, 111 (1×10$^{-3}$ M).

In contrast, the first set of hybrid agents examined including 105–107 failed to provide evidence of detectable, thermally sensitive alkylation of DNA even under vigorous reaction conditions (37° C., 72 h) at agent concentrations as high as $10^{-2}$ M. Analogous to the relative cytotoxic activity of the agents, the attachment of the CBI alkylation subunit to the bleomycin bithiazole C-terminus using the dicarbonyl linker resulted in diminished adenine N3 alkylation characteristic of 1–3. Similarly, the methyl sulfides 108 and 110 incorporating the flexible 4 carbon linker and the unmethylated di- and tripeptide S C-terminus, respectively, failed to alkylate DNA at concentrations of $10^{-3}$ M or lower and failed to produce thermally labile adducts. This is illustrated nicely in FIG. 24 with 108 where both enantiomers of N-BOC-CBI alkylate DNA at $10^{-2}$ M but no reaction is observed for 108. Only the agents 109 and 111 incorporating the flexible 4 carbon linker and the fully functionalized di- and tripeptide S C-terminus provided a thermally labile DNA alkylation reaction but did so in a manner only slightly more effective than 116. Moreover, detectable alkylation required vigorous reaction conditions (37° C., 48–72 h), prolonged reaction times, and proceeded with a selectivity (5'-AA, 5'-TA) that was analogous to that observed with N-BOC-CBI and 116. Thus, while exhibiting properties better than 105–107 or 108 and 110, the agents were only comparable to 115 and 116. Thus, their DNA alkylation efficiency was not significantly enhanced by their attachment to the C-terminus of bleomycin $A_2$ and their inherent DNA alkylation selectivity was not altered.

Incubation of the agents with calf thymus DNA under comparable conditions (37° C., 48–72 h, 1:51 agent:base-pair ratio) followed by recovery of unreacted agent by extraction (105, 106, 108, and 110) or DNA precipitation (109 and 111) confirmed that the observations are the result of a diminished DNA alkylation capability and not attributable to alternative DNA alkylation reactions that fail to provide thermally labile adducts (FIG. 25). Both enantiomers of 105 and 106 and the natural enantiomers of 108 and 110 were recovered nearly quantitatively from the DNA reaction mixtures even under prolonged vigorous reaction conditions (37° C., 72 h) conducted in the presence of excess DNA. Only 109 and 111 exhibited perceptible covalent attachment to the calf thymus DNA consistent with their modest DNA alkylation capabilities observed in the sequencing studies.

Thus, the attachment of the CBI alkylation subunit characteristic of CC-1065 and the duocarmycins to the C-terminus DNA binding domain of bleomycin $A_2$ did not lead to enhancement of the DNA alkylation or cytotoxic properties of the resulting hybrid agents and, in some instances, lead to diminished properties. This is in sharp contrast to the impact of the conventional DNA binding domains of CC-1065 and related analogs which leads to a $10^3$–$10^4\times$ enhancement in DNA alkylation efficiencies and cytotoxic potencies. In addition to illustrating the important complementary nature of these two functions of DNA binding and subsequent DNA alkylation in the natural products and their closely related analogs, the results have significant implications on the behavior of both bleomycin $A_2$ and CC-1065/duocarmycin. The most obvious is that the C-terminus of bleomycin $A_2$ does not appear to behave as an AT-rich minor groove binding domain analogous to the right-hand subunits of CC-1065 and the duocarmycins. Although minor groove binding has been suggested to be a productive DNA binding mode for bleomycin $A_2$ and even suggested to be responsible for the sequence selective polynucleotide recognition, the results are more consistent with expectations resulting from bithiazole intercalative binding. This mode of binding would not be expected to selectively deliver the alkylation subunit to the DNA minor groove and might, in fact, inhibit such delivery. In addition, the alkylation selectivity of 109 and 111 was identical to that of N-BOC-CBI (123) and 116 which lack the bleomycin $A_2$ DNA binding domain and all were much less selective than 1–3. Thus, the attachment of the DNA binding domain of bleomycin $A_2$ did not alter the DNA alkylation selectivity of the CBI alkylation subunit (5'-AA>5'-TA) in a manner that would reflect any sequence selective binding by this component of bleomycin nor did it enhance the selectivity in manner that approaches the five base-pair AT-rich alkylation selectivity of 1.

EXAMPLE 3

Synthesis and Properties of Fluorocyclopropane Analogs of the Duocarmycins Incorporating the 9, 9-Difluoro-1,2,9,9a-tetrahydrocyclopropa[c]benzo[e] indol-4-one ($F_2$CBI) Alkylation Subunit The synthesis of 9,9-difluoro-1,2,9,9a-tetrahydrocyclopropa[c]benz[e]indol-4-one ($F_2$CBI), a difluorocyclopropane analog of the CC-1065 and duocarmycin alkylation subunits which represents the first such agent containing substitution of the reactive center in the natural products, is described. The core structure of $F_2$CBI was prepared by an intramolecular metal carbenoid insertion reaction into a 1,1-difluoroalkene (74%) employing a p-quinonediazide and its incorporation into $F_2$CBI-TMI (233) provided a key analog of the duocarmycins. A study of the solvolysis of N-BOC-$F_2$CBI (219) revealed that introduction of the difluorocyclopropane substitution increased the reactivity 500× without altering the inherent regioselectivity which occurred with nucleophilic addition to the difluoro substituted C9 cyclopropane carbon. A single-crystal X-ray structure analysis of 217 and its comparison with the X-ray structures of CBI and related agents beautifully reveal the structural origin of the difluoro substitution effects on the reactivity and regioselectivity of the cyclopropane cleavage reaction. The cyclopropane C—$CF_2$—C bond angle is expanded and the carbon-carbon bond opposite the difluoro substitution is lengthened to accommodate the preferentially compressed exocyclic F—C—F bond angle introducing additional strain energy. Consistent with this increased reactivity and following trends established to date, the agents were found to be 500–1000× less cytotoxic than the corresponding CBI derivative lacking the difluorocyclopropane substitution. Similarly, the gem difluoro substitution had no perceptible effect on the DNA alkylation selectivity of the agents and they were found to undergo the characteristic adenine N3 addition to the C9 cyclopropane carbon, but did so with a reduced (675–725×) efficiency following the cytotoxicity and stability correlations.

In this example, we detail the synthesis and examination of 9,9-difluoro-1,2,9,9a-tetrahydrocyclopropa[c]benzo[e] indol-4-one ($F_2$CBI), a difluoro substituted cyclopropane analog of the alkylation subunits of 1–3 which represents the first such analog containing substitution or functionalization of the reactive center in the natural products (FIG. 26). Typically, the noncongruent inductive electron-withdrawing properties of a fluorine substituent and its resonance stabilizing properties combine to reinforce a resonance stabilized reaction regioselectivity with diminished reactivity when compared to a substrate bearing a hydrogen substituent. Complementing these properties, the size of a fluorine substituent is sufficiently similar to that of hydrogen that it can be regarded as a sterically larger but nonobtrusive substitution for hydrogen. However, fluorine substitution of a cyclopropane has been shown to impart unique effects different even from those of other halogens. Experimentally, it has been shown to increase ring strain by 4.5–5.0 kcal/mol per fluorine, it significantly weakens the bond opposite the carbon bearing the fluorine substituent, and it has been suggested to slightly strengthen or weaken the adjacent bonds. Similarly, geminal difluoro substitution of cyclopropane has been experimentally estimated to weaken the bond opposite the $CF_2$ by 9–10 kcal/mol but imparts much less effect on the adjacent bonds weakening them by 0–2 kcal/mol. Consequently, it was unclear whether the gem difluoro substitution of the CBI cyclopropane would alter or enhance the stereoelectronically-controlled reaction regioselectivity for nucleophilic ring opening and, a priori, it was not clear whether this substitution would enhance or diminish the inherent electrophilic functional reactivity. Consequently, we have prepared the $F_2$CBI alkylation subunit in efforts to examine the effect of the difluoro substitution on the structure, reactivity, and reaction regioselectivity of the agent and its impact on the biological properties of the resulting analogs of 1–3.

Figure 27:
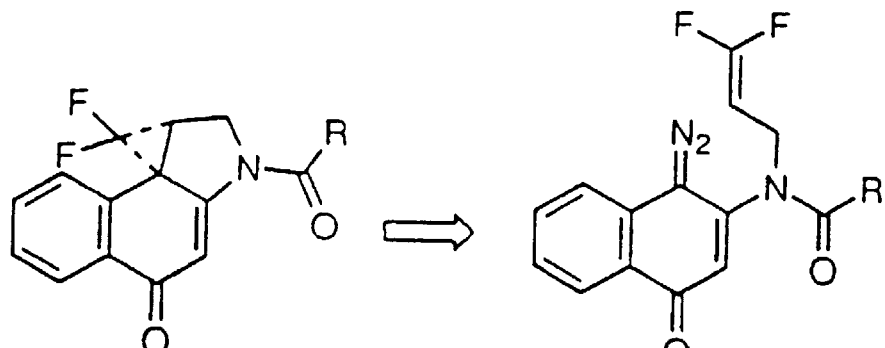
FIG. 27 illustrates a retrosynthesis of $F_2CBI$ employing a quinonediazide with a key intramolecular metal carbenoid insertion into a 1,1-difluoroalkene.

Synthesis N-Acetyl-$F_2$CBI, N-BOC-$F_2$CBI, and $F_2$CBI. The synthesis of the $F_2$CBI nucleus is shown in FIG. 27 wherein the retrosynthesis of the alkylation subunit of CC-1065 employing a quinonediazide and a key intramolecular metal carbenoid insertion into a 1,1-difluoroalkene is shown.

Figure 28:
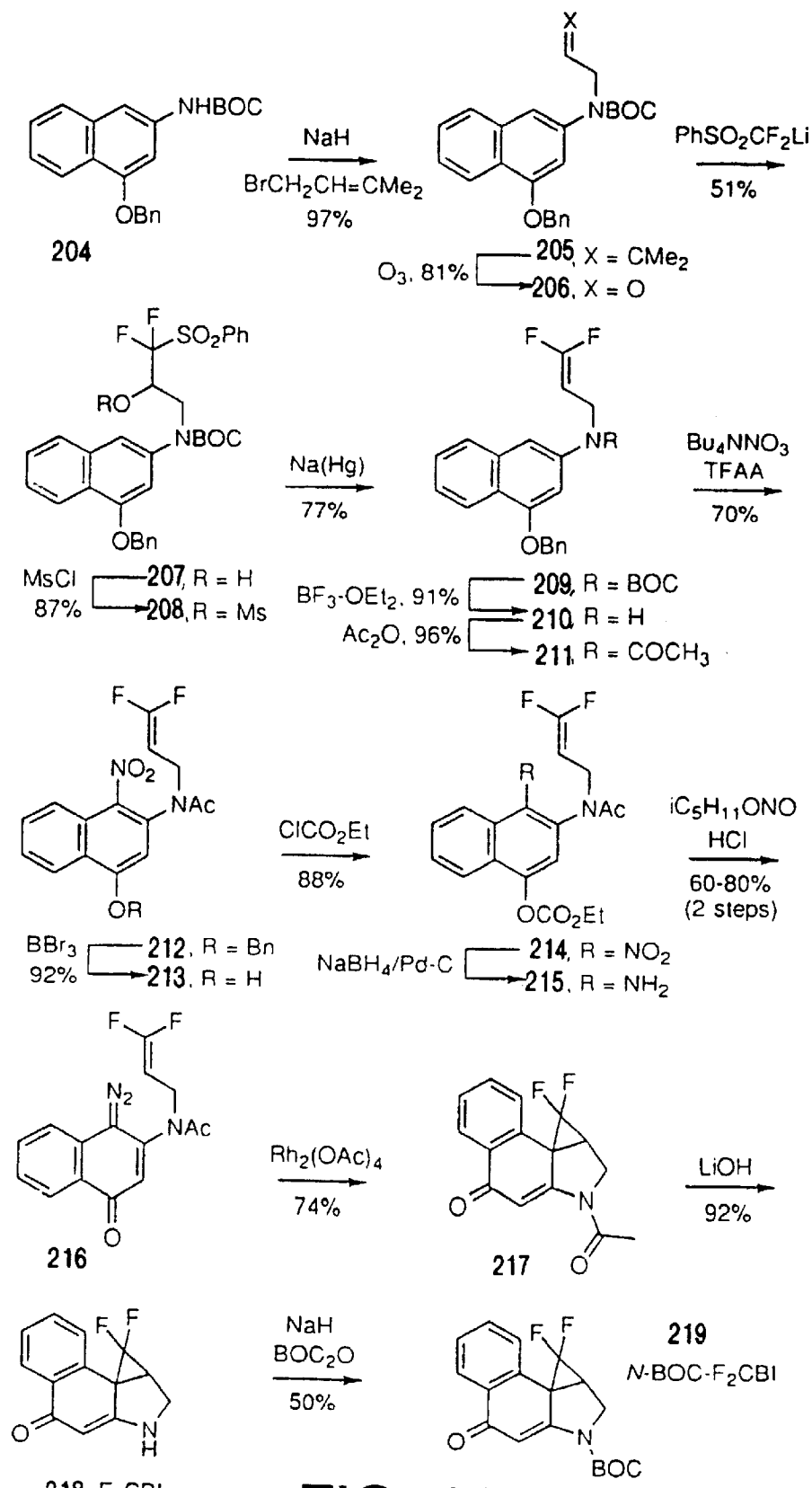
FIG. 28 illustrates the synthesis of advanced intermediate 219.

Alkylation of the sodium salt of 204 (1.3 equiv NaH, DMF, 0–25° C., 14 h, 97%; Boger, D. L.; Yun, W.; Teegarden, B. R. *J. Org. Chem.* 1992, 57, 2873) with 1-bromo-3-methyl-2-butene cleanly provided 205 (FIG. 28). Low-temperature ozonolysis of 205 and subsequent reductive workup ($Me_2S$) of the crude ozonide under carefully monitored reaction conditions effectively provided the aldehyde 206 although short extensions of the reaction time beyond those detailed led to further oxidation. The difluoroalkene was introduced following a in three-step protocol developed by Sabol and McCarthy. Low-temperature generation of α-lithio phenyl difluoromethylsulfone (LHMDS, THF-HMPA, −78° C.) in the presence of 206 provided the β-hydroxysulfone 207 (51%; Stahly, G. P. *J. Fluorine Chem.* 1989, 43, 53. Miller, T. G.; Thanassi, J. W. *J. Org. Chem.* 1960, 25, 2009) in a reaction that proved difficult to optimize. Efforts to generate the α-lithiosulfone and subsequently add the aldehyde 206 failed to provide 207 in competitive conversions due to the instability of the reagent. Ultimately, it proved most convenient to conduct the reaction with the in situ generation of the α-lithiosulfone in the presence of the aldehyde 206 which led to competitive enolization and ultimately recovery of the substrate (20–40%). Because of the chromatographic properties of 206 and 207, a careful chromatography of the crude reaction mixture or subsequent conversion of 207 to the mesylate 208 followed by a quick plug chromatography was employed to recover unreacted 206 which could be recycled providing overall conversions approaching 75%. This improved what turned out to be the only problematic step in the synthesis. Conversion of 207 to the mesylate 208 (2 equiv MsCl, 10 equiv Et$_3$N, 3.5 h, 87%) followed by reductive elimination effected by treatment with 5% Na(Hg) (6 equiv, 4 equiv Na$_2$HPO$_4$, CH$_3$OH, 0° C., 1 h, 77%) provided the key difluoroalkene 209. This latter reaction was optimal when the ratio of substrate:Na$_2$HPO$_4$:Na(Hg) was 1:4:6 and significant amounts of the desulfonylated mesylate (20–40%) was isolated when the number of equivalents of Na(Hg) exceeded 10 equiv. The tosylate of 207 (Stahly, G. P. *J. Fluorine Chem.* 1989, 43, 53. Miller, T. G.; Thanassi, J. W. *J. Org. Chem.* 1960, 25, 2009) behaved similarly and provided good conversions to 209 when treated with Na(Hg) under the optimized conditions. Efforts to promote the reductive elimination of 208 with SmI$_2$ was not successful with our substrate and limited efforts to promote the reductive elimination with 207 itself employing Na(Hg) were not productive (FIG. 28).

Alternative olefination procedures for introduction of a terminal difluoroalkene including diethyl (difluoromethyl) phosphonate, diphenyl difluoromethylphosphine oxide, and related Wittig reagents failed to provide a competitive route to 109. Similarly, attempts to generate 109 directly from 104 by S$_N$2' reaction of its sodium or lithium salt with 3,3,3-trifluoropropene, analogous to reported reactions with stronger nucleophiles, provided only recovered starting materials (Obayashi, M.; Ito, E.; Matsui, K.; Kondo, K. *Tetrahedron Lett.* 1982, 23, 2323. Obayasi, M.; Kondo, K. *Tetrahedron Lett.* 1982, 23, 2327; Edwards, M. L.; Stemerick, D. M.; Jarvi, E. T.; Mattews, D. P.; McCarthy, J. R. *Tetrahedron Lett.* 1990, 31, 5571. Moore, W. R.; Schatzman, G. L.; Jarvi, E. T.; Gross, R. S.; McCarthy, J. R. *J. Am. Chem. Soc.* 1992, 114, 360; Fuqua, S. A.; Duncan, W. G.; Silverstein, R. M. *J. Org. Chem.* 1965, 30, 1027. Naae, D. G.; Kesling, H. S.; Burton, D. J. *Tetrahedron Lett.* 1975, 3789. Naae, D. G.; Burton, D. J. *J. Fluorine Chem.* 1971, 1, 123. Naae, D. G.; Burton, D. *J. Synth. Commun.* 1973, 3, 197. Burton, D. J. *J. Fluorine Chem.* 1983, 18, 339. Burton, D. J.; Kesling, H. S.; Naae, D. G. *J. Fluorine Chem.* 1981, 18, 293. Wheaton, G. A.; Burton, D. J. *J. Org. Chem.* 1983, 48, 917. Matsuda, A.; Itoh, H.; Takenishi, K.; Susuki, T.; Ueda, T. *Chem. Pharm. Bull.* 1988, 36, 945. Fried, J.; Kittisopikul, S.; Hallinan, E. A. *Tetrahedron Lett.* 1984, 25, 4329. For recent and potentially useful alternatives: Dolbier, W. R., Jr.; Ocampo, R. *J. Org. Chem.* 1995, 60, 5378. Kim, K.-I.; McCarthy, J. R. *Tetrahedron Lett.* 1996, 37, 3223; Kendrick, D. A.; Kolb, M. *J. Fluorine Chem.* 1989, 45, 265. Begue, J.-P.; Bonnet-Delpon, D.; Rock. M. H. *Tetrahedron Lett.* 1995, 36, 5003).

Figure 29:
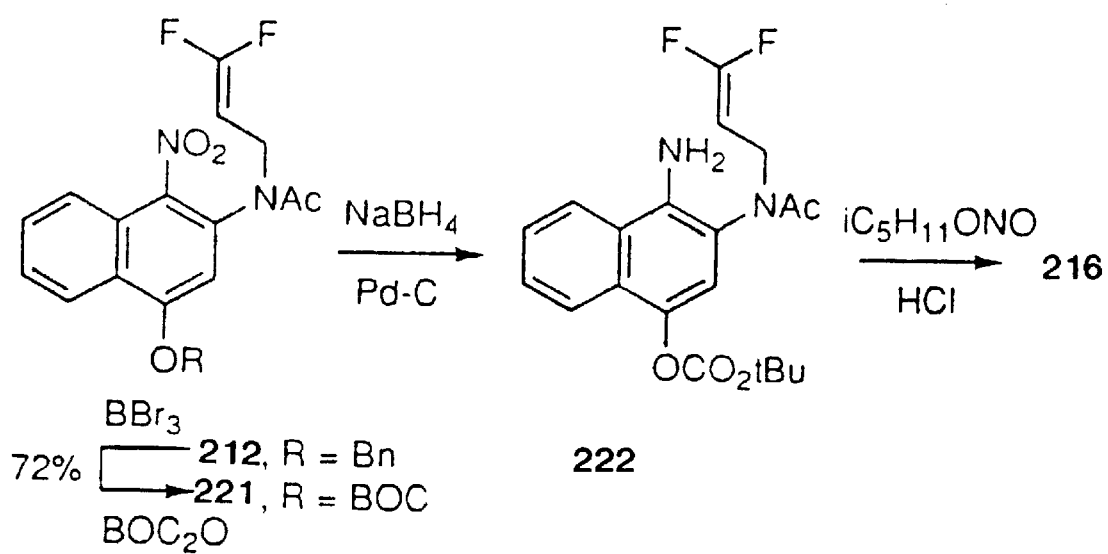
FIG. 29 illustrates the synthesis of advanced intermediates 216 and 221.

Introduction of the quinonediazide required deprotection of the benzyl ether and, preferentially, the reintroduction of an acid labile protecting group such that its removal would occur subsequent to acid-catalyzed diazonium salt formation but still be stable to the conditions of reduction of the aryl nitro group to an aryl amine preventing oxidation to a p-quinone monoimine. These criteria were unable to be fulfilled with the N-BOC protecting group in place. Therefore, the N-BOC group was replaced with an N-acetyl group and nitration of 211 effected by treatment with CF$_3$CO$_2$NO$_2$ (2.5–3.5 equiv Bu$_4$NNO$_3$, 0.002 equiv TFAA, CH$_2$Cl$_2$, 25° C., 16–32 h, 70%) cleanly provided 212 derived from C-4 nitration with only the occasional generation of a small amount of the isomeric C-2 nitration product (ca. 10%). The benzyl ether was cleaved (2.0 equiv BBr$_3$, CH$_2$Cl$_2$, -78° C., 30 min, 92%) to provide 213 and the phenol was reprotected as the ethylcarbonate 214 (88%). Nitro reduction in the presence of the difluoroalkene was accomplished by treatment with NaBH$_4$/5% Pd—C (H$_2$O—CH$_3$OH, 0° C., 15 min). Without purification or storage, the amine 215 was converted directly to the key quinonediazide 216 by treatment with i-C$_5$H$_{11}$ONO (catalytic 4 M HCl—CH$_3$OH, -30° C., 16 h) under conditions where acid-catalyzed cleavage of the carbonate leads to conversion of the intermediate diazonium salt to 216 directly. Using this procedure, yields for the overall conversion of 214 to 216 as high as 80% were obtained with typical conversions being 60%. The only significant byproduct generated in this sequence was the fused benzimidazole 220a and its formation could be minimized by use of short reduction periods (15 min) coupled with not storing or purifying the free amine 215 prior to its use. The use of sufficient amounts of strong acid in the diazotization reaction also appeared to diminish its formation. In the further optimization of this sequence, it was established that the conversions steadily increased as the amount of i-C$_5$H$_{11}$ONO was increased and finally employed as solvent, increased as the reaction time was extended from 1 to 3 h and finally 17 h, and proved optimal if the strong acid employed in the diazotization reaction was added following the i-C$_5$H$_{11}$ONO. Attempts to employ alternative reduction conditions (Zn, CaCl$_2$, 95% EtOH) were unsuccessful with either 213 or 214 and provided recovered starting materials (FIG. 29).

The use of the tert-butylcarbonate 221 (FIG. 29) was also explored and was found to provide comparable conversions to either 222 or 216 but offered no distinctions or advantages over the use of the ethylcarbonate 214.

Metal carbenoid generation and insertion into the difluoroalkene was effectively accomplished by treatment of 216 with Rh$_2$(OAc)$_4$ (0.1–0.2 equiv, toluene, reflux, 0.5 h, 74%) protected from the light and smoothly provided N-acetyl-F$_2$CBI (217), FIG. 28. Similar, but less consistent conversions were observed with Cu(acac)$_2$ catalysis (58%) and, in both cases, the conversions diminished at lower reaction temperatures and seemed to drop as the amount of catalyst was increased beyond 0.2 equiv. Hydrolysis of 217 by simple treatment with LiOH (1.2 equiv, CH$_3$OH, -10° C., 15 min, 92%) cleanly provide F$_2$CBI (218). Conversion of 218 to N-BOC-F$_2$CBI (219) was accomplished by NaH deprotonation and subsequent reaction with BOC$_2$O.

Figure 30:
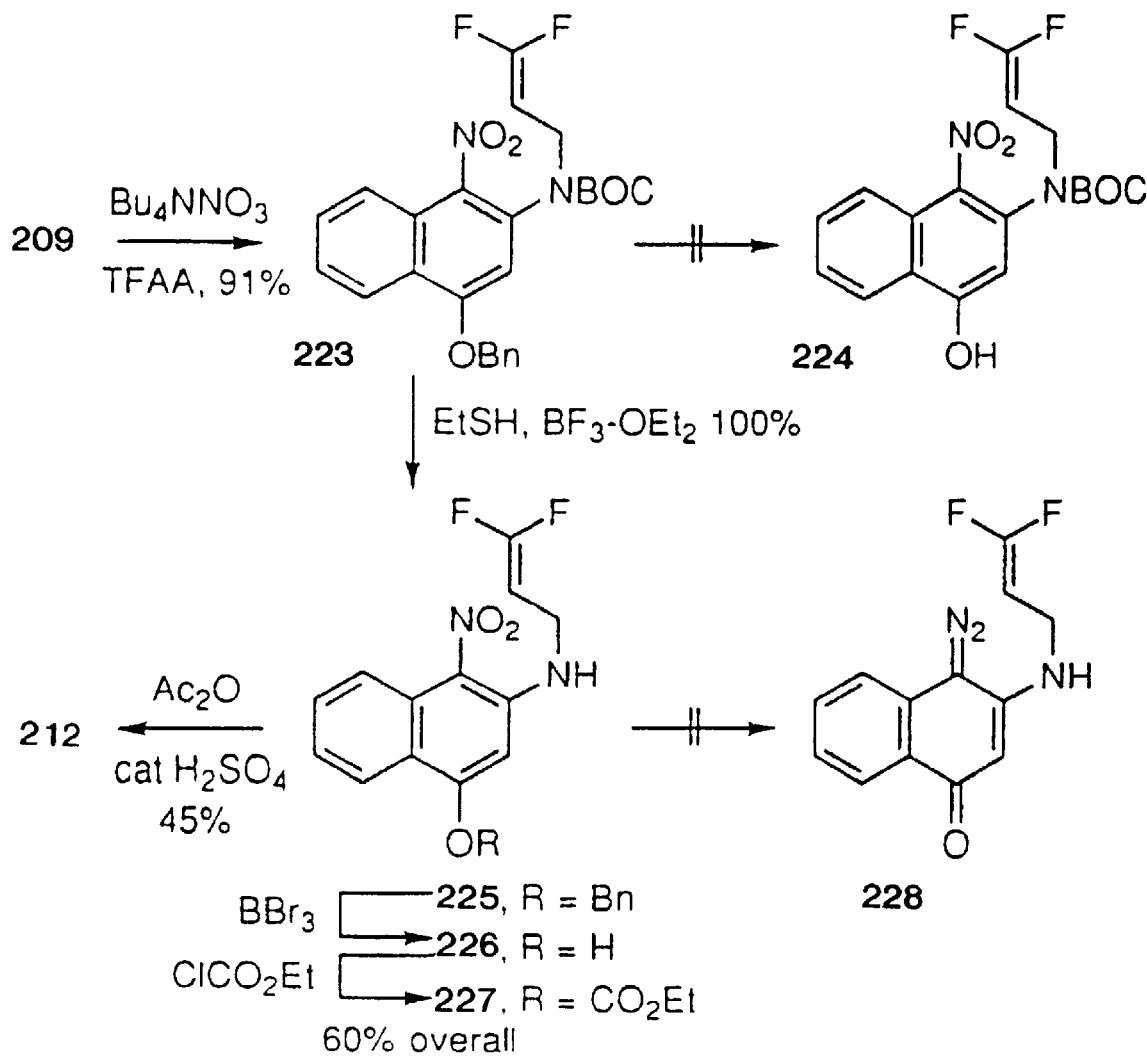
FIG. 30 illustrates the synthesis of analog 227.

Preparation of F$_2$CBI-TMI (233). The advanced analog of 224 of the duocarmycins was prepared by deprotonation of 218 (1.1 equiv NaH, DMF, 25° C.) followed by reaction with 223 (DMF, 1 h, 25° C., 45%; Muratake, H.; Abe, I.; Natsume, M. *Tetrahedron Lett.* 1994, 35, 2573; 64% based on recovered 218); FIG. 30

Solvolysis: Reactivity. Two fundamental characteristics of the alkylation subunits have proven important in the studies to date. The first is the stereoelectronically-controlled acid-catalyzed ring-opening of the cyclopropane which dictates preferential addition of a nucleophile to the least substituted cyclopropane carbon. With the CBI series of modified alkylation subunits where this stereoelectronic alignment of the C8b-C9 bond is nearly optimized, exclusive (≧20:1) addition to the C9 center with cleavage of the C8b-C9 bond is observed. The second characteristic is the relative-rate of solvolysis which has been found to accurately reflect the functional reactivity of the agents and to follow a well-defined direct relationship between solvolysis (functional) stability and in vitro cytotoxic potency. Thus, the impact of the difluorocyclopropane substitution on the reactivity and reaction regioselectivity of CBI was examined.

Figure 31A:
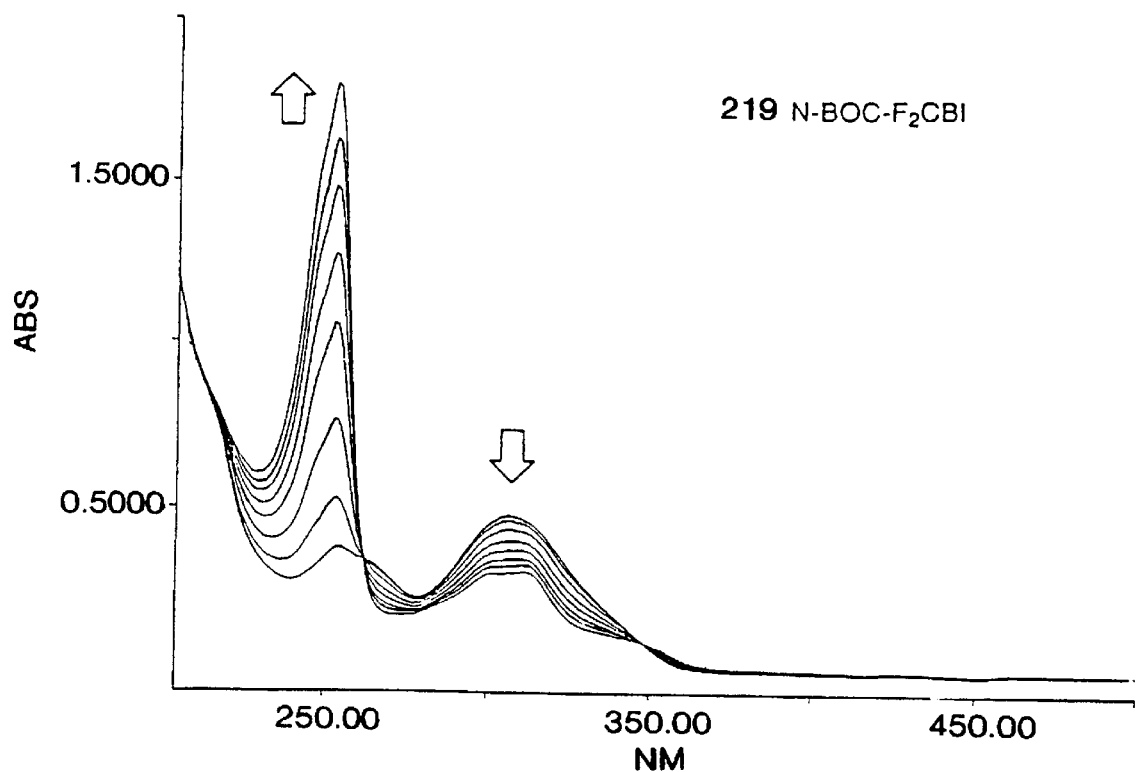
FIG. 31 illustrates a solvolysis study (UV spectra) of N-BOC-$F_2$CBI (219, top) and $F_2$CBI (218, bottom) in 50% $CH_3OH$-aqueous buffer (pH 3.0, 4:1:20 (v/v/v) 0.1 M citric acid, 0.2 M $Na_2HPO_4$, and $H_2O$, respectively). The spectra were recorded at regular intervals and only a few are shown for clarity. Top: 1, 0 min; 2, 2 min; 3, 5 min; 4, 11 min; 5, 17 min; 6, 25 min; 7, 33 min; 8, 48 min. Bottom: 1, 0 h; 2, 0.5 h; 3, 1.5 h; 4, 2.5 h; 5, 3.5 h; 6, 4.5 h; 7, 5 h; 8, 5.5 h.
Figure 31B:
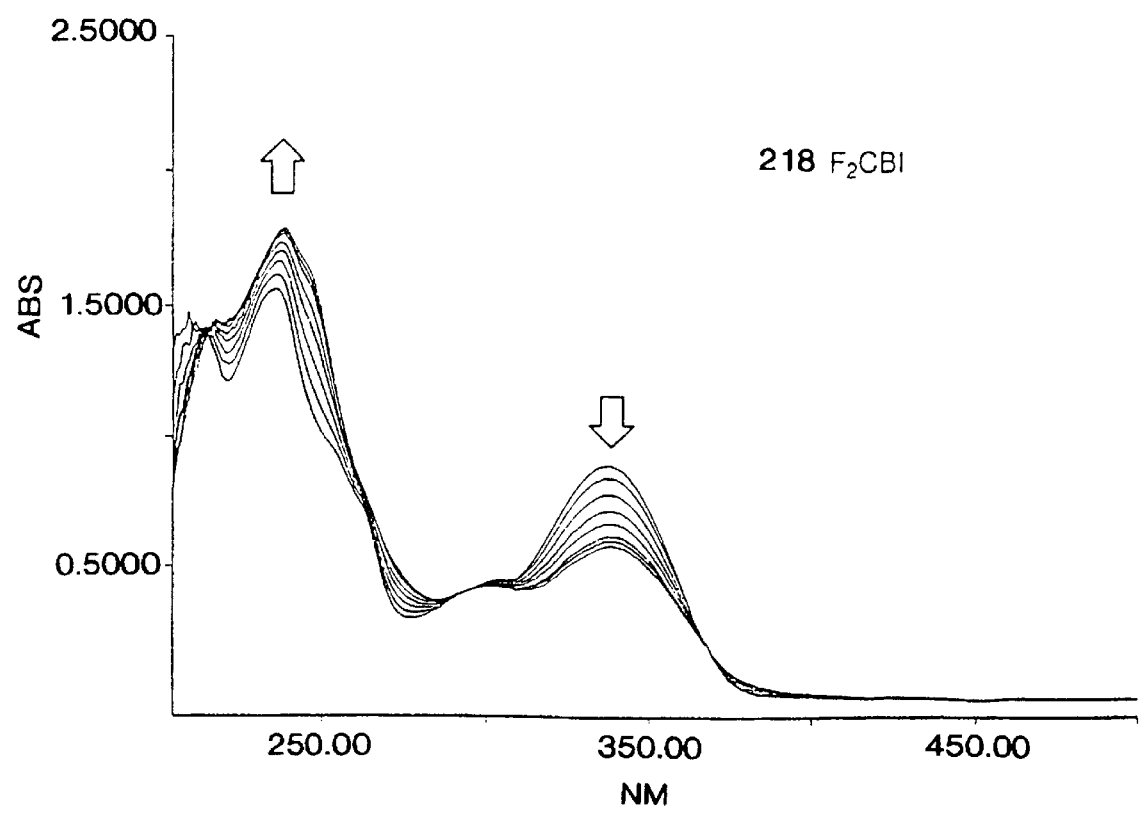

The reactivity of 217–219 was assessed by following the solvolysis spectrophotometrically by UV at both pH 3 (50% $CH_3OH$-buffer, buffer=4:1:20 (v/v/v) 0.1 M citric acid, 0.2 M $Na_2HPO_4$, $H_2O$) and pH 7 (1:1 $H_2O$—$CH_3OH$) measuring both the disappearance of the long-wavelength absorption band of the $F_2CBI$ chromophore and the appearance of a short-wavelength absorption band attributable to the ring open products (FIG. 31).

N-BOC-$F_2CBI$ (219) proved to be remarkably reactive toward acid-catalyzed solvolysis. At pH 3, it exhibited a half life of 0.26 h (k=$7.05 \times 10^{-4}$ $s^{-1}$) and proved to be approximately 500× more reactive than N-BOC-CBI ($t_{1/2}$=133 h, k=$1.45 \times 10^{-6}$ $s^{-1}$) which lacks only the two fluorine substituents. Moreover, 219 is among the most reactive of the modified alkylation subunits studied to date. At pH 7 where N-BOC-CBI is stable, it also underwent rapid solvolysis ($t_{1/2}$=2.33 h, k=$8.27 \times 10^{-5}$ $s^{-1}$). N-acetyl-$F_2CBI$ (217) and $F_2CBI$ (218) were also examined and the results are summarized in FIG. 32. No substantial distinction in the reactivity of 217 and 219 was observed while 218 proved significantly more stable ($t_{1/2}$=4.2 h, k=$4.54 \times 10^{-5}$ $s^{-1}$ at pH 3). This is analogous to prior observations and 218 proved to be approximately 220× more reactive than CBI.

Solvolysis: Regioselectivity. Treatment of both 217 and 219 with catalytic $CF_3SO_3H$ (0.1 equiv) in $CH_3OH$ (0° C.) rapidly and cleanly provided a single characterizable product 225 (30 min, 90%) or 226 (10 min, 79%), FIG. 33. Spectroscopically, this could be shown to be derived from addition of $CH_3OH$ to the difluoro substituted C9 cyclopropane carbon analogous to the normal solvolysis observed with N-BOC-CBI and related agents. $^{19}$F NMR spectra of both 225 and 226 exhibited a single fluorine resonance, demonstrating that both fluorines are magnetically equivalent. The ring expansion regioisomer possesses diastereotopic fluorines which would be magnetically nonequivalent. Furthermore, the $^1H$-$^{13}C$ HMBC NMR spectrum of 226 established the carbon-carbon connectivity of C1 (δ51.0) with the $CF_2$ carbon (δ50.3, t) and C9b (δ125.0). No connectivity between the key $CF_2$ carbon (δ50.3, t) and C9b (δ125.0) was detected as required of the ring expansion regioisomer. This was unambiguously established by conducting the solvolysis in THF-$H_2O$ catalyzed by $CF_3SO_3H$ (0.12 equiv) which cleanly provided 227 (18 h, 85%), FIG. 33. Nucleophilic addition under basic conditions leads to preferential reaction at the N-acetyl substituent as evidenced by the clean hydrolysis of 217 to provide 218 (FIG. 28).

Although it is possible that minor amounts of the abnormal solvolysis products may have gone undetected or decomposed under the solvolysis conditions, the studies detailed above establish that addition to the difluoro substituted C9 carbon occurs with a ≧9:1 preference. This is analogous to observations made with the CBI-based agents where exclusive (>20:1) addition to the C9 carbon is observed. Thus, the introduction of the gem difluorocyclopropane substitution did not alter the inherent regioselectivity of the stereoelectronically-controlled acid-catalyzed nucleophilic addition to the activated cyclopropane. To date, agents incorporating the CBI nucleus have exhibited the greatest regioselectivity and more modest selectivity has been observed with CPI derivatives including CC-1065 (ca. 4:1), duocarmycin SA (6.5–4:1) duocarmycin A (4–1:1), or CBQ derivatives (3:2). Like the comparisons made in the structural studies of CBQ, the diminished or lost regioselectivity observed with the agents may be attributed to the relative extent of stereoelectronic alignment of the two possible cyclopropane bonds. In the cases where structural information is available, the degree of selectivity reflects the relative degree of stereoelectronic alignment of the two available cyclopropane bonds and this alone could account for the exclusive reaction regioselectivity observed with 217 and 219 despite their remarkable reactivity. Further contributing to this regioselectivity is the resonance stabilizing effect of a fluorine substituents which could accommodate a developing partial positive change on C9.

Figure 35A:
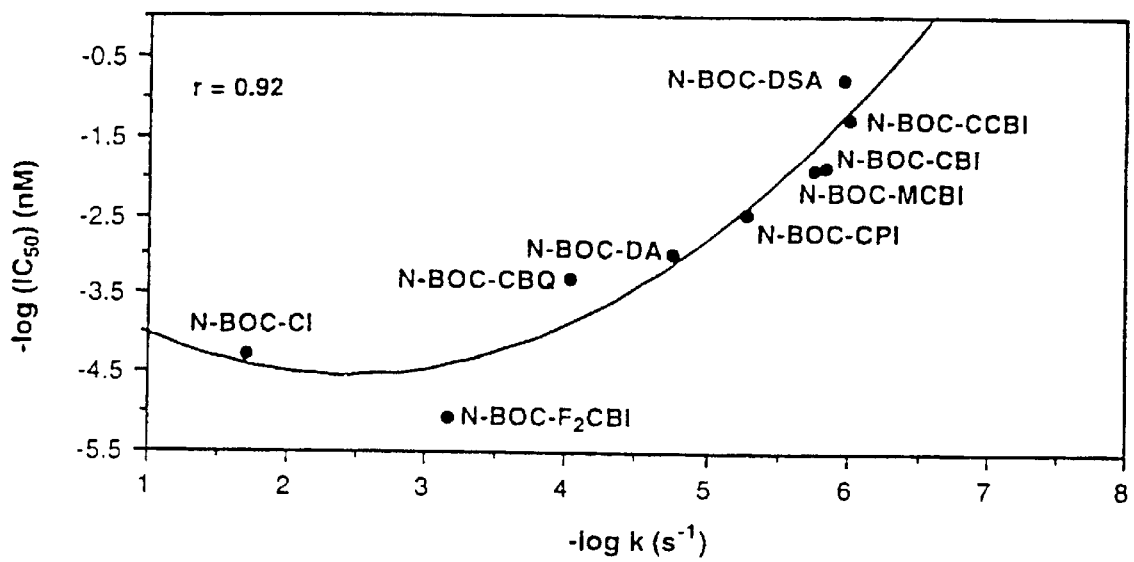
FIG. 35 illustrates that on the relative reactivity of the agents, they proved to be 500–1000× less potent than the corresponding CBI agent, FIG. 34. Qualitatively, this follows the differences observed in the relative reactivity of the agents (500×) exceptionally well with the more stable agents exhibiting the more potent activity and nicely follows the trends established in prior studies.
Figure 35B:
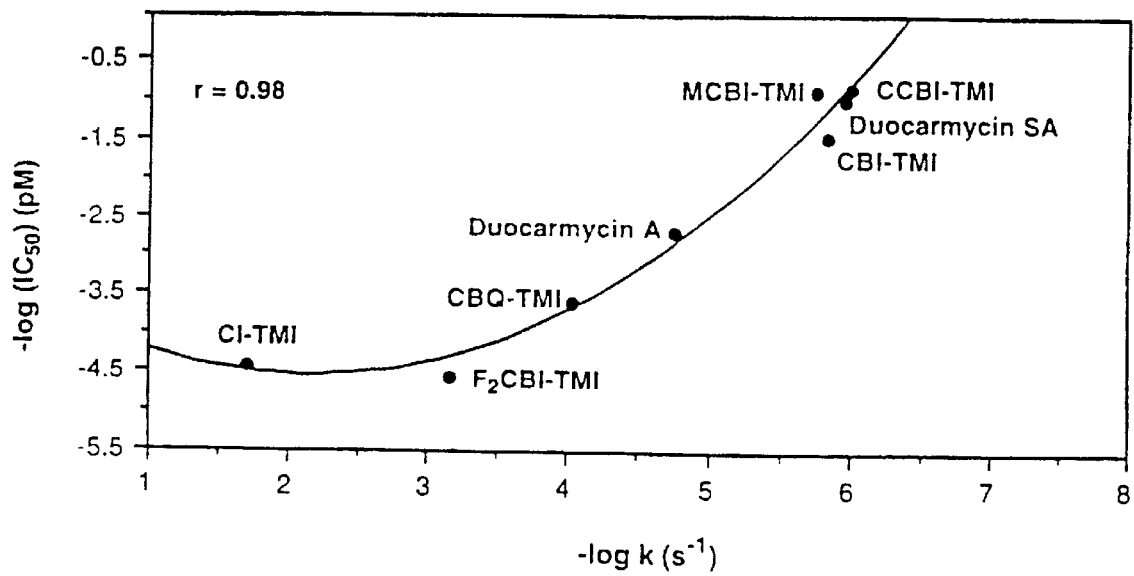

In Vitro Cytotoxic Activity. In preliminary studies, the in vitro cytotoxic activity of 217–219 and 224 ($F_2CBI$-TMI) were determined employing the racemic samples. Consistent with expectations based on the relative reactivity of the agents, they proved to be 500–1000× less potent than the corresponding CBI agent, FIG. 34. Qualitatively, this follows the differences observed in the relative reactivity of the agents (500×) exceptionally well with the more stable agents exhibiting the more potent activity and nicely follows the trends established in prior studies, FIG. 35.

DNA Alkylation Properties. A study of the DNA alkylation properties of the $F_2CBI$ agents was conducted and revealed that they behave analogous to the corresponding CBI-based agent. The DNA alkylation reaction was examined within w794 DNA for which comparative results are available for past agents. The alkylation site identification was obtained by thermal strand cleavage of the singly 5' end-labeled duplex DNA after exposure to the agents. Following treatment of the labeled DNA with a range of agent concentrations, the unbound agent was removed by EtOH precipitation of the DNA. Redissolution of the DNA in aqueous buffer, thermolysis at 100° C. (30 min) to induce depurination and strand cleavage at the adenine N3 or guanine N3 minor groove alkylation sites, denaturing high resolution PAGE adjacent to Sanger sequencing standards and autoradiography provided the DNA cleavage and alkylation sites.

Figure 36:
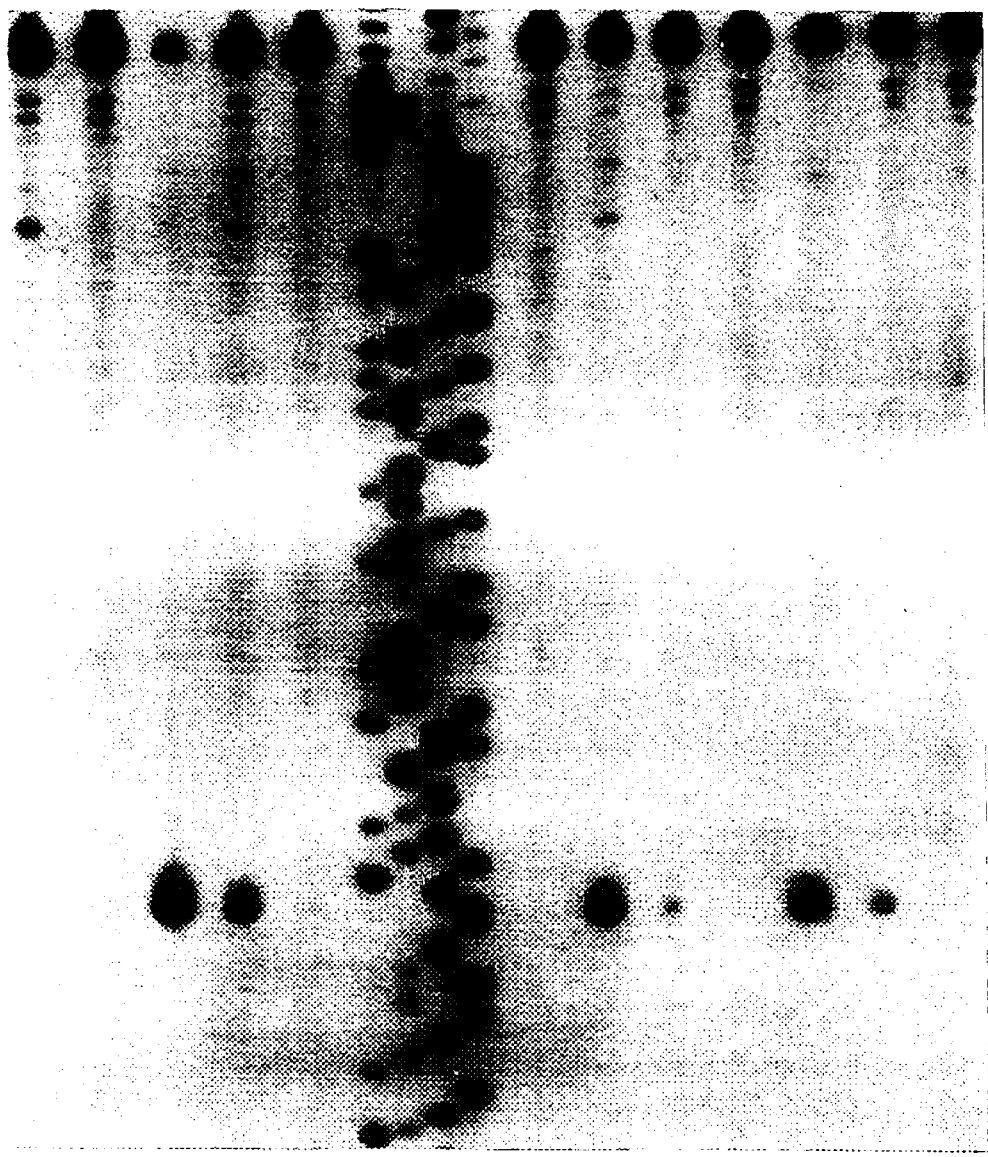
FIG. 36 illustrates thermally-induced (100° C., 30 min) strand cleavage of w794 DNA after agent treatment, 8% denaturing PAGE and autoradiography. Lanes 1–2, ent-(−)-CBI-TMI (25° C., $10^{-5}$ and $10^{-6}$ M); lanes 3–5, (+)-CBI-TMI (25° C., $10^{-5}$ to $10^{-7}$ M); lanes 6–9, G, C, A and T Sanger sequencing lanes; lane 10, DNA standard; lane 11–13, $F_2$CBI-TMI (25° C., $10^{-3}$ to $10^{-5}$ M); lanes 14–16, $F_2$CBI-TMI (4° C., $10^{-3}$ to $10^{-5}$ M).

A representative comparison of the DNA alkylation by racemic $F_2CBI$-TMI (224) alongside that of ent-(−)- and (+)-CBI-TMI is illustrated in FIG. 36. There are three important conclusions that can be drawn from the comparisons in FIG. 35. First, $F_2CBI$-TMI alkylates DNA in a manner analogous to CBI-TMI and does so with the same sequence selectivity. No new sites of alkylation were detected and only adenine N3 alkylation was detected under these conditions of limiting agent and excess DNA. Notably, such sequencing studies only detect the highest affinity alkylation sites and minor sites with comparable affinities (1–0.01×). Lower affinity alkylation sites are not detected since they require much higher agent concentrations leading to multiple alkylations and cleavages of DNA resulting in the production of short DNA fragments not observed on the sequencing gels. It is likely that 224, like duocarmycin A itself, may also be capable of guanine N3 alkylation in the absence of an accessible or available adenine N3 site, but it is not a major or minor reaction of significance. As evidenced by the comparison of ent-(−)- and (+)-CBI-TMI, the natural enantiomer of the CBI-based agents in the TMI series has been found to be 50–100× more potent and effective at alkylating DNA than the unnatural enantiomers, and no exceptions in the CBI series (CBI, MCBI, CCBI) have been observed. In the examination of racemic $F_2CBI$-

TMI, we can with confidence suggest that it is the natural enantiomer properties that dominates to the extent that it is responsible for the properties detected within w794 DNA as shown in FIG. 36.

Secondly, although there are no distinctions of significance in the DNA alkylation selectivity of $F_2$CBI-TMI and CBI-TMI itself, there is a substantial difference in the relative efficiencies of DNA alkylation. Consistent with both its relative stability and its relative cytotoxic potency, $F_2$CBI-TMI alkylated DNA 100–1000× less efficiently than CBI-TMI and this correlation with its other biological properties proved to be remarkably accurate. Quantitating this difference in efficiency by densitometry and averaging the results of several comparisons led to an average assessment that racemic $F_2$CBI-TMI was 675–725× less efficient than (+)-CBI-TMI. In contrast to CBI-TMI and other analogs of 1–3 containing stable alkylation subunits (CPI, DSA, CBI, MCBI, CCBI) but analogous to those possessing the most reactive (CI, DA, CBQ), the DNA alkylation efficiency of $F_2$CBI-TMI was found to steadily increase as the temperature was decreased from 37 to 25 to 4° C. This may be attributed to the nonproductive competitive solvolysis of the agent which competes with alkylation and this phenomenon is observed only with the most reactive of the agents studied to date.

Finally, implicit in these studies is the observation of exclusive adenine N3 addition to the C9 cyclopropane carbon consistent with expectations that the gem difluoro substitution would not effect the inherent regioselectivity. Although this was to be expected based on the chemical solvolysis studies with 217 and 219 which demonstrated that acid-catalyzed nucleophilic addition occurred at C9 with no evidence of ring expansion solvolysis, preceding studies even with agents that undergo solvolysis with a lower regioselectivity including the CPI-based agents and CC-1065 (4:1 regioselectivity), duocarmycin A (4–1:1 regioselectivity), duocarmycin SA (6–4:1 regioselectivity), and CBQ-based agents (3:2 regioselectivity) led to detection of only adducts derived from adenine N3 addition to the least substituted cyclopropane carbon. Each of these studies also quantitated the adduct formation and, in the case of duocarmycin A (86–92%), duocarmycin SA (95–100%), and the CBQ-based agents (>75%), led to the observation that the regioselectivity of the DNA alkylation reaction is greater than that of simple solvolysis. Although several explanations could be advanced for these observations, the two most prominent are preferential adoption of binding orientations that favor normal adenine N3 addition (proximity effects) and the significant destabilizing torsional strain and steric interactions that accompany the abnormal addition. Figures illustrating these effects have been disclosed in our prior work and we would suggest that this latter subtle effect is most substantial. Consequently, we would not have expected to detect the abnormal adenine N3 addition with $F_2$CBI-TMI even if its cyclopropane addition regioselectivity were more modest.

Conclusions. An effective synthesis of $F_2$CBI, a difluorocyclopropane analog of the alkylation subunits of CC-1065 and the duocarmycins, was accomplished and represents the first such agent examined containing functionalization of the reactive center in the natural products. The core structure was assembled through adoption of the Sundberg intramolecular insertion of an in situ generated metal carbenoid into a difluoroalkene employing a key p-quinonediazide.

At the onset of our study, it was not clear whether the fluorocyclopropane substitution would alter or enhance the typical reaction regioselectivity and whether it would enhance or diminish the electrophilic functional reactivity. The introduction of the two fluorine substituents converts the least substituted cyclopropane carbon of CBI into the most substituted, inductively removes electron density from the reacting center and, by virtue of resonance stabilization, could stabilize developing positive charge at the reacting, albeit already electropositive, center. Although the greater substitution could diminish nucleophilic addition to the C9 carbon, the relatively small size of fluorine made it difficult to assess in advance its impact on nucleophilic addition. The complementary electron-withdrawing properties of the fluorine substituents which diminish electron density at C9 and their potential resonance stabilization of developing positive change on C9 could enhance the regioselectivity of the nucleophilic cyclopropane ring opening reaction. In contrast, its established large impact on the bond opposite the two fluorine substituents could be anticipated to substantially lengthen and weaken the C8b-C9a bond and potentially redirect nucleophilic addition to C9a providing abnormal solvolysis with ring expansion.

A study of the acid-catalyzed nucleophilic addition to N-BOC-$F_2$CBI (219) and N-acetyl-$F_2$CBI (217) revealed that the difluorocyclopropane substitution increased the reactivity 500× despite the inductive electron-withdrawing properties of the reactive center substituents without altering the inherent regioselectivity which occurs with nucleophilic addition to the difluoro substituted C9 cyclopropane carbon. The maintained regioselectivity may be attributed to the potential partial positive charge stabilization by the two fluorine substituents and the stereoelectronic control of the reaction where only the cleaved C8b-C9 bond is aligned for reaction. This occurs in spite of the preferential weakening of the alternative but nonaligned C8b-C9a bond. In turn, this orientation of the cyclopropane is dictated by the geometrical constraints imposed by the fused 5-membered ring.

Ground state effects were found to account for the increased reactivity. The cyclopropane C—$CF_2$—C bond angle is expanded and the cyclopropane bond opposite the difluoro substitution is substantially lengthened to accommodate the preferentially compressed exocyclic F—C—F bond angle introducing additional strain energy and increasing the reactivity of $F_2$CBI. This strain-derived ground state destabilization and increase in reactivity is exactly analogous to that found in simple related systems and is not unique or even perturbed by incorporation into $F_2$CBI. Moreover, it is sufficient to overcome any stabilization potentially derived from the electron-withdrawing inductive effect of the fluorine substitution.

Qualitatively consistent with this increased reactivity (500×) and following a prior established relationship, the agents were found to be 500–1000× less cytotoxic than the corresponding CBI derivative. Similarly, the difluorocyclopropane substitution had no detectable effect on the DNA alkylation selectivity of the agents and they were found to undergo the characteristic adenine N3 addition to the C9 cyclopropane carbon but did so with a reduced efficiency (675–725×) nicely following the cytotoxicity/stability correlations.

EXAMPLE 4

Synthesis and Studies on the Role of Duocarmycin SA Methoxy Substituents

The preparation and examination of 304–307 revealed that (+)-305 and (+)-duocarmycin SA were indistinguishable. In contrast, 306 and 307 exhibited properties more analogous to 304 illustrating that the C6 and C7 methoxy substituents of duocarmycin SA contribute little or nothing to its properties. Thus, the C5 methoxy substituent of the 5,6,7-trimethoxyindole subunit of duocarmycin SA is necessary and sufficient for observation of the full potency of the natural product.

One important structural component of the natural products is the right-hand subunits linked to the alkylation subunit through an $N^2$ amide which has been shown to increase the DNA alkylation rate, efficiency, and selectivity and to increase biological potency $10^3$–$10^4 \times$. In this example, we examine in detail the trimethoxyindole-2-carboxylate subunit of duocarmycin SA with the intention of defining the importance and potential role of each of the three methoxy substituents. The results of the study clearly highlight the unique importance of the C5 methoxy substituent that is imbedded deeply in the minor groove upon DNA alkylation, and a previously unrecognized role of this substituent is proposed.

Figure 37:
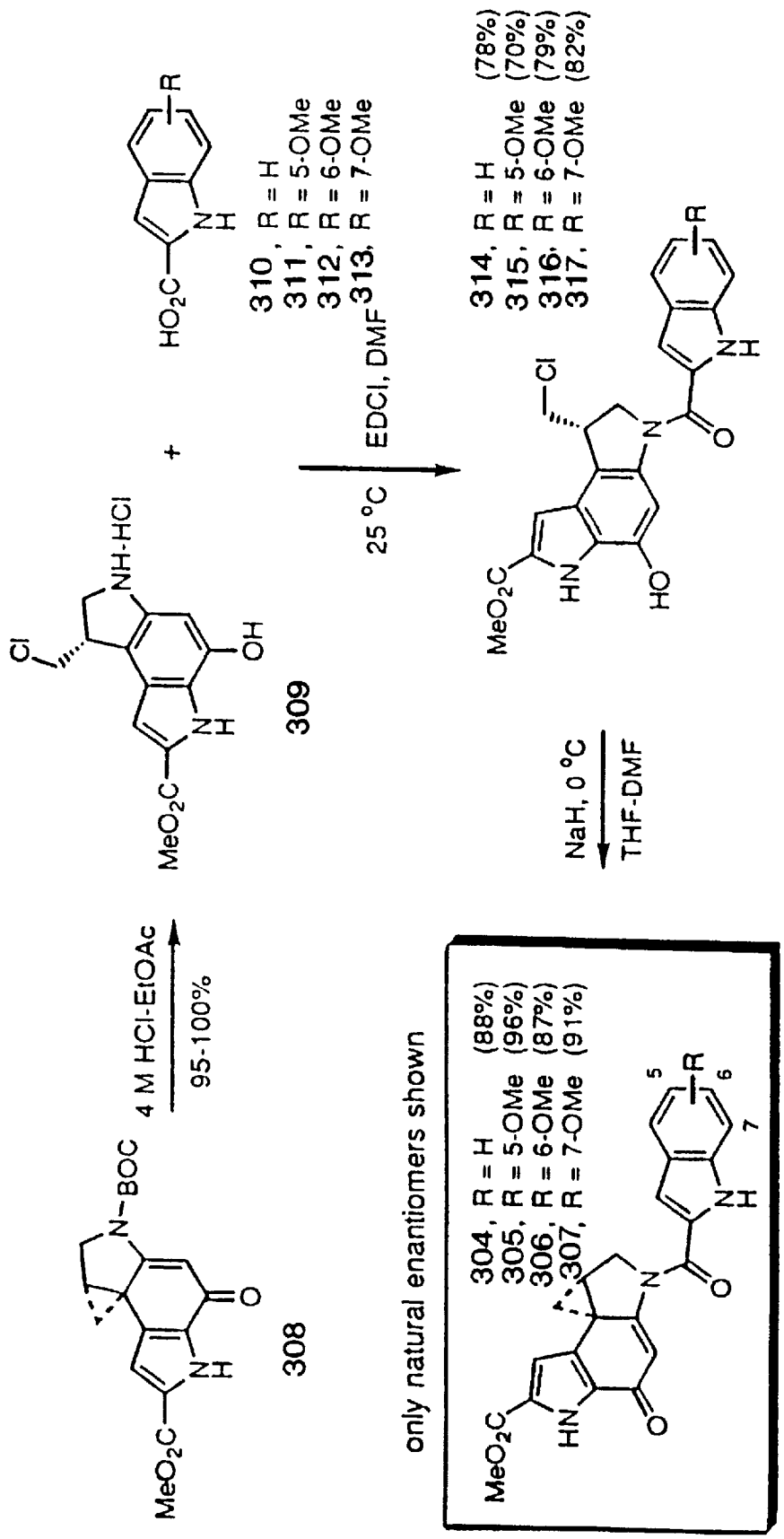
FIG. 37 illustrates the synthesis of SA Methoxy analogs.

The agents 304–307 were targeted for evaluation since 305–307 provide an assessment of the individual contribution of the three methoxy groups of 1 in their comparisons with 1 and 304. The optically active duocarmycin SA alkylation subunit, N-BOC-DSA (308), was prepared as previously disclosed in Boger et al. *J. Am. Chem. Soc.* 1992, 114, 10056; Boger et al. *J. Am. Chem. Soc.* 1993, 115, 9025. Resolution of 308 was effected by direct chromatographic separation on a semipreparative ChiralCel OD HPLC column (10 μm 2×25 cm, 30% 2-propanol/hexane, 7 mL/min, α=1.24, 99.9% ee). This proved more effective and convenient than our previously reported method of bis-(R)-O-acetylmandelate derivatization of an immediate precursor and chromatographic separation of the corresponding diastereomers followed by mandelate ester hydrolysis with regeneration of the pure enantiomers (Boger et al. *J. Am. Chem. Soc.* 1992, 114, 10056; Boger et al. *J. Am. Chem. Soc.* 1993, 115, 9025). Acid-catalyzed deprotection of 308 (4 M HCl-EtOAc, 25° C., 30 min, 95–100%) that was accompanied by clean addition of HCl to the activated cyclopropane provided the seco HCl salt 309 (FIG. 37). Immediate coupling (3 equiv EDCI, DMF, 25° C., 4–15 h) of 309 with the indole-2-carboxylic acids 310–313 (1.1 equiv) in the deliberate absence of added base provided the penultimate precursors 314–317 in excellent conversions (70–82%). Spirocyclization was effected by treatment with NaH (3 equiv, THF-DMF 4–2:1, 0° C., 30 min) to provide both enantiomers of the agents 304–307 in excellent conversions (87–96%). Coupling of 309 in the presence of mild base including $NaHCO_3$ leads to competitive spirocyclization and the presence of adventitious moisture in the following spirocyclization reaction mixture will lead to subsequent hydrolysis of the linking $N^2$ amide.

In Vitro Cytotoxic Activity. The in vitro cytotoxic activity of both enantiomers of 304–307 along with that of 1 is summarized in FIG. 38. For the natural enantiomers, removal of the three methoxy groups led to a 6.5-fold reduction in potency. The 5-methoxy derivative (+)-305 was indistinguishable from duocarmycin SA illustrating that its C6 and C7 methoxy groups are not contributing significantly to its properties. Consistent with this, (+)-307 was equipotent with (+)-304 indicating that C7 methoxy group does not contribute to the properties of (+)-1 while (+)-306 exhibited intermediate activity suggesting it may potentiate the effects of the C5 methoxy substituent. Similar, but more pronounced effects were observed with the unnatural enantiomers. The unnatural enantiomers of 304, 306, and 307 were essentially equipotent and 13–18× less potent than ent-(−)-1 while ent-(−)-305 more closely approached the full activity of ent-(−)-1.

DNA Alkylation Selectivity, Efficiency, and Rate.

Figures 38, 39:
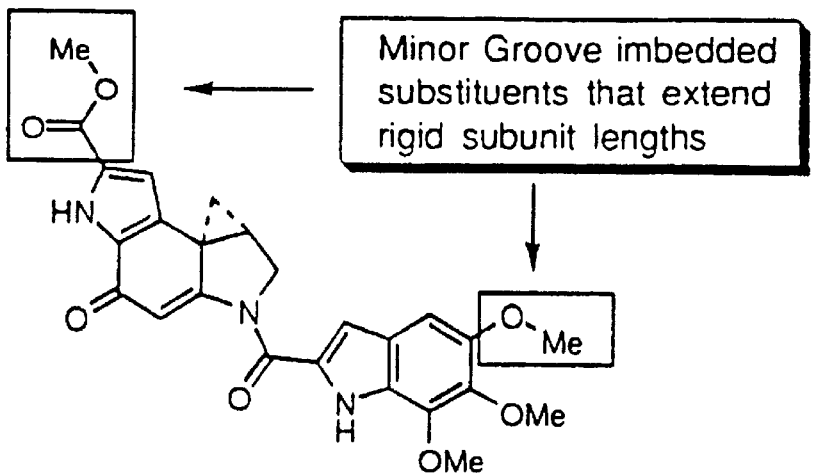
FIG. 38 illustrates a table wherein all five agents exhibited nearly identical DNA alkylation selectivities and the distinctions observed were found in the rates and overall efficiencies of DNA alkylation.
FIG. 39 illustrates that the presence of the methoxy group influences the analogs to imbed itself into the minor groove via its rigid subunits.

The DNA alkylation selectivity and efficiency of the natural enantiomers of 304–307 were compared with that of 1 in w794 DNA. All five agents exhibited nearly identical DNA alkylation selectivities and the distinctions observed were found in the rates and overall efficiencies of DNA alkylation. When the incubation with w794 DNA was conducted at 25° C. for 24 h, 305 was found to be essentially indistinguishable from 1 itself, 306 and 307 (306>307) were 5–10× less efficient than 1 or 305, and 304 was the least effective of the agents being 20× less efficient than 1 or 305 (FIG. 38). These trends in the overall efficiency of DNA alkylation parallel the relative trends in cytotoxic potency. Similarly, the relative rates of DNA alkylation for 1, 305, and 304 were also examined within w794 ($10^{-5}$ M, 25° C., 1–72 h) at the single high affinity site of 5'-d(AATTA). (+)-Duocarmycin SA (1) and 305 were nearly indistinguishable with 1 exhibiting a slightly faster rate ($k_{rel}$=1.3–2.3) and both were substantially faster than that of 304 ($k_{rel}$=18–33).

The C7 and C6 methoxy groups, which lie on the outer face of the DNA-agent complex, individually contribute little (C6>C7) to the properties of duocarmycin SA. In contrast, the C5 methoxy group that is deeply imbedded in the minor groove contributes prominently to its properties. The agent containing a single C5 methoxy substituent proved indistinguishable from duocarmycin SA indicating that it alone is sufficient for observation of the full potency of the natural product. This is consistent with a role in which the C5 methoxy group provides further noncovalent binding stabilization for the inherently reversible DNA alkylation reaction by virtue of its placement deep in the minor groove and the lack of such an effect for the C6/C7 methoxy substituents is consistent with quantitative modeling studies. In addition, the C5 methoxy group of duocarmycin SA extends the rigid length of the DNA binding subunit. Its presence results in an increase in the inherent twist in the helical conformation of the DNA bound agent with the helical rise of the agent adjusted at the site of linking $N^2$ amide. This twist in the conformation at the $N^2$ amide disrupts the vinylogous amide conjugation in the alkylation subunit and increases the inherent reactivity of the agent contributing to the catalysis of the DNA alkylation reaction. Removing the C5 methoxy substituent shortens the length of the right-hand subunit, decreases the inherent twist in the linking $N^2$ amide in the DNA bound conformation, and less effectively activates the agent for DNA alkylation.

Synthetic Methods

Ethyl 7-Bromo-4-hydroxy-2-naphthalenecarboxylate (6). Method A: A solution of t-BuOK (7.19 g, 64.1 mmol) in t-BuOH (100 mL) at 45° C. was treated with a mixture of m-bromobenzaldehyde (4, 10.78 g, 58.3 mmol) and diethyl succinate (15.23 g, 87.4 mmol) dropwise. The reaction mixture was warmed at reflux for 2 h. After cooling to 25° C., the mixture was neutralized with the addition of 10% aqueous HCl (pH=1) and the t-BuOH was removed from the organic layer under reduced pressure. The residue was extracted with EtOAc (3×30 mL). The half ester was extracted from the organic layer with 5% aqueous $NaHCO_3$ (5×30 mL). The combined basic aqueous layers were washed reacidified with aqueous 3M HCl and extracted with EtOAc (3×30 mL). The combined organic layers were washed with saturated aqueous NaCl and dried ($MgSO_4$).

Solvent removal yielded a mixture of the two isomeric half-esters 5 (13.7 g, 18.2 g theoretical, 75%) as an amber oil.

The half-esters 5 (13.66 g) were dissolved in 300 mL of $Ac_2O$. Anhydrous NaOAc (3.93 g, 48.0 mmol) was added and the reaction mixture was warmed at reflux for 6 h. The $Ac_2O$ was removed under reduced pressure and the residue was suspended in 10% aqueous $Na_2CO_3$ (100 mL) and extracted with EtOAc (3×100 mL). The combined organic layers were dried ($Na_2SO_4$) and concentrated. The residue was dissolved into 150 mL of 3 M HCl—EtOH at 0° C. and the solution was allowed to warm to 25° C. and stir for 16 h. The solvent was removed under reduced pressure. Chromatography ($SiO_2$, 5×20 cm, 20% EtoAc-hexane) and subsequent recrystallization from toluene afforded pure 6 as a white solid free of contaminant 8.

Method B: NaH (2.99 g, 74.6 mmol, 1.05 equiv, 60% dispersion in mineral oil) was washed with $Et_2O$ (3×20 mL) and suspended in anhydrous THF (100 mL) under Ar. The suspension was cooled to 0° C. and 10 (24.77 g, 72.3 mmol, 1.03 equiv) was added dropwise under Ar and the reaction mixture was stirred at 0° C. for 2 h. The solution was then transferred by cannula to a solution of m-bromobenzaldehyde (4, 13.15 g, 71.1 mmol, 1 equiv) in 80 mL of THF at 0° C. The resulting reaction mixture was stirred at 0° C. for 1 h before being allowed to warm to 25° C. and the mixture was stirred overnight. The solvent was removed under vacuum and the residue was partitioned between $H_2O$ and $CH_2Cl_2$. The aqueous phase was extracted with $CH_2Cl_2$ (3×200 mL), and the combined organic layers were dried ($MgSO_4$) and concentrated. The diester was purified by passage through a plug of $SiO_2$ (10% EtOAc-hexane) to provide 11 (26.3 g, 26.3 g theoretical, 100%) as a clear oil: $^1H$ NMR ($CDCl_3$, 250 MHz) δ7.73 (s, 1H), 7.48 (s, 1H), 7.45 (m, 1H), 7.26 (d, 1H, J=5.8 Hz), 7.25 (d, 1H, J=6.8 Hz), 4.25 (q, 2H, J=7.1 Hz), 3.38 (s, 2H, $CH_2CO_2tBu$), 1.44 (s, 9H), 1.30 (t, 3H, J=7.1 Hz); $^{13}C$ NMR ($CDCl_3$, 62.5 MHz) δ169.6, 166.7, 139.2, 137.0, 131.4, 131.3, 129.8, 127.9, 127.3, 122.3, 80.9, 60.9, 34.5, 27.7, 14.0; IR (film) $v_{max}$ 2978, 2930, 1728, 1641, 1560, 1474, 1368, 1329, 1279, 1198, 1154, 1097, 786, 682 $cm^{-1}$; FABHRMS (NBA-CsI) m/z 500.9664 ($M^+$+Cs, $C_{17}H_{21}BrO_4$ requires 500.9678).

A solution of 11 (16.6 g, 46.5 mmol) in 90% aqueous $CF_3CO_2H$ (75 mL) and was stirred for 30 min at 25° C. The solvent was removed under reduced pressure and the residue was azeotroped two times with benzene. The half-ester 5 was purified by dissolution in saturated aqueous $NaHCO_3$ solution (50 mL). Acidification of the aqueous phase with 10% aqueous HCl (pH=1), extraction with EtOAc (3×50 mL), followed by drying the combined organic phase ($Na_2SO_4$) and concentration afforded pure 5 (14.6 g, 14.6 g theoretical, 100%) as a pale yellow oil which crystallized under vacuum: mp 78–80° C.; $^1H$ NMR ($CDCl_3$, 400 MHz) δ7.83 (s, 1H), 7.50 (m, 2H), 7.29 (m, 2H), 4.30 (q, 2H, J=7.1 Hz), 3.52 (s, 2H), 1.33 (t, 3H, J=7.1 Hz); $^{13}C$ NMR ($CDCl_3$, 100 MHz) δ175.6, 167.1, 140.4, 136.8, 131.9, 131.8, 130.3, 127.3, 126.8, 122.8, 61.5, 33.5, 13.6; IR (neat) $v_{max}$ 2984, 1709, 1639, 1556, 1472, 1370, 1278, 1194, 1092, 1018, 782 $cm^{-1}$; FABHRNS (NBA-NaI) m/z 334.9883 ($M^+$+Na, $C_{13}H_{13}BrO_4$ requires 334.9895).

The half-ester 5 (14.56 g, 46.5 mmol) was dissolved in $Ac_2O$ (310 mL, 0.15 M) under Ar. KOAc (5.93 g, 60.5 mmol, 1.3 equiv) was added and the reaction mixture was warmed at reflux for 30 min. The hot solution was poured into $H_2O$ (400 mL) which was stirred and allowed to cool to 25° C. The product was collected by filtration and recrystallized from $CH_3OH$ to yield pure 7 (10.06 g, 15.68 g theoretical, 65%) free of contaminant 9. For 7: mp 113–114° C. ($CH_3OH$); $^1H$ NMR ($CDCl_3$, 250 MHz) δ8.34 (s, 1H, C1-H), 8.08 (d, 1H, J=1.6 Hz, C8-H), 7.77–7.59 (m, 3H), 4.38 (q, 2H, J=7.1 Hz), 2.45 (s, 3H), 1.37 (t, 3H, J=7.1 Hz); IR (neat) $v_{max}$ 2986, 1770, 1717, 1591, 1369, 1273, 1238, 1190, 1155, 1099, 1068, 1057, 1020, 907, 815 $cm^{-1}$; FAB-HRMS (NBA) m/z 358.9882 ($M^+$, $C_{15}H_{13}BrO_4$ requires 358.9895).

The acetate 7 (15.7 g, 46.6 mmol) was dissolved in EtOH (200 mL) and $K_2CO_3$ (32.2 g, 233 mmol, 5 equiv) was added. The reaction mixture was warmed at reflux for 1 h, cooled to 25° C. and poured into $H_2O$ (200 mL). The mixture was acidified with the addition of 10% aqueous HCl (pH=1) and the desired product was extracted into EtOAc (3×250 mL). The combined organic layers were washed with saturated aqueous NaCl, dried ($MgSO_4$) and the solvent was removed under reduced pressure. The resulting solid was recrystallized from toluene to yield 6 (14.62 g, 14.62 g theoretical, 100%): mp 180° C. (needles, toluene); $^1H$ NMR (acetone-$d_6$, 250 MHz) δ9.53 (br s), 8.23 (d, 1H, J=1.8 Hz), 8.18 (d, 1H, J=9.0 Hz), 8.09 (s, 1H), 7.68 (dd, 1H, J=2.0, 8.9 Hz), 7.50 (d, 1H, J=1.4 Hz), 4.37 (q, 2H, J=7.1 Hz), 1.38 (t, 3H, J=7.1 Hz); $^{13}C$ NMR (acetone-$d_6$, 100 MHz) δ166.5, 154.3, 136.0, 131.6, 130.9, 130.5, 126.3, 125.2, 121.7, 121.6, 108.4, 61.7, 14.5; IR (KBr) $v_{max}$ 3379, 2989, 1701, 1588, 1476, 1420, 1399, 1386, 1360, 1284, 1252, 1080, 1026, 966, 893, 816, 768 $cm^{-1}$; FABHRMS (NBA) m/z 293.9888 ($M^+$, $C_{13}H_{11}BrO_3$ requires 293.9892).

Anal. Calcd for $C_{13}H_{11}BrO_3$: C, 52.91; H, 3.76. Found: C, 53.17; H, 3.46.

Ethyl 4-Benzyloxy-7-bromo-2-naphthalenecarboxylate (12). A solution of 6 (8.04 g, 2.2 mmol) in anhydrous DMF (150 mL) under Ar was treated with $K_2CO_3$ (5.65 g, 40.9 mmol), benzyl bromide (5.59 g, 32.7 mmol, 1.2 equiv) and $BU_4NI$ (402 mg, 1.1 mmol, 0.04 equiv). After stirring for 11 h at 25° C., the reaction mixture was poured into $H_2O$ (200 mL) and extracted with EtOAc (3×200 mL). The combined organic layers were washed with saturated aqueous NaCl, dried ($MgSO_4$) and concentrated. The resulting solid was recrystallized from 5% EtOAc-hexane to afford 12 (8.36 g, 10.49 g theoretical, 80%) as white needles. An additional 2.13 g (20%) of 12 was obtained by chromatography ($SiO_2$, 4×20 cm, 10% EtOAc-hexane) of the crystallization mother liquors: mp 105° C. (needles, hexane); $^1H$ NMR ($CDCl_3$, 250 MHz) δ8.19 (d, 1H, J=8.8 Hz), 8.10 (s, 1H), 8.05 (d, 1H, J=1.8 Hz), 7.61 (dd, 1H, J=1.9, 8.9 Hz), 7.50 (m, 6H), 5.28 (s, 2H), 4.45 (q, 2H, J=7.1 Hz), 1.46 (t, 3H, J=7.1 Hz); $^{13}C$ NMR ($CDCl_3$, 100 MHz) δ166.5, 154.7, 136.4, 134.7, 130.8, 130.7, 129.1, 128.7, 128.3, 127.6, 126.3, 124.2, 122.5, 121.5, 104.6, 70.4, 61.4, 14.4; IR (KBr) $v_{max}$ 2986, 1716, 1589, 1578, 1406, 1369, 1331, 1279, 1238, 1098, 1025, 962, 892, 816, 767, 725, 691 $cm^{-1}$; FABHRS (NBA) m/z 384.0370 ($M^+$, $C_{20}H_{17}BrO_3$ requires 384.0361).

Anal. Calcd for $C_{20}H_{17}BrO_3$: C, 62.35; H, 4.45. Found: C, 62.23; H, 4.61.

Ethyl 4-Benzyloxy-7-cyano-2-naphthalenecarboxylate (13). A solution of 12 (9.46 g, 27.2 mmol) in anhydrous DMF (12.6 mL) under Ar was treated with CuCN (2.92 g, 32.6 mmol, 1.2 equiv) and the mixture was warmed at reflux for 20 h. The reaction mixture was cooled to 25° C. and poured into 250 mL of $H_2O$ to which $FeCl_3$ (5.29 g, 32.6 mmol, 1.2 equiv) was added with swirling. The solution was extracted with EtOAc (3×200 mL) and the combined organic layers were washed with saturated aqueous NaCl, dried ($MgSO_4$) and concentrated. Recrystallization from 20% EtOAc-hexane provided 13 (6.70 g, 9.00 g theoretical, 74%) as a white solid. Chromatography (SiO$_2$, 4×20 cm, 10% EtOAc-hexane) of the crystallization mother liquors afforded additional 13 (2.00 g, 22%, 96% combined) as white solid: mp 125° C. (needles, EtOH); $^1$H NMR (CDCl$_3$, 250 MHz) δ8.43 (d, 1H, J=8.7 Hz), 8.29 (s, 1H), 8.25 (s, 1H), 7.69 (dd, 1H, J=1.6, 8.7 Hz), 7.66 (s, 1H), 7.56–7.39 (m, 5H), 5.32 (s, 2H), 4.46 (q, 2H, J=7.2 Hz), 1.46 (t, 3H, J=7.1 Hz); $^{13}$C NMR (CDCl$_3$, 62.5 MHz) δ165.9, 154.3, 135.9, 134.6, 132.3, 129.8, 128.6, 128.3, 128.2, 127.8, 127.5, 123.8, 123.2, 118.6, 110.7, 106.9, 70.5, 61.5, 14.3; IR (KBr) v$_{max}$ 2994, 2226, 1711, 1577, 1502, 1284, 1252, 1093, 1029, 916, 827 cm$^{-1}$; FABHRMS (NBA) m/z 332.1276 (M$^+$+H, C$_{21}$H$_{17}$NO$_3$ requires 332.1287).

Anal. Calcd for C$_{21}$H$_{17}$NO$_3$: C, 76.11; H, 5.17; N, 4.23. Found: C, 75.96; H, 5.42; N, 4.31.

4-Benzyloxy-7-cyano-2-naphthalenecarboxylic Acid (14). A solution of 13 (8.67 g, 26.2 mmol) in 260 mL of THF—CH$_3$OH—H$_2$O (3:1:1) was treated with LiOH—H$_2$O (5.49 g, 131 mmol, 5 equiv) and the mixture was stirred at 25° C. for 25 h. The solution was acidified with the addition of 10% aqueous HCl (pH<1) and the product partially precipitated. The product was collected by filtration and the remaining aqueous phase was extracted with EtOAc (3×200 mL). The combined organic layers were dried (MgSO$_4$) and concentrated in vacuo to afford a combined 14 (7.94 g, 7.94 g theoretical, 100%): mp 235° C. (white powder, EtOH); $^1$H NMR (DMSO-d$_6$, 400 MHz) δ8.73 (d, 1H, J=1.1 Hz), 8.34 (d, 1H, J=8.9 Hz), 8.32 (s, 1H), 7.88 (dd, 1H, J=1.5, 8.9 Hz), 7.63 (s, 1H), 7.57–7.34 (m, 5H), 5.38 (s, 2H); $^{13}$C NMR (CDCl$_3$, 100 MHz) δ167.3, 153.8, 136.6, 135.5, 132.3, 130.3, 128.6, 128.3, 128.1, 127.6, 126.4, 123.4, 121.9, 118.8, 110.0, 107.5, 70.0; IR (KBr) v$_{max}$ 3000 (br), 2227, 1687, 1577, 1499, 1419, 1343, 1283, 1250, 1105, 996, 915, 836, 740 cm$^{-1}$; FABHRMS (NBA) m/z 304.0964 (M$^+$+H, C$_{19}$H$_{13}$NO$_3$ requires 304.0974).

N-(tert-Butyloxycarbonyl)-4-benzyloxy-7-cyano-2-naphthylamine (15). A solution of 14 (500 mg, 1.65 mmol) in freshly distilled t-BuOH (165 mL) was treated with Et$_3$N (0.276 mL, 1.98 mmol, 1.2 equiv) and 5 g of activated 4 Å molecular sieves. Diphenylphosphoryl azide (0.426 mL, 1.98 mmol, 1.2 equiv) was added and the reaction mixture was warmed at reflux for 14 h. The mixture was cooled to 25° C. and the solvent was removed under vacuum. The residue was dissolved in EtOAc and the organic phase was washed with 10% aqueous HCl, dried (Na$_2$SO$_4$), and concentrated in vacuo. Chromatography (SiO$_2$, 3×20 cm, 20% EtOAc-hexane) afforded 15 (534 mg, 618 mg theoretical, 87%) as a white crystalline solid: mp 145° C. (white needles, 10% EtOAc-hexane); $^1$H NMR (CDCl$_3$, 250 MHz) δ8.26 (d, 1H, J=8.7 Hz), 8.01 (s, 1H), 7.45 (m, 7H), 7.23 (s, 1H), 6.84 (s, 1H), 5.21 (s, 2H), 1.57 (s, 9H); $^{13}$C NMR (CDCl$_3$, 62.5 MHz) δ154.9, 152.5, 138.1, 136.1, 133.6, 132.6, 128.6, 128.2, 127.4, 124.1, 123.6, 123.5, 119.3, 110.5, 106.5, 101.7, 81.1, 70.4, 28.3; IR (KBr) v$_{max}$ 3327, 2980, 2223, 1701, 1586, 1545, 1420, 1369, 1341, 1251, 1160, 1107, 1064, 1002, 910, 820, 744, 694 cm$^{-1}$; FABHRMS (NBA) m/z 374.1641 (M$^+$, C$_{23}$H$_{22}$N$_2$O$_3$ requires 374.1630).

Anal. Calcd for C$_{23}$H$_{22}$N$_2$O$_3$: C, 73.78; 5.92; N, 7.48. Found: C, 73.20; H, 5.84; N, 7.23.

N-(tert-Butyloxycarbonyl)-4-benzyloxy-1-bromo-7-cyano-2-naphthylamine (16). A solution of 15 (137 mg, 0.366 mmol) in freshly distilled THF (7.3 mL) and cooled to −78° C. under Ar was treated with 10 μL of a 1 μL/mL solution of H$_2$SO$_4$ in THF and the solution was stirred for 20 min before the addition of NBS (78 mg, 439 mmol, 1.2 equiv). The reaction mixture was allowed to warm to −60° C. and was stirred for 4 h at which time the reaction was complete by TLC. Et$_2$O (7.3 mL) was added and the resulting organic phase was washed with 5% aqueous NaHCO$_3$ (1×10 mL), saturated aqueous NaCl (1×10 mL), dried (MgSO$_4$), and concentrated in vacuo. Chromatography (SiO$_2$, 2×20 cm, 10% EtOAc-hexane) afforded 16 (145 mg, 166 mg theoretical, 87%) as a white crystalline solid: mp 179° C. dec (white needles, 10% EtOAc-hexane); $^1$H NMR (CDCl$_3$, 250 MHz) δ8.40 (s, 1H, C8-H), 8.26 (d, 1H, J=8.5 Hz), 8.23 (s 1H, C3-H), 7.5–7.3 (m, 6H), 5.23 (s, 2H), 1.58 (s, 9H); $^{13}$C NMR (CDCl$_3$, 75 MHz) δ154.4, 152.4, 137.0, 136.0, 132.2, 132.0, 128.7, 128.6, 128.4, 128.0, 124.9, 124.8, 124.2, 119.1, 111.9, 102.0, 81.9, 70.8, 28.3; IR (KBr) v$_{max}$ 3416, 2978, 2230, 1738, 1623, 1603, 1570, 1498, 1405, 1364, 1335, 1229, 1158, 990, 970, 878, 850, 823, 758, 696 cm$^{-1}$; FABHRMS (NBA-CsI) m/z 584.9793 (M$^+$+Cs, C$_{23}$H$_{21}$BrN$_2$O$_3$ requires 584.9790).

Anal. Calcd for C$_{23}$H$_{21}$BrN$_2$O$_3$: C, 60.94; H, 4.67; N, 6.18. Found: C, 61.12; H, 4.75; N, 6.04.

N-(tert-Butyloxycarbonyl)-N-(3-methyl-2-buten-1-yl)-4-benzyloxy-1-bromo-7-cyano-2-naphthylamine (17). A solution of 16 (1.77 g, 3.90 mmol) in anhydrous DMF (20 mL) under Ar was treated with NaH (206 mg, 5.1 mmol, 1.3 equiv, 60% oil dispersion) and the reaction mixture was stirred for 30 min. The mixture was cooled to 0° C. and 4-bromo-2-methyl-2-butene (1.35 mL, 11.7 mmol, 3 equiv) was added dropwise by cannula. The solution was stirred at 0° C. for 1 h before being allowed to warm to 25° C. and stirred overnight. Water (20 mL) was added and the aqueous phase was extracted with EtoAc (3×15 mL). The combined organic phases were washed with saturated aqueous NaCl (1×30 mL), dried (Na$_2$SO$_4$) and the solvent was removed under vacuum. Chromatography (SiO$_2$, 4×20 cm, 10% EtOAc-hexane) afforded 17 (2.05 g, 2.03 g theoretical, >99%) as an amber oil: $^1$H NMR (CDCl$_3$, 400 MHz) δ8.66 (d, 1H, J=0.5 Hz), 8.40 (d, 1H, J=8.6 Hz), 7.63 (d, 1H, J=8.6 Hz), 7.51–7.34 (m, 5H), 6.85 (s, 1H), 5.24 (d, 1H, J=9.5 Hz), 5.20 (d, 1H, J=11.7 Hz), 5.17 (d, 1H, J=11.7 Hz), 4.40 (dd, 1H, J=6.1, 14.5 Hz), 4.01 (dd, 1H, J=7.7, 14.9 Hz), 1.61 (s, 3H), 1.57 (s, 3H), 1.37 and 1.30 (two s, 9H); $^{13}$C NMR (CDCl$_3$, 100 MHz) δ153.7, 140.9, 136.3, 135.8, 133.5, 128.8, 128.5, 127.3, 126.7, 124.1, 119.8, 119.5, 118.8, 111.7, 110.9, 81.0, 80.5, 70.8, 47.7, 46.3, 28.5, 28.2, 25.7; IR (film) v$_{max}$ 3467 (br), 2928, 2229, 1701, 1676, 1596, 1503, 1438, 1387, 1335, 1255, 1164, 1090, 863, 738 cm$^{-1}$.

Anal. Calcd for C$_{28}$H$_{29}$BrN$_2$O$_3$: C, 64.60; H, 5.62; N, 5.38. Found: C, 64.51; H, 5.74; N, 5.18.

N-(tert-Butyloxycarbonyl)-N-(formylmethyl)-4-benzyloxy-1-bromo-7-cyano-2-naphthylamine (18). A solution of 17 (180 mg, 0.345 mmol) in 22 mL (0.016 M) of 20% CH$_3$OH—CH$_2$Cl$_2$ was cooled to −78° C. A stream of 3% O$_3$/O$_2$ (160 L/min) was bubbled through the solution for 72 s. The reaction was immediately quenched with the addition of 0.81 mL of dimethyl sulfide and the mixture was allowed to stir at −78° C. for 5 min before being allowed to warm to 25° C. and stirred for 5 h. The solvent was removed in vacuo. Chromatography (SiO$_2$, 2×20 cm, 30% EtOAc-hexane) afforded 18 (155 mg, 171 mg theoretical, 91%) as a white foamy solid: $^1$H NMR (CDCl$_3$, 400 MHz) δ9.76 and 9.73 (two s), 8.63 and 8.61 (two s, 1H), 8.41 and 8.36 (two d, 1H, J=8.7 Hz), 7.64 and 7.60 (two dd, 1H, J=1.4, 8.7 Hz), 7.50–7.34 (m, 5H), 7.17 and 7.14 (two s, 1H), 5.26, 5.29 and 5.17 (one s and two d, 2H, J=11.4 Hz), 4.76 and 4.65 (two d, 1H, J=18.8 Hz), 4.01 and 3.95 (two d, 1H, J=18.8 Hz), 1.31 and 1.52 (two s, 9H); $^{13}$C NMR (CDCl$_3$, 100 MHz, major rotamer) δ197.3, 154.1, 140.8, 135.6, 133.4, 132.0, 128.8, 128.7, 128.5, 127.9, 127.6, 127.1, 124.2, 118.7, 113.8, 112.0, 110.5, 81.8, 70.9, 58.9, 28.1; IR (film) $v_{max}$ 2976, 2229, 1706, 1596, 1415, 1369, 1335, 1259, 1225, 1152, 1096, 848 cm$^{-1}$; FABHRMS (NBA) m/z 495.0922 (M$^+$+H, $C_{25}H_{23}BrN_2O_4$ requires 495.0919).

Anal. Calcd for $C_{25}H_{23}BrN_2O_4$: C, 60.62; H. 4.68; N, 5.65. Found: C, 60.39; H, 4.61; N, 5.69.

2-[N-(tert-Butyloxycarbonyl)-N-(3-tetrahydropyranyloxy-2-propen-1-yl)]amino-4-benzyloxy-1-bromo-7-cyanonaphthalene (19). A suspension of triphenyl[(2-tetrahydropyranyloxy)methyl]phosphonium chloride[54] (635 mg, 1.51 mmol, 3 equiv) in THF (5 mL) at −78° C. was treated dropwise with n-BuLi (1.44 mmol, 0.58 mL, 2.5 M in hexane, 2.86 equiv). The reaction mixture was stirred at −78° C. for 10 min and allowed to warm to 0° C. over 20 min. The mixture was recooled to −78° C. and HMPA (2.11 mL, 12.1 mmol, 24 equiv) was added followed immediately by the addition of 18 (250 mg, 0.505 mmol) in 2.5 mL of THF. The reaction was stirred at −78° C. for 1.5 h and 24 h at 25° C. before being quenched with the addition of 20 mL of phosphate buffer (pH 7.0). The mixture was extracted with EtOAc (3×50 mL) and the combined organic phase was dried ($Na_2SO_4$) and concentrated in vacuo. Chromatography ($SiO_2$, 2×30 cm, 10% EtOAc-hexane with 2% $Et_3N$) afforded 19 (221 mg, 300 mg theoretical, 74%) as an oil and as a mixture of E- and Z-isomers: $^1$H NMR (CDCl$_3$, 400 MHz) δ8.65 (s, 1H), 8.38 (m, 1H), 7.62 (d, 1H, J=8.1 Hz), 7.49–7.36 (m, 6H), 6.96–6.79 (m, 1H), 6.22–6.07 (m, 1H), 5.28–5.15 (m, 2H), 4.83–4.29 (m, 3H), 3.85–2.77 (m, 2H), 1.98–1.22 (m, 15H); IR (film) $v_{max}$ 2940, 2229, 1704, 1596, 1415, 1367, 1332, 1258, 1225, 1163, 1021, 965, 902, 849, 739, 697 cm$^{-1}$.

5-Benzyloxy-3-(tert-butyloxycarbonyl)-8-cyano-1-[(tetrahydropyranyloxy)methyl]-1,2-dihydro-3H-benz[e]indole (20). A solution of 19 (41 mg, 69 μmol) in freshly distilled benzene (3.5 mL) under Ar was treated with AIBN (2 mg, 0.2 equiv) followed by Bu$_3$SnH (40 mg, 0.014 mmol, 2 equiv). The reaction mixture was warmed at reflux for 2 h, cooled to 25° C., and the solvent was removed under a stream of N$_2$. The residue was azeotroped with THF (1×2 mL). Chromatography ($SiO_2$, 1×20 cm, 10% EtOAc-hexane) afforded 20 (35 mg, 35.5 mg theoretical, 99%) as clear oil: $^1$H NMR (CDCl$_3$, 400 MHz) δ8.29 (d, 1H, J=8.7 Hz), 8.24 and 8.19 (s and d, 1H, J=1.3 Hz), 8.01 (br s, 1H), 7.50 (br d, 1H, J=7.1 Hz), 7.44–7.34 (m, 5H), 5.24 (s, 2H), 4.58 and 4.55 (two br m, 1H), 4.12 (br s, 1H), 4.10 (br s, 1H), 3.96 (dd, 1H, J=5.8, 9.6 Hz), 3.87 (m, 1H), 3.78 (dd, 1H, J=8.9, 9.6 Hz), 3.64 and 3.58 (ddd and dd, 1H, J=3.1, 8.1, 11.3 Hz and 6.2, 9.4 Hz), 3.50–3.38 (m, 1H), 1.73–1.55 (m, 15H); $^{13}$C NMR (CDCl$_3$, 100 MHz) δ155.3, 153.0, 136.3, 129.8, 129.5, 128.6, 128.2, 127.7, 124.5, 123.4, 123.1, 119.5, 110.3, 99.7, 99.1, 80.5, 70.5, 70.1, 62.6, 62.4, 52.8, 38.9, 30.5, 28.4, 28.2, 25.3, 19.5; IR (film) $v_{max}$ 2943, 2226, 1703, 1622, 1592, 1454, 1367, 1328, 1258, 1141, 1033, 967, 854, 736, 697 cm$^{-1}$; FABHRMS (NBA-CsI) m/z 647.1549 (M$^+$+Cs, $C_{31}H_{34}N_2O_5$ requires 647.1552).

5-Benzyloxy-3-(tert-butyloxycarbonyl)-8-cyano-1-(bydroxymethyl)-1,2-dihydro-3H-benz[e]indole (21). From 20: A solution of 20 (35 mg, 69 μmol) in freshly distilled CH$_3$OH (1 mL) was treated with 0.5 mg of Amberlyst-15 ion exchange resin and the reaction mixture was stirred at 45° C. for 5 h. The resin was removed by filtration and washed with CH$_3$OH (1×2 mL). The filtrates were combined and the solvent was removed under a stream of N$_2$. Chromatography ($SiO_2$, 1×20 cm, 20% EtOAc-hexane) afforded 21 (29.7 mg, 29.7 mg theoretical, 100%) as an off-white solid: $^1$H NMR (CDCl$_3$, 400 MHz) δ8.32 (d, 1H, J=8.7 Hz, C6-H), 8.09 (s, 1H, C9-H), 8.02 (br s, 1H, C4-H), 7.51 (d, 1H, J=8.7 Hz, C7-H), 7.43 (m, 5H), 5.25 (s, 2H, CH$_2$Ph), 4.21 (dd, 1H, J=11.5, 2.3 Hz, C2-H), 4.14 (dd, 1H, J=11.5, 8.9 Hz, C2-H), 3.92 (dd, 1H, J=4.0, 10.3 Hz, CHHOH), 3.80 (m, 1H, C1-H), 3.75 (dd, 1H, J=7.2, 10.3 Hz, CHHOH), 1.59 (s, 9H); $^{13}$C NMR (CDCl$_3$, 100 MHz) δ155.5, 153.0, 136.2, 129.7, 128.7, 128.5, 128.2, 127.7, 124.9, 123.5, 123.2, 119.4, 115.0, 110.7, 99.1, 80.5, 70.6, 64.8, 52.5, 47.0, 41.1, 28.4; IR (KBr) $v_{max}$ 3450 (br), 2926, 2226, 1702, 1592, 1458, 1410, 1368, 1328, 1143, 1032, 735, 696 cm$^{-1}$; FABHRMS (NBA) m/z 430.1896 (M$^+$, $C_{26}H_{23}N_2O_4$ requires 430.1893).

From 29: A solution of 29 (341 mg, 0.599 mmol) in THF-HOAc-H$_2$O (3:1:1, 20 mL) was treated with Zn powder (3.13 g, 80 equiv) and the mixture was warmed at 70° C. for 6 h. The Zn powder was removed by filtration through Celite and the mixture was concentrated under vacuum. Chromatography ($SiO_2$, 1.3×13 cm, 0–25% EtOAc-hexane) afforded 21 (188 mg, 258 mg theoretical, 73%), as an off-white solid identical in all respects to that described above.

5-Benzyloxy-3-(tert-butyloxycarbonyl)-1-(chloromethyl)-8-cyano-1,2-dihydro-3H-benz[e]indole (22). A solution of 21 (47 mg, 0.10 mmol) in freshly distilled anhydrous CH$_2$Cl$_2$ (0.35 mL) under Ar was treated sequentially with Ph$_3$P (82 mg, 0.31 mmol, 3 equiv) and CCl$_4$ (91 μL, 0.94 mmol, 9 equiv). The reaction mixture was stirred at 25° C. for 2 h. The solvent was evaporated under a stream of N$_2$. Chromatography ($SiO_2$, 0.8×10 cm, 10% EtOAc-hexane) afforded 22 (49 mg, 49 mg theoretical, 100%) as a white solid: mp 212–214° C.; $^1$H NMR (CDCl$_3$, 400 MHz) δ8.33 (d, 1H, J=8.7 Hz, C6-H), 7.98 (s, 1H, C9-H), 7.70 (br s, 1H, C4-H), 7.50–7.24 (m, 6H), 5.24 (s, 2H), 4.23 (d, 1H, J=11.0 Hz, C2-H), 4.14 (dd, 1H, J=11.0, 8.9 Hz, C2-H), 3.95 (dddd, 1H, J=2.6, 9.2, 11.1, 12.1 Hz, C1-H), 3.83 (dd, 1H, J=3.1, 11.1 Hz, CHHCl), 3.47 (dd, 1H, J=9.9, 11.0 Hz, CHHCl), 1.54 (s, 9H); $^{13}$C NMR (CDCl$_3$, 100 MHz) δ155.9, 144.3, 136.1, 134.3, 133.8, 133.6, 130.4, 128.7, 128.5, 128.4, 128.3, 127.7, 125.1, 123.5, 119.2, 111.1, 99.0, 70.6, 53.1, 46.3., 41.3, 28.3; IR (KBr) $v_{max}$ 2978, 2231, 1692, 1594, 1478, 1409, 1374, 1337, 1166, 1146, 1084, 973, 960, 859, 756, 697 cm$^{-1}$; FABHRMS (NBA) m/z 448.1570 (M$^+$, $C_{26}H_{25}ClN_2O_3$ requires 448.1554).

Resolution of 22. Samples of racemic 22 were resolved by preparative HPLC chromatography on a Diacel Chiralcel-OD column (10 μm, 2×25 cm) using 7% i-PrOH-hexane eluant (7 mL/min). The enantiomers eluted with retention times of 20.70 min (unnatural enantiomer) and 28.54 min (natural enantiomer), α=1.38.

(1S)-22: [α]D$^5$ −9.5 (c 0.5, CHCl$_3$).

ent-(1R)-22: [α]D$^5$ +9.5 (c 0.3, CHCl$_3$).

3-(tert-Butyloxycarbonyl)-1-(chloromethyl)-8-cyano-5-hydroxy-1,2-dihydro-3H-benz[e]indole (23). A solution of 22 (71.5 mg, 0.159 mmol) and 10% Pd-C (40 mg) in anhydrous EtOAc (5 mL) was degassed with a stream of N$_2$ for 30 s. The resulting mixture was placed under an atmosphere of H$_2$ and stirred at 25° C. for 2.5 h. The mixture was diluted with THF (1 mL) and filtered through Celite (EtOAc wash). The solvent was removed in vacuo. Chromatography ($SiO_2$, 1.5×6 cm, 20% EtOAc-hexane) afforded 23 (57.1 mg, 57.1 mg theoretical, 100%) as a white solid: $^1$H NMR (CDCl$_3$, 400 MHz) δ8.25 (d, 1H, J=8.7 Hz, C6-H), 7.97 (s, 1H, C9-H), 7.87 (br s, 1H, C4-H), 7.42 (dd, 1H, J=1.5, 8.7 Hz, C7-H), 6.67 (br s, 1H, OH), 4.23 (d, 1H, J=11.4 Hz, C2-H), 4.14 (dd, 1H, J=8.8, 11.8 Hz, C2-H), 3.95 (m, 1H, C1-H), 3.82 (dd, 1H, J=3.2, 11.3 Hz, CHHCl), 3.46 (dd, 1H, J=9.8, 11.2 Hz, CHHCl), 1.59 (s, 9H); $^{13}$C NMR (CDCl$_3$, 100 MHz) δ154.2, 153.1, 142.9, 129.4, 127.8, 125.2, 123.2, 122.8, 119.3, 114.7, 111.0, 101.7, 82.5, 53.3, 46.3, 41.3, 28.4; IR (film) $v_{max}$ 3315 (br), 2964, 2923, 2227, 1676, 1585, 1421, 1369, 1331, 1235, 1141, 729 cm$^{-1}$; FABHRMS (NBA) m/z 358.1076 (M$^+$+H, $C_{19}H_{19}ClN_2O_3$ requires 358.1084).

(1S)-23: $[\alpha]^{23}_D$ −15 (c 0.08, CHCl$_3$)

ent-(1R)-23: $[\alpha]^{23}_D$ +16 (c 0.09, CHCl$_3$).

N-(tert-Butyloxycarbonyl)-7-cyano-1,2,9,9a-tetrahydrocyclopropa[c]benz[e]indol-4-one (25, N-BOC-CCBI). Method A: A solution of 23 (1.4 mg, 3.91 μmol) in 2:1 DMF-THF (112 μL) at 0° C. was treated with NaH (1.6 mg, 39 μmol, 60% oil dispersion) and the mixture was stirred for 30 min. The solvent was removed under a stream of N$_2$ and vacuum. PTLC (SiO$_2$, 0.25 mm×10×15 cm, 30% EtOAc-hexane) afforded 25 (1.20 mg, 1.26 mg theoretical, 95%) as a white solid: $^1$H NMR (CDCl$_3$, 400 MHz) δ8.29 (d, 1H, J=8.1 Hz, C5-H), 7.64 (dd, 1H, J=1.5, 8.1 Hz, C6-H), 7.14 (d, 1H, J=1.1 Hz, C8-H), 6.87 (br s, 1H, C3-H), 4.03 (m, 2H, C1-H$_2$), 2.81 (dt, 1H, J=4.9, 7.5 Hz, C9a-H), 1.65 (dd, 1H, J=4.7, 7.9 Hz, C9-H), 1.55 (s, 10H, C9-H and C(CH$_3$)$_3$); $^{13}$C NMR (CDCl$_3$, 100 MHz) δ180.4, 159.8, 151.4, 140.9, 135.8, 129.6, 127.7, 125.3, 118.2, 115.0, 108.8, 83.9, 52.9, 33.2, 29.4, 28.1, 23.8; IR (film) $v_{max}$ 2977, 2230, 1727, 1634, 1608, 1396, 1369, 1295, 1277, 1250, 1159, 1131, 843 cm$^{-1}$; UV (THF) $\lambda_{max}$ 259 (ε=22,200), 267 (ε=24,000), 300 nm (ε=12,000); UV (CH$_3$OH) $\lambda_{max}$ 260 (ε=24,700), 266 (ε=25,200), 317 nm (ε=13,400); FABHRMS (NBA) m/z 323.1383 (M$^+$+H, $C_{19}H_{18}N_2O_3$ requires 323.1396).

(+)-N-BOC-CCBI (25): $[\alpha]D^3$ +124 (c 0.04, THF).

ent-(−)-N-BOC-CCBI (25): $[\alpha]D^3$ −121 (c 0.03, THF).

Method B: A solution of 23 (8.6 mg, 24.0 μmol) was dissolved in 1:1 THF-5% aqueous NaHCO$_3$ (2 mL) and the mixture was stirred at 25° C. for 9 h. The THF was removed by evaporation and the product was extracted with EtOAc (4×1 mL). Chromatography (SiO$_2$, 0.8×5 cm, 0–25% EtOAc-hexane gradient) afforded 25 (7.7 mg, 7.7 mg theoretical, 100%) as a white solid identical to that described above.

7-Cyano-1,2,9,9a-tetrahydrocyclopropa[c]benz[e]indol-4-one (26, CCBI). A solution of 23 (2.5 mg, 7.0 μmol) in 4 M HCl-EtOAc (400 μL) was stirred at 25° C. under Ar for 30 min. The solvent was removed under a stream of N$_2$. After being dried in vacuo, the residue 30$^{14}$ was dissolved in THF (200 μL) and treated with 200 μL of 5% aqueous NaHCO$_3$. The reaction mixture was stirred at 25° C. for 5 h before the solvent was removed in vacuo. PTLC (SiO$_2$, 0.25 mm×20×20 cm, 70% THF-hexane) afforded 26 (1.6 mg, 1.6 mg theoretical, 100%) as a cream colored solid: $^1$H NMR (CDCl$_3$, 250 MHz) δ8.30 (d, 1H, J=8.1 Hz, C5-H), 7.61 (dd, 1H, J=1.5, 8.1 Hz, C6-H), 7.11 (d, 1H, J=1.5 Hz, C8-H), 5.77 (s, 1H, C3-H), 4.88 (br s, 1H, NH) 3.87 (dd, 1H, J=5.2, 10.3 Hz, C1-H), 3.69 (d, 1H, J=10.3 Hz, C1-H), 2.92 (dt, J=3.6, 6.7 Hz, 1H, C9a-H), 1.63 (dd, 1H, J=4.3, 7.9 Hz, C9-H), 1.49 (t, 1H, J=4.7 Hz, C9-H); IR (film) $v_{max}$ 3097, 2851, 2227, 1622, 1583, 1519, 1328, 1241, 1092, 809 cm$^{-1}$; 221 nm FABHRMS (NBA) m/z 223.0865 (M$^+$+H, $C_{14}H_{10}N_2O$ requires 223.0871).

(+)-CCBI (26): $[\alpha]D^3$ +64 (c 0.05, THF)

ent-(−)-CCBI (26): $[\alpha]D^3$ −67 (c 0.05, THF).

N-(tert-Butyloxycarbonyl)-4-benzyloxy-7-cyano-1-iodo-2-naphthylamine (27). A solution of 23 (250 mg, 0.67 mmol) in 10 mL of THF-CH$_3$OH (1:1) at −40° C. was treated with a catalytic amount of TsOH-H$_2$O (20 mg) and NIS (180 mg, 0.80 mmol, 1.2 equiv) in 2 mL of THF. The reaction mixture was stirred under Ar at −40° C. for 1 h, and then warmed to 0° C. Additional TsOH-H$_2$O (10 mg) and NIS (75 mg, 0.5 equiv) were added. After the reaction mixture was stirred for 1 h at 25° C., it was quenched with the addition of 5 mL of saturated aqueous NaHCO$_3$ and extracted with Et$_2$O (4×15 mL). The combined organic layer was washed with saturated aqueous Nacl and dried (Na$_2$SO$_4$). PCTLC (2 mm SiO$_2$, 0–10% EtOAc-hexane gradient) afforded 27 (230 mg, 338 mg theoretical, 68%) as a solid: mp 177° C. dec (needles, EtOAc-hexane); $^1$H NMR (CDCl$_3$, 400 MHz) δ8.38 (d, 1H, J=1.5 Hz), 8.26 (d, 1H, J=8.6 Hz), 8.21 (s, 1H), 7.52 (dd, 2H, J=1.0, 7.8 Hz), 7.47 (dd, 1H, J=1.5, 8.6 Hz), 7.45–7.35 (m, 3H), 7.33 (br s, 1H), 5.26 (s, 2H), 1.59 (s, 9H); $^{13}$C NMR (CDCl$_3$, 100 MHz) δ155.4, 152.5, 140.2, 137.0, 135.9, 134.2, 128.7, 128.4, 127.9, 125.1, 125.0, 124.3, 119.0, 112.2, 102.2, 81.8, 78.8, 70.7, 28.3; IR (film) $v_{max}$ 3383, 2978, 2228, 1732, 1600, 1563, 1495, 1397, 1366, 1331, 1230, 1154, 987, 879, 735 cm$^{-1}$; FABHRMS (NBA-CsI) m/z 632.9674 (M$^+$+Cs, $C_{23}H_{21}IN_2O_3$ requires 632.9651).

Anal. Calcd for $C_{23}H_{21}IN_2O_3$: C, 55.21; H, 4.23; N, 5.60. Found: C, 55.28; H, 4.03; N, 5.40.

N-(tert-Butyloxycarbonyl)-N-(2-propenyl)-4-benzyloxy-7-cyano-1-iodo-2-naphthylamine (28). A solution of 27 (160 mg, 0.31 mmol) in anhydrous DMF (5 mL) under Ar was treated with NaH (19 mg, 0.47 mmol, 1.5 equiv, 60% oil dispersion) and the reaction mixture was stirred for 30 min at 0° C. Allyl bromide (194 mg, 139 μL, 1.55 mmol, 5 equiv) was added dropwise over 5 min and the solution was allowed to warm to 25° C. and stirred for 2 h. Saturated aqueous NaHCO$_3$ (10 mL) was added and the aqueous phase was extracted with EtOAc (4×10 mL), dried (Na$_2$SO$_4$) and concentrated. Chromatography (SiO$_2$, 2×15 cm, 10% EtOAc-hexane) afforded 28 (155 mg, 168 mg theoretical, 92%) as a clear oil which crystallized under vacuum: $^1$H NMR (CDCl$_3$, 400 MHz) δ8.60 (s, 1H), 8.38 (d, 1H, J=8.6 Hz), 7.63 (d, 1H, J=8.4 Hz), 7.47–7.34 (m, 5H), 6.90 and 6.79 (two s, 1H), 5.94–5.84 (m, 1H), 5.27 and 5.22 (two d, 2H, J=12.3 Hz), 5.00 (m, 2H), 4.50 (dd, 1H, J=5.3, 14.4 Hz), 3.81 (dd, J=7.0, 14.4 Hz), 1.57 and 1.29 (two s, 9H); $^{13}$C NMR (CDCl$_3$, 100 MHz) δ154.8, 144.9, 138.7, 135.7, 134.8, 133.2, 128.8, 128.3, 127.3, 126.9, 126.8, 124.2, 118.8, 118.4, 117.2, 112.2, 110.7, 80.8, 70.7, 53.3, 52.0, 28.4; IR (film) $v_{max}$ 2977, 2228, 1703, 1593, 1503, 1410, 1368, 1324, 1250, 1223, 1150, 1108, 931, 830, 735, 696 cm$^{-1}$; FABHRMS (NBA-CsI) m/z 672.9948 (M$^+$+Cs, $C_{26}H_{25}IN_2O_3$, requires 672.9964).

Anal. Calcd for $C_{26}H_{25}IN_2O_3$: C, 57.99; H, 4.66; N, 5.18. Found: C, 57.60; H. 4.41; N, 5.27.

5-Benzyloxy-3-(tert-butyloxycarbonyl)-8-cyano-1-[(2',2', 6',6'-tetramethylpiperidino)oxy]methyl-1,2-dihydro-3H-benz[e]indole (29). A solution of 28 (200 mg, 0.37 mmol) in freshly distilled benzene (12 mL) was treated sequentially with TEMPO (3.0 equiv) and Bu$_3$SnH (1.0 equiv). The reaction mixture was warmed to 60° C. After 20 min, an additional equivalent of Bu$_3$SnH was added. After 30 min, additional TEMPO (2 equiv) and Bu$_3$SnH (1.0 equiv) were added. After 20 min, two additional equivalents of TEMPO and Bu$_3$SnH in two separate portions at 15 min intervals were added. After 45 min at 60° C., the solvent was removed by evaporation. PCTLC (4 mm SiO$_2$, 0–25% EtOAc-hexane gradient) afforded 29 (144 mg, 212 mg theoretical, 68%) as a semisolid: $^1$H NMR (CDCl$_3$, 400 MHz) δ8.31 (d, 1H, J=8.7 Hz), 8.19 (s, 1H), 8.01 (s, 1H), 7.53 (d, 2H, J=7.0 Hz), 7.44 (t, 2H, J=7.0 Hz), 7.40 (m, 2H), 5.26 (s, 2H), 4.13 (m, 2H), 3.96 (m, 1H), 3.88 (t, 1H, J=7.0 Hz), 3.80 (m, 1H), 1.59 (s, 9H), 1.39 (m, 4H), h1.10 (s, 3H), 1.03 (s, 6H), 0.96 (s, 3H), 0.92 (t, 2H, J=7.3 Hz); $^{13}$C NMR (CDCl$_3$, 100 MHz)

δ155.2, 152.6, 143.0, 136.4, 129.8, 129.6, 128.7, 128.2, 127.7, 124.5, 123.3, 123.1, 119.5, 117.1, 110.3, 99.1, 81.1, 78.7, 70.5, 59.9, 52.8, 39.6, 39.5, 38.1, 33.0, 28.5, 26.6, 20.4, 20.2, 17.1, 13.6; IR (film) $v_{max}$ 2968, 2926, 1701, 1623, 1586, 1450, 1407, 1352, 1326, 1143, 1041, 855 cm$^{-1}$; FABHRMS (NBA) m/z 570.3330 (M$^+$+H, $C_{35}H_{43}N_3O_4$ requires 570.3332).

seco-CCBI-TMI (34). A solution of 23 (1.5 mg, 4.2 μmol) in 150 μL of 4 M HCl-EtOAc was stirred at 25° C. for 20 min. The solvent was removed under a stream of $N_2$. After being dried in vacuo, the residue, 30 (1.0 mg, 4.2 μmol, 1 equiv; Boger et al. *J. Am Chem. Soc.* 1993 115, 9025), and EDCI (2.9 mg, 12.6 μmol, 3 equiv) were dissolved into anhydrous DMF and the reaction mixture was stirred at 25° C. for 16 h. The solvent was removed under vacuum and the residue was dissolved in THF and loaded directly onto a silica gel column. Chromatography ($SiO_2$, 0.5×6 cm, 50% EtOAc-hexane) afforded 34 (1.7 mg, 2.0 mg theoretical, 85%) as a mustard colored solid: $^1$H NMR (DMSO-$d_6$, 250 MHz) δ11.50 (br s, 1H, NH), 10.86 (s, 1H, OH), 8.53 (s, 1H, C9-H), 8.22 (d, 1H, J=8.7 Hz, C6-H), 8.04 (s, 1H, C4-H), 7.59 (dd, 1H, J=1.51 8.7 Hz, C7-H), 7.07 (d, 1H, J=1.7 Hz, C4'-H), 6.95 (s, 1H, C3'-H), 4.75 (t, 1H, J=10.0 Hz, C2-H), 4.46 (d, 1H, J=10.5 Hz, C2-H), 4.26 (m, 1H, C1-H), 4.04 (dd, 1H, J=2.8, 11.3 Hz, CHHCl), 3.92 (s, 3H), 3.88 (dd, 1H, J=3.9, 11.3, Hz), 3.81 (s, 3H), 3.79 (s, 3H); IR (film) $v_{max}$ 3422, 3122, 2938, 2225, 1587, 1525, 1493, 1454, 1389, 1312, 1235, 1110, 1050, 997, 824, 794 cm$^{-1}$; FABHRMS (NBA) m/z 492.1347 (M$^+$+H, $C_{26}H_{22}ClN_3O_5$ requires 492.1326).

(1S)-34: $[\alpha]_D^5$ −19 (c 0.12, $CHCl_3$).

ent-(1R)-34: $[\alpha]_D^5$ +19 (c 0.12, $CHCl_3$).

CCBI-TMI (35). A solution of 34 (2.2 mg, 4.4 μmol) in 20% DMF-THF (0.25 mL, 0.018 M) under Ar was cooled to 0° C. and NaH (0.5 mg, 3 equiv) was added. The reaction mixture was stirred at 0° C. for 30 min before the solvent was removed under a stream of $N_2$ with care to maintain the 0° C. temperature. PTLC ($SiO_2$, 0.25 mm×10 cm×15 cm, 50% EtOAc-hexane) afforded 35 (2.1 mg, 2.1 mg theoretical, 99%) as a pale yellow solid: $^1$H NMR (DMSO-$d_6$, 400 MHz) δ11.66 (br s, 1H, NH), 8.10 (d, 1H, J=8.3 Hz, C5-H), 7.87 (s, 1H, C8-H), 7.85 (dd, 1H, J=1.5, 8.3 Hz, C6-H), 7.12 (d, 1H, J=2.2 Hz, C4'-H), 6.92 (s, 1H, C3'-H), 6.74 (s, 1H, C3-H), 4.54 (dd, 1H, J=5.6, 10.5 Hz, C1-H), 4.37 (d, 1H, J=10.5 Hz, C1-H), 3.89 (s, 3H), 3.81 (s, 3H), 3.80 (s, 3H), 3.4 (1H, C9a-H masked by $H_2O$), 1.93 (dd, 1H, J=4.0, 7.6 Hz, C9-H), 1.80 (t, 1H, J=5.0 Hz, C9-H); IR (film) $v_{max}$ 3440, 2920, 2850, 2226, 1734, 1653, 1457, 1389, 1307, 1233, 1108 cm$^{-1}$; FABHRMS (NBA) m/z 456.1546 (M$^+$+H, $C_{26}H_{21}N_3O_5$ requires 456.1559).

(+)-CCBI-TMI (35): $[\alpha]_D^3$ +144 (c 0.05, acetone).

ent-(−)-CCBI-TMI (35): $[\alpha]_D^{23}$ −135 (c 0.04, acetone)

seco-CCBI-indole$_2$ (36). A solution of 23 (2.8 mg, 7.8 μmol) in 250 μL of 4 M HCl-EtOAc under Ar was stirred at 25° C. for 20 min. The solvent was removed under a stream of $N_2$ and the crude hydrochloride salt was dried under vacuum. A solution of 24, 31 (2.5 mg, 7.8 μmol, 1.0 equiv) and EDCI (4.5 mg, 23.5 μmol, 3 equiv) were added and the mixture was slurried in 142 μL (0.55 M) of anhydrous DMF. The reaction mixture was stirred at 25° C. for 16 h before the solvent was removed under vacuum. PTLC ($SiO_2$, 0.25 mm×15×20 cm, 30% DMF-toluene) afforded 36 (3.8 mg, 87%) as a tan solid: $^1$H NMR (DMSO-$d_6$, 400 MHz) δ11.76 (s, 1H, NH), 11.71 (s, 1H, NH), 10.85 (s, 1H, OH), 10.16 (s, 1H, NH), 8.55 (s, 1H, C9-H), 8.23 (d, 1H, J=8.6 Hz, C6-H), 8.22 (s, 1H, C4'-H), 8.14 (s, 1H, C4-H), 7.67 (d, 1H, J=7.8 Hz, C4"-H), 7.59 (m, 2H), 7.48 (apparent t, 2H, J=8.8 Hz, C7'- and C7"-H), 7.41 (s, 1H, C3"-H), 7.25 (s, 1H, C3'-H), 7.22 (t, 1H, J=8.1 Hz, C6"-H), 7.06 (t, 1H, J=7.3 Hz, C5"-H), 4.85 (t, 1H, J=10.0 Hz, C2-H), 4.60 (d, 1H, J=11.2 Hz, C2-H), 4.34 (m, 1H, C1-H), 4.06 (d, 1H, J=10.9 Hz, CHHCl), 3.92 (dd, 1H, J=6.9, 11.4 Hz, CHHCl); IR (film) $v_{max}$ 3284, 2921, 2225, 1651, 1589, 1557, 1516, 1411, 1391, 1316, 1230, 1137, 1059, 805, 743 cm$^{-1}$; FABHRMS (NBA) m/z 560.1470 (M$^+$+H, $C_{32}H_{22}ClN_5O_3$ requires 560.1489).

(1S)-36: $[\alpha]_D^5$ +49 (c 0.17, DMF).

ent-(1R)-36: $[\alpha]_D^5$ −44 (c 0.21, DMF).

CCBI-indole$_2$ (37). Method A: A solution of 36 (3.4 mg, 6.10 μmol) in 20% DMF-THF (0.34 mL) under Ar was cooled to 0° C. and treated with NaH (0.8 mg, 18.3 μmol, 60% in oil, 3 equiv). The reaction mixture was stirred for 30 min at 0° C. before the solvent was removed under a stream of $N_2$ with care to maintain the 0° C. temperature. PTLC ($SiO_2$, 0.25 mm×15×20 cm, 15% DMF-toluene) afforded 37 (2.1 mg, 3.2 mg theoretical, 66%) as a tan solid: $^1$H NMR (DMSO-$d_6$, 400 MHz) δ11.87 (s, 1H, NH), 11.72 (s, 1H, NH), 10.18 (s, 1H, NH), 8.23 (s, 1H, C4'-H), 8.12 (d, 1H, J=8.2 Hz, C5-H), 7.88 (s, 1H, C8-H), 7.86 (d, 1H, J=8.2 Hz, C6-H), 7.66 (d, 1H, J=7.9 Hz, C4"-H), 7.61 (dd, 1H, J=8.9, 2.0, Hz, C6'-H), 7.49 (d, 1H, J=8.2, Hz, C7"-H), 7.50 (d, 1H, J=8.9 Hz, C7'-H), 7.41 (s, 1H, C3"-H), 7.31 (s, 1H, C3'-H), 7.20 (t, 1H, J=7.2 Hz, C6"-H), 7.06 (t, 1H, J=7.2 Hz, C5"-H), 7.05 (s, 1H, C3-H), 4.66 (dd, J=4.8, 10.2 Hz, C1-H), 4.53 (d, 1H, J=10.2 Hz, C1-H), 3.37 (m, 1H, C9a-H), 1.91 (dd, 1H, J=4.4, 8.4 Hz, C9-H), 1.78 (t, 1H, J=4.8 Hz, C9-H); IR (neat) $v_{max}$ 3274, 1644, 1601, 1549, 1516, 1454, 1388, 1308, 1265, 1237, 1133, 806, 745 cm$^{-1}$; FABHRMS (NBA) m/z 524.1737 (M$^+$+H, $C_{32}H_{21}N_5O_3$ requires 524.1723).

(+)-CCBI-indole$_2$ (37): $[\alpha]_D^5$ +80 (c 0.04, THF).

ent-(−)-CCBI-indole$_2$ (37): $[\alpha]_D^{25}$ −81 (c 0.09, THF).

Method B: A solution of 36 (2.7 mg, 4.8 μmol) in 1:1 THF-3% aqueous $NaHCO_3$ (700 μL) was stirred at 25° C. for 10 h. The solvent was removed under a stream of $N_2$. PTLC ($SiO_2$, 0.25 mm×20×20 cm, 10% DMF-toluene) afforded 37 (1.7 mg, 2.5 mg theoretical, 68%) as a tan solid.

seco-CCBI-CDPI$_1$ (38). A solution of 23 (4.0 mg, 11.1 μmol) in 500 μL of 4 M HCl-EtOAc was stirred at 0° C. for 30 min. The solvent was removed under a stream of $N_2$ and the crude hydrochloride salt was dried under vacuum. The salt and 32 (3.0 mg, 12.3 μmol, 1.1 equiv) were dissolved in 300 μL of anhydrous DMF and treated with EDCI (6.4 mg, 33.3 μmol, 3 equiv). The reaction mixture was stirred at 25° C. for 14 h. The crude reaction mixture was concentrated and loaded directly onto a preparative TLC plate. Chromatography ($SiO_2$, 0.25 mm×20×15 cm, 20% DMF-toluene) afforded 38 (4.4 mg, 5.4 mg theoretical, 81%) as a pale yellow solid: $^1$H NMR (DMSO-$d_6$, 400 MHz) δ11.68 (s, 1H, NH), 10.88 (br s, 1H, OH), 8.55 (s, 1H, C9-H), 8.22 (d, 1H, J=8.7 Hz, C6-H), 8.13 (s, 1H, C4-H), 8.00 (d, 1H, J=8.9 Hz, C4'-H), 7.59 (d, 1H, J=8.7 Hz, C7-H), 7.23 (d, 1H, J=8.9 Hz, C5'-H), 7.04 (s, 1H, C8'-H), 6.10 (s, 2H, $NH_2$), 4.82 (t, 1H, J=10.1 Hz, C2-H), 4.55 (dd, 1H, J=2.0, 11.0 Hz, C2-H), 4.33 (m, 1H, C1-H), 4.05 (dd, 1H, J=3.1, 11.1 Hz, CHHCl), 3.99 (m, 3H, CHHCl and C2'-$H_2$), 3.26 (m, 2H, C1'-$H_2$ obscured by $H_2O$); IR (film) $v_{max}$ 3350, 2921, 2260, 1723, 1658, 1620, 1590, 1503, 1452, 1414, 1342, 1283, 1252, 1024, 799 cm$^{-1}$; FABHRMS (NBA) m/z 486.1340 (M$^+$+H, $C_{26}H_{20}ClN_5O_3$ requires 486.1333).

(1S)-38: $[\alpha]_D^5$ +37 (c 0.15, DMF).

ent-(1R)-38: $[\alpha]_D^5$ −36 (c 0.22, DMF).

CCBI-CDPI$_1$ (39). A solution of 38 (3.6 mg, 7.4 μmol) in DMF-$H_2O$ (5:2, 600 μL+240 μL) was treated with $KHCO_3$ (20 equiv). The reaction mixture was stirred at 25° C. for 9 h. After removal of solvent, PTLC (SiO$_2$, 0.25 mm×20×20 cm, 20% DMF-toluene) afforded 39 (2.3 mg, 3.3 mg theoretical, 69%) as a tan solid: $^1$H NMR (DMSO-d$_6$, 400 MHz) δ11.74 (s, 1H, NH), 8.12 (d, 1H, J=8.1 Hz, C5-H), 8.02 (d, 1H, J=8.9 Hz, C4'-H), 7.87 (s, 1H, C8-H), 7.85 (d, 1H, J=8.1 Hz, C6-H), 7.21 (d, 1H, J=8.9 Hz, C5'-H), 7.10 (s, 1H, C3-H), 7.01 (s, 1H, C8'-H), 6.13 (s, 2H, NH$_2$), 4.63 (dd, 1H, J=5.1, 10.3 Hz, C1-H), 4.51 (d, 1H, J=10.3 Hz, C1-H), 3.97 (t, 2H, J=8.8 Hz, C2'-H), 3.42 (m, 1H, C9a-H), 3.28 (t, 2H, J=8.8 Hz, C1'-H), 1.91 (dd, 1H, J=4.1, 7.7 Hz, C9-H), 1.76 (t, 1H, J=4.6 Hz, C9-H); IR (neat) v$_{max}$ 3364, 2911, 1652, 1598, 1499, 1455, 1386, 1263, 1130 cm$^{-1}$; FAB-HRMS (NBA) m/z 450.1578 (M+H$^+$, C$_{26}$H$_{19}$N$_5$O$_3$ requires 450.1566).

(+)-CCBI-CDPI$_1$ (39): [α]$^{23}_D$ +124 (c 0.10, DMF).

ent-(−)-CCBI-CDPI$_1$ (39): [α]$^{23}_D$ −117 (c 0.07, DMF).

Aqueous Solvolysis Reactivity. pH 3: N-BOC-CCBI (25, 100 μg) was dissolved in CH$_3$OH (1.5 mL) and mixed with pH 3 aqueous buffer (1.5 mL). The buffer contained 4:1:20 (v:v:v) 0.1 M citric acid, 0.2 M Na$_2$HPO$_4$ and H$_2$O, respectively. The solvolysis solution was sealed and kept at 25° C. protected from light. The UV spectrum was measured at regular intervals every 2 h during the first day, every 12 h for another week, and every 24 h for an additional week. The decrease in the long-wavelength absorption at 322 nm and the increase in the short-wavelength absorption at 268 nm were monitored, FIG. 1. The solvolysis rate constant (k=9.90×10$^{-7}$s$^{-1}$) and half-life (t$_{1/2}$=213 h) were calculated from data recorded at the short wavelength from the least squares treatment (r=0.999) of the slope of the plot of time versus ln[(A$_f$−A$_i$)/(A$_f$−A)], pH 2: Samples of 25 (100 μg) and 26 (50 μg) were dissolved in CH$_3$OH (1.5 mL) and the solutions were mixed with aqueous buffer (pH 2.05, 1.5 mL). The buffer contained 4:1:20 (v:v:v) 1.0 M citric acid, 0.2 M Na$_2$HPO$_4$, and H$_2$O, respectively. Immediately after mixing, the UV spectra of the solutions were measured against a reference solution containing CH$_3$OH (1.5 mL) and the aqueous buffer (1.5 mL) and these readings were used for the initial absorbance values. The solutions were stoppered, protected from the light, and allowed to stand at 25° C. UV spectra were recorded at regular intervals until constant values were obtained for the long and short wavelength absorbances. The solvolysis rate constants were determined from the slope of the lines obtained from linear least squares treatment of plots of ln[(A$_f$−A$_i$)/(A$_f$−A)] versus time using the short wavelength measurements for 25 and long wavelength measurements for 26). The first order rate constant determined under these conditions was 7.94×10$^{-6}$ s$^{-1}$ (t$_{1/2}$=24.2 h, r=0.999) for N-BOC-CCBI (25) and 2.1 10$^{-6}$ s$^{-1}$ (t$_{1/2}$=91.5 h, r=0.99) for CCBI (26).

Solvolysis of N-BOC-CCBI in THF-CH$_3$OH. The solvolysis of N-BOC-CCBI (25) was carried out in THF with 20–500 equiv of CH$_3$OH in the presence of 0.1–0.25 equiv of CF$_3$SO$_3$H. The following is the procedure for the solvolysis of 25 in THF with 20 equiv of CH$_3$OH in the presence of CF$_3$SO$_3$H (0.1 equiv). A stock solution was prepared by addition of CF$_3$SO$_3$H (5.6 μL) and anhydrous CH$_3$OH (502 μL) to anhydrous THF (99.49 mL). A sample of 25 (100 μg) in a UV cell was dissolved in THF (1950 μL) and the THF stock solution (50 μL) which contained CF$_3$SO$_3$H (0.1 equiv) and CH$_3$OH (20 equiv) was added. The solvolysis solution was sealed and UV spectrum was measured with an automated cycle program at regular intervals (10 min/cycle). The decrease in the long wavelength absorption at 313 nm was monitored and the solvolysis was complete after 80 h. The solvolysis rate (k=0.2×10$^{-4}$ s$^{-1}$) and half-life (t$_{1/2}$=9.2 h) were calculated from data recorded at 313 nm from the least squares treatment (r=0.984) of the slope of the plot of time versus ln[(A$_f$−A$_i$)/(A$_f$−A)].

Solvolysis Regioselectivity: 3-(tert-Butyloxycarbonyl)-8-cyano-5-hydroxy-1-methoxymethyl-1,2-dihydro-3H-benz[e]indole (42). A solution of 25 (2.5 mg, 7.8 μmol) in CH$_3$OH (1 mL) containing 0.12 equiv CF$_3$CO$_2$H was stirred at 0° C. for 24 h. NaHCO$_3$ (2.5 mg) was added, and the reaction mixture was stirred at 0° C., warmed to 25° C., filtered through a plug of Celite and concentrated. PTLC (SiO$_2$, 0.25 mm×20×20 cm, 20% EtOAc-hexane) provided 42 as a semisolid (2.3 mg, 2.7 mg theoretical, 85%, 95% based on conversion) and recovered 25 (0.3 mg, 12%). For 42: $^1$H NMR (CDCl$_3$, 400 MHz) δ8.23 (d, 1H, J=8.7 Hz), 8.08 (s, 1H), 7.88 (br s, 1H), 7.40 (dd, 1H, J=1.4, 8.7 Hz), 6.79 (br s, 1H), 4.10 (apparent d, 2H, J=7.9 Hz), 3.85 (m, 1H), 3.65 (dd, 1H, J=4.6, 9.4 Hz), 3.39 (s, 3H), 3.35 (t, 1H, J=9.2 Hz), 1.59 (s, 9H); IR (film) v$_{max}$ 3339, 2974, 2925, 1704, 1674, 1620, 1586, 1452, 1418, 1369, 1329, 1250, 1220, 1137 cm$^{-1}$; FABHRMS (NBA-NaI) m/z 377.1488 (M+Na, C$_{20}$H$_{22}$N$_2$O$_4$ requires 377.1477).

DNA Alkylation Studies: selectivity and Efficiency. General procedures, the preparation of singly $^{32}$P 5' end-labeled double stranded DNA, the agent binding studies, gel electrophoresis, and autoradiography were conducted according to standard procedures. Eppendorf tubes containing the 5' end-labeled DNA (9 μL) in TE buffer (10 mM Tris, 1 mM EDTA, pH 7.5) were treated with the agent in DMSO (1 μL at the specified concentration). The solution was mixed by vortexing and brief centrifugation and subsequently incubated at 4 or 25° C. for 24 h (natural enantiomers) and 25 or 37° C. (unnatural enantiomers) for 72 h. The covalently modified DNA was separated from unbound agent by EtOH precipitation and resuspended in TE buffer (10 μL). The solution of DNA in an Eppendorf tube sealed with parafilm was warmed at 100° C. for 30 min to induce cleavage at the alkylation sites, allowed to cool to 25° C. and centrifuged. Formamide dye (0.03% xylene cyanol FF, 0.03% bromophenol blue, 8.7% Na$_2$EDTA 250 mM) was added (5 μL) to the supernatant. Prior to electrophoresis, the sample was denatured by warming at 100° C. for 5 min, placed in an icebath, and centrifuged, and the supernatant (3 μL) was loaded directly onto the gel. Sanger dideoxynucleotide sequencing reactions were run as standards adjacent to the reaction samples. Polyacrylamide gel electrophoresis (PAGE) was run on an 8% sequencing gel under denaturing conditions (8 M urea) in TBE buffer (100 mM Tris, 100 mM boric acid, 0.2 mM Na$_2$EDTA) followed by autoradiography.

DNA Alkylation Relative Rate of (+)-CCBI-TMI (35), (+)-CBI-TMI, and (+)-MCBI-TMI. Following the procedure detailed above, Eppendorf tubes containing 5' end-labeled w794 DNA (9 μL) in TE buffer (pH 7.5) were treated with (+)-CCBI-TMI (35), (+)-CBI-TMI, or (+)-MCBI-TMI (1 μL, 10$^{-6}$ M in DMSO). The solutions were mixed and incubated at 25° C. for 2, 4, 6, 9, 12, 15, and 24 h, respectively. Subsequent isolation of the alkylated DNA by EtOH precipitation, resuspension in TE buffer (10 μL, pH 7.5), thermolysis (30 min, 100° C.), PAGE, and autoradiography were conducted as detailed above. Relative rates for alkylation at the w794 high-affinity 5'-AATTA site were derived from the slopes of the plots of percent integrated optical density (IOD) of the high-affinity alkylation cleavage bands versus time.

DNA Alkylation Relative Rate of (+)-CCBI-indole$_2$ (37), (+)-CBI-indole$_2$, and (+)-MCBI-indole$_2$. Following the procedure detailed above, Eppendorf tubes containing 5' end-labeled w794 DNA (9 μL) in TE buffer (pH 7.5) were treated with (+)-CCBI-indole$_2$ (37), (+)-CBI-indole$_2$, and (+)-MCBI-indole$_2$ (1 μL, 10$^{-6}$ M in DMSO). The solutions were mixed and incubated at 25° C. for 2, 4, 6, 9, 12, 15, and 24 h, respectively. Subsequent isolation of the alkylated DNA by EtOH precipitation, resuspension in TE buffer (10 μL, pH 7.5), thermolysis (30 min, 100° C.), PAGE, and autoradiography were conducted as detailed above. Relative rates for alkylation at the w794 high-affinity 5'-AATTA site were derived from the slopes of the plots of percent integrated optical density (IOD) of the high-affinity alkylation cleavage bands versus time.

1-Chloromethyl-3-(2-ethoxy-1,2-dioxoethyl)-5-hydroxy-1,2-dihydro-3H-benz[e]indole (114). A sample of 113 freshly generated from 112 (3.6 mg. 0.01 mmol; Boger, D. L.; Colletti, S. L.; Honda, T.; Menezes, R. F. *J. Am. Chem. Soc.* 1994, 116, 5607. Boger, D. L.; Colletti, S. L.; Teramoto, S.; Ramsey, T. R.; Zhou, *J. Bioorg. Med. Chem.* 1995, 3, 1281) by treatment with 3.6 N HCl-EtOAc (25° C., 30 min) was treated with ethyl oxalyl chloride (3.0 mg, 0.022 mmol, 2.0 equiv) in THF (0.5 mL) in the presence of NaHCO$_3$ (2.7 mg, 0.03 mmol, 3.0 equiv) and the reaction mixture was stirred at 25° C. for 2 h. The solvent was removed under a stream of N$_2$. Chromatography (SiO$_2$ 0.8×5 cm, 50% EtOAc-hexane) afforded 114 (3.6 mg, 3.6 mg theoretical, 100%) as a solid: $^1$H NMR (CDCl$_3$, 400 MHz) 9.13 (br s, 1H), 8.37 (s, 1H), 8.31 (d, J=8.3 Hz, 1H), 8.68 (d, J=8.2 Hz, 1H), 7.54 (dd, J=7.2, 8.3 Hz, 1H), 7.44 (dd, J=7.2, 8.2 Hz, 1H), 4.40–4.60 (m, 4H), 4.07 (m, 1H), 3.94 (dd, J=3.1, 11.3 Hz, 1H), 3.43 (t, J=11.1 Hz, 1H), 1.56 (t, J=7.2 Hz, 3H); IR (neat)$_{max}$ 3239, 1732, 1640, 1581, 1438, 1397, 1360, 1245, 1227, 1121, 854, 776, 753 cm$^{-1}$; FABHMS (NBA-NaI) m/z 356.0678 (M+Na$^+$, C$_{17}$H$_{16}$ClNO$_4$ requires 356.0666).

Natural (1S)-114: [a]$^{25}_D$ –81 (c 0.2, CHCl$_3$).

Ent-(1R)-114: [a]$^{25}_D$ +90 (c 0.25, CHCl$_3$).

1-Chloromethyl-3-(4-ethoxy-1,4-dioxobutyl)-5-hydroxy-1,2-dihydro-3H-benz[e]indole (115). A sample of 113 freshly generated from 12$^{15}$ (5.3 mg, 0.016 mmol) by treatment with 3.6 N HCl-EtOAc (25° C., 30 min) was treated with ethyl succinyl chloride (2.6 mg, 0.016 mmol, 1.0 equiv) in THF (0.5 mL) in the presence of NaHCO$_3$ (3.3 mg, 0.04 mmol, 2.5 equiv) and the mixture was stirred at 25° C. for 1 h. The solvent was removed under a stream of N$_2$. PTLC (SiO$_2$, 0.25 mm×20×20 cm, 50% EtOAc-hexane) afforded 115 (5.8 mg, 5.8 mg theoretical, 100%) as a solid: $^1$H NMR (acetone-d$_6$, 400 MHz) 9.20 (s, 1H), 8.20 (d, J=8.4 Hz, 1H), 8.05 (s, 1H), 7.81 (d, J=8.4 Hz, 1H), 7.50 (dd, J=2.9, 8.4 Hz, 1H), 7.34 (dd, J=7.9, 8.4 Hz, 1H), 4.36 (m, 1H), 4.18 (m, 1H), 4.10 (q, J=7.2 Hz, 2H), 4.02 (dd, J=3.1, 11.1 Hz, 1H), 3.72 (dd, J=9.1, 11.1 Hz, 1H), 2.83 (t, J=6.4 Hz, 2H), 2.66 (t, J=6.4 Hz, 2H), 1.22 (t, J=7.2 Hz, 3H); IR (neat)$_{max}$ 3290, 1718, 1635, 1578, 1473, 1430, 1395, 1382, 1246, 1181, 1132, 861 770, 748 cm$^{-1}$; FABHRMS (NBA-NaI) m/z 362.1148 (M+H$^+$, C$_{19}$H$_{20}$ClNO$_4$ requires 362.1159).

Natural (1S)-115: [ ]$^{25}_D$ –32 (c 0.3, THF).

Ent-(1R)-15: [ ]$^{25}_D$ +39 (c 0.15, THF).

N$^2$-(4-ethoxy-1,4-dioxobutyl)-1,2,9,9a-tetrahydrocyclopropa[c]benz[e]indole-4-one (116). A sample of 115 (3.5 mg, 9.7 μmol) was placed in 5% aqueous NaHCO$_3$-THF (1:1, 500 μL) and the mixture was stirred at 25° C. for 9 h before the solvent was removed under a stream of N$_2$. PTLC (SiO, 0.25 mm×20×20 cm, 50% THF-hexane) afforded 116 (2.5 mg, 3.2 mg theoretical, 79%) as a white solid: $^1$H NMR (acetone-d$_6$, 400 MHz) 8.07 (d, J=7.8 Hz, 1H), 7.54 (dd, J=7.6, 7.8 Hz, 1H), 7.39 (dd, J=7.6, 7.8 Hz, 1H), 7.12 (d, J=7.8 Hz, 1H), 4.28 (m, 2H), 4.09 (q, J=7.1 Hz, 2H), 3.10 (m, 1H), 2.81 (t, J=6.8 Hz, 2H), 2.62 (t, J=6.8 Hz, 2H), 1.70 (dd, J=4.2, 4.8 Hz, 1H), 1.54 (apparent t, J=4.6 Hz, 1H), 1.21 (t, J=7.1 Hz, 3H); IR (neat)$_{max}$ 2933, 1727, 1693, 1624, 1594, 1560, 1402, 1389, 1368, 1235, 1167, 1017, 859, 782 cm$^{-1}$; FABHRMS (NBA) m/z 326.1382 (M+H$^+$, C$_{19}$H$_{19}$NO$_4$ requires 326.1392).

Natural (+)-116: [ ]$^{25}_{D\ +133}$ (c 0.13, THF).

Ent-(–)-116: [ ]$^{25}_D$ –150 (c 0.12, THF).

3-[2'-(2-(2-Ethoxy-1,2-dioxoethyl)aminoethyl)-2,4'-bithiazole-4-carboxamido]propyl Methyl Sulfide (118). A solution of 117 (13.7 mg, 0.04 mmol;Boger, D. L.; Colletti, S. L.; Honda, T.; Menezes, R. F. *J. Am. Chem. Soc.* 1994, 116, 5607. Boger, D. L.; Colletti, S. L.; Teramoto, S.; Ramsey, T. R.; Zhou, *J. Bioorg. Med. Chem.* 1995, 3, 1281) in DMF (0.04 mL) was treated with ethyl oxalyl chloride (9.1 μL, 0.08 mmol, 2.0 equiv) and the mixture was stirred under Ar at 25° C. for 20 h before the solvent was removed under vacuum. Chromatography (SiO$_2$, 0.8×12 cm, 70% EtoAc-hexane) afforded 118 (12.7 mg, 17.7 mg theoretical, 72%) as an off white solid: R$_f$ 0.62 (SiO$_2$, 1 1 6.5 cm, 10% CH$_3$OH—CH$_2$Cl$_2$); $^1$H NMR (CDCl$_3$, 400 MHz) 8.11 (s, 1H), 8.06 (t, J=6.7 Hz, 1H), 7.87 (s, 1H), 7.55 (t, J=6.1 Hz, 1H), 4.35 (q, J=7.2 Hz, 2H), 3.85 (dt, J=6.1, 6.3 Hz, 2H), 3.58 (dt, J=6.7, 6.7 Hz, 2H), 3.28 (t, J=6.3 Hz, 2H), 2.60 (t, J=7.2 Hz), 2.11 (s, 3H), 1.95 (tt, J=7.2, 6.7 Hz, 2H); IR (neat)$_{max}$ 3325, 3113, 2920, 1733, 1693, 1658, 1545, 1480, 1436, 1371, 1297, 1205, 1114, 1053, 1018, 805, 766 cm$^{-1}$; FABHRMS (NBA) m/z 443.0889 (M+H$^+$, C$_{17}$H$_{22}$N$_4$O$_4$S$_3$ requires 443.0881).

3-[2'-(2-(2-Hydroxy-1,2-dioxoethyl)aminoethyl)-2,4'-bithiazole-4-carboxamido]propyl Methyl Sulfide (119). A solution of 118 (12.7 mg, 0.029 mmol) in THF-H$_2$O—CH$_3$OH (3:1:1, 0.45 mL) was treated with LiOH (6.0 mg, 0.14 mmol, 5.0 equiv) and the mixture was stirred at 25° C. for 2 h before the solvent was removed in vacuo. The crude product was dissolved in H$_2$O and was acidified to pH 0.5 with the addition of 10% aqueous HCl. The product was extracted with 30% isopropanol-CHCl$_3$ (7×1.2 mL), and the combined extracts were concentrated to afford 119 (11.9 mg, 11.9 mg theoretical, 100%) as an off white solid which was sufficiently pure to use in the next reaction directly: $^1$H NMR (CD$_3$OD, 400 MHz) 8.16 (s, 1H), 8.14 (s, 1H), 3.71 (t, J=6.8 Hz, 2H), 3.51 (t, J=7.0 Hz, 2H), 3.30 (t, 2H, overlapped with CH$_3$OH), 2.58 (t, J=7.2 Hz, 2H), 2.10 (s, 3H), 1.92 (tt, J=7.2, 7.0 Hz, 2H); IR (film)$_{max}$ 3346, 3102, 2916, 1656, 1543, 1480, 1436, 1362, 1294, 1240, 1128, 1054 cm$^{-1}$; FAB-HRMS (NBA) m/z (M+$^+$H, C$_{15}$H$_{18}$N$_4$O$_4$S$_3$ requires 415.0568).

3-[2'-(2-(2-(1-Chloromethyl-5-hydroxy-1,2-dihydro-3H-benz[e]indol-3-yl)-1,2-dioxoethyl)aminoethyl)-2,4'-bithiazole-4-carboxamido]propyl Methyl Sulfide (105). A sample of 113 freshly generated from 12$^{15}$ (5.3 mg, 0.016 mmol, 1.5 equiv) by treatment with 4 N HCl-EtOAc (25° C., 30 min) was treated with 119 (4.4 mg, 0.011 mmol, 1.0 equiv) and EDCI (3.0 mg, 0.016 mmol, 1.5 equiv) in DMF (0.2 mL) under Ar and the mixture was stirred at 25° C. for 17 h. The DMF was removed and the crude product was placed in H$_2$O (0.2 mL). The aqueous phase was extracted with CHCl$_3$ (3×0.3 mL) and 50% hexane-EtOAc (2×0.3 mL). The combined organic extracts were concentrated in vacuo. PCTLC (SiO$_2$, 0.25 mm×20×20 cm, 5% CH$_3$OH—CH$_2$Cl$_2$) afforded 105 (2.9 mg, 6.7 mg theoretical, 43%) as a tan solid: $^1$H NMR (CDCl$_3$, 400 MHz) 8.34 (t, J=6.1 Hz, 1H), 8.22 (d, J=8.2 Hz, 1H), 8.14 (s, 1H), 7.95 (s, 1H), 7.71

(d, J=8.3 Hz, 1H), 7.55 (m, 2H), 7.43 (dd, J=8.1, 7.1 Hz, 1H), 3.89 (m, 3H), 3.53 (dt, J=5.9, 6.1 Hz, 2H), 3.45 (t, J=11.0 Hz, 1H), 3.38 (t, J=6.4 Hz, 2H), 2.56 (t, J=7.2 Hz, 2H), 2.09 (s, 3H), 1.90 (tt, J=7.2, 6.1 Hz, 2H); IR (neat)$_{max}$ 3322, 3115, 2917, 2842, 1645, 1574, 1541, 1518, 1410, 1391, 1358, 1254, 1123, 1019, 854, 806, 759 cm$^{-1}$; FABHRMS (NBA) m/z 630.1054 (M+H$^+$, $C_{28}H_{28}ClN_5O_4S_3$ requires 630.1070).

Natural (1S)-105: [ ]$^{25}_D$ −22 (c 0.05, CHCl$_3$).

Ent-(1R)-105: [ ]$^{25}_D$ +22 (c 0.05, CHCl$_3$).

3-[2'-(2-(2-(1-Chloromethyl-5-hydroxy-1,2-dihydro-3H-benz[e]indol-3-yl)-1,2-dioxoethyl)aminoethyl)-2,4'-bithiazole-4-carboxamido]propyl Dimethyl Sulfoxide (106). Samples of 106 (1.5 mg, 22%) were obtained as byproducts in the preparation of 105. For 106: $^1$H NMR (CDCl$_3$, 400 MHz) 8.66 (m, 1H), 8.25 (d, J=8.5 Hz, 1H), 8.07 (s, 1H), 7.91 (m, 1H), 7.76 (s, 1H), 7.68 (d, J=8.3 Hz, 1H), 7.52 (dd, J=8.2, 8.2 Hz, 1H), 7.40 (dd, J=7.7, 7.5 Hz, 1H), 4.96 (dt, J=12.7, 1.8 Hz, 1H), 4.63 (dt, J=12.7, 2.4 Hz, 1H), 4.02 (m, 1H), 3.89 (m, 3H), 3.67 (m, 3H), 3.42 (dd, J=10.0, 11.0 Hz, 1H), 3.35 (m, 3H), 2.64 (s, 3H), 2.19 (m, 2H); IR (neat)$_{max}$ 3324, 3272, 3113, 3012, 2920, 2851, 1643, 1580, 1548, 1516, 1480, 1446, 1412, 1395, 1360, 1290, 1249, 1149, 1122, 1059, 1005, 948, 855 812, 755 cm$^{-1}$; FABHRMS (NBA) m/z 777.9980 (M+Cs$^+$, $C_{28}H_{28}ClN_5O_5S_3$ requires 777.9995).

Natural (1S)-106: [ ]$^{25}_D$ −10 (c 0.07, CHCl$_3$).

Ent-(1R)-106: [ ]$^{25}_D$ +10 (c 0.050, CHCl$_3$).

3-[2'-(2-(2-(1-Chloromethyl-5-hydroxy-1,2-dihydro-3H-benz[e]indol-3-yl)-1,2-dioxoethyl)aminoethyl)-2,4'-bithiazole-4-carboxamido]propyl Dimethyl Sulfonium Iodide (107). A solution of 105 (2.9 mg, 0.0046 mmol) in DMF (0.2 mL) was treated with CH$_3$I (29 μL, 0.46 mmol, 100 equiv) and the mixture was stirred under Ar at 25° C. for 67 h. Evaporation of solvent and trituration with CHCl$_3$ (5×0.1 mL) afforded pure 108 (3.6 mg, 3.6 mg theoretical, 100%) as a yellow solid: $^1$H NMR (CD$_3$OD, 400 MHz) 8.19 (m, 3H), 7.86 (s, 1H), 7.75 (d, J=8.3 Hz, 1H), 7.52 (m, 1H), 7.37 (m, 1H), 4.59 (dd, J=12.2, 2.0 Hz, 1H), 4.42 (dd, J=12.1, 8.6 Hz, 1H), 4.07 (m, 1H), 3.90 (dd, J=11.2, 3.2 Hz, 1H), 3.81 (t, J=6.7 Hz, 2H), 3.57 (m, 3H), 3.39 (m, 4H), 2.94 (s, 6H), 2.15 (tt, J=6.7, 6.6 Hz, 2H); IR (neat)$_{max}$ 3426, 3015, 2769, 1646, 1467, 1431, 1410, 1390, 1251, 1112, 1051, 1015 cm$^{-1}$; FABHRMS (NBA) m/z 644.1238$^+$ (M, $C_{29}H_{31}ClN_5O_4S_3$ requires 644.1227).

Natural (1S)-107: [ ]$^{25}_D$ −8.3 (c 0.08, CH$_3$OH).

Ent-(1R)-107: [ ]$^{25}_D$ +8.5 (c 0.06, CH$_3$OH).

1-Chloromethyl-5-hydroxy-1,2-dihydro-3H-3-[(N-(4-tert-butyloxy-1,4-dioxobutyl)]-benz[e]indole (120). A freshly prepared sample of 113 generated by treatment of 112 (10 mg, 0.03 mmol; Boger, D. L.; McKie, J. A. J. Org. Chem. 1995, 60, 1271) with 4 N HCl-EtOAc (25° C., 30 min) in DMF (0.75 mL) was treated with tert-butyl hemisuccinate (7.8 mg, 0.045 mmol, 1.5 equiv) and EDCI (17.3 mg, 0.09 mmol, 3.0 equiv) and the mixture was stirred under Ar at 25° C. for 21 h. The solvent was removed under vacuum. Chromatography (SiO$_2$, 8×10 cm, 7% Et$_2$O—CH$_2$Cl$_2$) afforded 120 (4.7 mg, 11.7 mg theoretical, 40%): $^1$H NMR (CDCl$_3$, 400 MHz) 9.25 (s, 1H), 8.30 (d, J=8.3 Hz, 1H), 8.20 (s, 1H), 7.58 (d, J=8.3 Hz, 1H), 7.49 (dd, J=7.0, 8.3 Hz, 1H) 7.37 (dd, J=7.0, 8.3 Hz, 1H), 4.28 (m, 2H), 3.89 (m, 2H), 3.36 (t, J=10.6 Hz, 1H), 2.81 (m, 4H), 1.45 (s, 9H); IR (neat)$_{max}$ 3133, 2971, 1726, 1649, 1582, 1476, 1451, 1429, 1415, 1388, 1375, 1334, 1249, 1145, 844, 754 cm$^{-1}$; FABHRMS (NBA-NaI) m/z 389.1399 (M$^+$, $C_{21}H_{24}ClNO_4$ requires 389.1394).

Natural (1S)-120: [ ]$^{25}_D$ −58 (c 0.1, CHCl$_3$).

Ent-(1R)-120: [ ]$^{25}_D$ +60 (c 0.4, CHCl$_3$).

3-[2'-(2-(2-(1-Chloromethyl-5-hydroxy-1,2-dihydro-3H-benz[e]indol-3-yl)-1,4-dioxobutyl)aminoethyl)-2,4'-bithiazole-4-carboxamido]propyl Methyl Sulfide (108). A sample of 120 (3.7 mg, 0.009 mmol) was treated with formic acid (2 mL) at 25° C. for 3 h. The formic acid was removed by evaporation under a stream of N$_2$. The crude acid 121 in DMF (0.35 mL) was treated with 117 (3.9 mg, 0.011 mmol, 1.2 equiv; Boger, D. L.; Colletti, S. L.; Honda, T.; Menezes, R. F. J. Am. Chem. Soc. 1994, 116, 5607. Boger, D. L.; Colletti, S. L.; Teramoto, S.; Ramsey, T. R.; Zhou, J. Bioorg. Med. Chem. 1995, 3, 1281), EDCI (5.5 mg, 0.029 mmol, 3.0 equiv) and the mixture was stirred under Ar at 25° C. for 38 h before the solvent was removed in vacuo. PCTLC (SiO$_2$, 0.25 mm×20 cm×20 cm, 3% CH$_3$OH—CH$_2$Cl$_2$) afforded 108 as a light yellow solid (2.3 mg, 6.2 mg theoretical, 37%): $^1$H NMR (CD$_3$OD, 400 MHz) 8.15 (d, J=8.3 Hz, 1H), 8.10 (s, 1H), 8.06 (s, 1H), 7.83 (s, 1H), 7.70 (d, J=7.9 Hz, 1H), 7.48 (dd, J=7.0, 7.9 Hz, 1H), 7.32 (dd, J=7.0, 8.3 Hz, 1H), 4.27 (m, 2H), 4.05 (m, 1H), 3.94 (dd, J=3.0, 11.0 Hz, 1H), 3.65 (t, J=6.4 Hz, 2H), 3.58 (dd, J=9.0, 11.0 Hz, 1H), 3.48 (t, J=6.8 Hz, 2H), 3.26 (m, 2H, overlapped with solvent), 2.70–2.90 (m, 1H), 2.59 (m, 2H), 2.09 (s, 3H), 1.91 (tt, J=6.8, 7.1 Hz, 2H); IR (neat)$_{max}$ 3302, 3112, 2911, 1643, 1574, 1542, 1479, 1416, 1389, 1363, 1247, 1131, 756 cm$^{-1}$; FABHRMS (NBA) m/z 790.0330$^+$ (M+Cs, $C_{30}H_{32}ClN_5O_4S_3$ requires 790.0359).

Natural (1S)-108: [ ]$^{25}_D$ +10 (c 0.13, CHCl$_3$).

3-[2'-(2-(4-(1-Chloromethyl-5-hydroxy-1,2-dihydro-3H-benz[e]indol-3-yl)-1,4-dioxobutyl)aminoethyl)-2,4'-bithiazole-4-carboxamido]propyl Dimethyl Sulfonium Iodide (109). A solution of 108 (1.9 mg, 0.003 mmol) in DMF (0.19 mL) was treated with CH$_3$I (41 mg, 0.29 mmol, 100 equiv) in DMF and the mixture was stirred under Ar at 25° C. for 120 h. Additional CH$_3$I (41 mg, 0.29 mmol, 100 equiv) was added and after an additional 22 h, DMF was removed in vacuo. The residue was purified by trituration with CHCl$_3$ (7×0.3 mL) to afford 109 (2.3 mg, 2.3 mg theoretical, 100%): $^1$H NMR (DMSO-d$_6$, 400 MHz) 10.36 (s, 1H), 8.68 (t, J=6.1 Hz, 1H), 8.31 (s, 1H), 8.20 (t, J=5.7 Hz, 1H), 8.16 (s, 1H), 8.09 (d, J=8.4 Hz, 1H), 7.97 (s, 1H), 7.80 (d, J=8.4 Hz, 1H), 7.51 (dd, J=7.6, 8.4 Hz, 1H), 7.33 (dd, J=7.6, 8.4 Hz, 1H), 4.35 (t, J=10.7 Hz, 1H), 4.18 (m, 2H), 4.01 (dd, J=1.9, 11.0 Hz, 1H), 3.80 (dd, J=7.9, 10.8 Hz, 1H), 3.40–3.60 (m, 8H, overlapped with H$_2$O in DMSO-d$_6$), 3.33 (t, J=7.6 Hz, 2H), 3.22 (t, J=6.9 Hz, 2H), 2.09 (s, 6H), 2.01 (tt, J=7.4, 7.6 Hz, 2H); IR (neat)$_{max}$ 3422, 1651, 1646, 1635, 1557, 1539, 1521, 1506, 1473, 1457, 1418, 1056, 1028, 1008 cm$^{-1}$; FABHRMS (NBA-CsI) m/z 672.1566 (M$^+$, $C_{31}H_{35}ClN_5O_4S_3$ requires 672.1540).

Natural (1S)-109: [ ]$^{25}_D$ −12 (c 0.18, DMSO).

3-[2'-(2-((4-(1-Chloromethyl-5-hydroxy-1,2-dihydro-3H-benz[e]indol-3-yl)-1,4-dioxobutyl)-L-threonyl)aminoethyl)-2,4'-bithiazole-4-carboxamido]propyl Methyl Sulfide (110). A sample of 120 (3.6 mg, 0.009 mmol) was treated with formic acid (1 mL) at 25° C. for 1.5 h before the solvent was removed by a stream of N$_2$. Crude 121 in DMF (0.3 mL) was treated with 122 (4.0 mg, 0.009 mmol, 1.0 equiv; Boger, D. L.; Colletti, S. L.; Honda, T.; Menezes, R. F. J. Am. Chem. Soc. 1994, 116, 5607. Boger, D. L.; Colletti, S. L.; Teramoto, S.; Ramsey, T. R.; Zhou, J. Bioorg. Med. Chem. 1995, 3, 1281), EDCI (4.4 mg, 0.023 mmol, 2.5 equiv) and HOBt (1.4 mg, 0.01 mmol, 1.1 equiv) and the mixture was stirred at 25° C. for 47 h. The solvent was removed in vacuo. PCTLC (SiO$_2$, 0.25 mm×20×20 cm, 5%

CH$_3$OH—CH$_2$Cl$_2$) afforded 110 (4.5 mg, 6.9 mg theoretical, 65%) as an orange solid: $^1$H NMR (CD$_3$OD, 400 MHz) 8.06 (d, J=8.4 Hz, 1H), 7.94 (s, 1H), 7.91 (s, 1H), 7.75 (s, 1H), 7.64 (d, J=8.3 Hz, 1H), 7.44 (dd, J=7.7, 8.3 Hz, 1H), 7.27 (dd, J=7.7, 8.4 Hz, 1H), 4.40 (m, 1H), 4.27 (m, 3H), 4.05 (m, 1H), 3.96 (dd, J=3.1, 11.2 Hz, 1H), 3.06 (m, 1H), 2.78 (m, 2H), 2.55 (t, J=7.0 Hz, 3H), 2.09 (s, 3H), 1.89 (tt, J=7.0, 7.2 Hz, 2H), 1.22 (d, J=5.8 Hz, 3H); IR (neat)$_{max}$ 3320, 2924, 1652, 1637, 1579, 1545, 1478, 1420, 1246, 749 cm$^{-1}$; FABHRMS (NBA-CsI) m/z 891.0827 (M$^+$+Cs, C$_{34}$H$_{39}$ClN$_6$O$_6$S$_3$ requires 891.0836).

Natural (1S)-110: [ ]$^{25}_D$ −218 (c 0.2, CHCl$_3$).

3-[2'-(2-((4-(1-Chloromethyl-5-hydroxy-1,2-dihydro-3H-benz[e]indol-3-yl)-1,4-diooxobutyl)-L-threonyl) aminoethyl)-2,4'-bithiazole-4-carboxamido]propyl Dimethyl Sulfonium Iodide (111). A solution of 110 (2.2 mg, 0.003 mmol) in DMF (0.17 mL) was treated with CH$_3$I (41.2 mg, 0.29 mmol, 100 equiv) and the mixture was stirred under Ar at 25° C. for 88 h. The solvent was removed by evaporation. Pure 110 was obtained by trituration with CHCl$_3$ (8×0.5 mL) to afford 111 (2.6 mg, 2.6 mg theoretical, 100%) as a yellow solid: $^1$H NMR (DMSO-d$_6$, 400 MHz) 10.33 (s, 1H), 8.63 (t, J=5.9 Hz, 1H), 8.27 (s, 1H), 8.08 (s, 1H), 8.07 (d, J=8.3 Hz, 1H), 8.00 (t, J=5.7 Hz, 1H), 7.94 (s, 1H), 7.83 (d, J=8.4 Hz, 1H), 7.77 (d, J=8.3 Hz, 1H), 7.47 (dd, J=7.5, 8.3 Hz, 1H), 7.30 (dd, J=7.5, 8.4 Hz, 1H), 4.34 (t, J=10.4 Hz, 1H), 3.56 (m, 1H), 3.40–3.50 (m, 8H, overlapped with H$_2$O in DMS0-d$_6$), 3.30 (t, J=7.5 Hz, 2H), 3.15 (t, J=6.8 Hz, 2H), 2.87 (s, 6H), 1.98 (tt, J=6.6, 6.8 Hz, 2H), 1.03 (d, J=6.4 Hz, 3H): IR (neat)$_{max}$ 3317, 1648, 1633, 1555, 1535, 1516, 1502, 1473, 1453, 1414 cm$^{-1}$; FABHRMS (NBA) m/z 773.2050 (M$^+$, C$_{35}$H$_{42}$ClN$_6$O$_6$S$_3$ requires 773.2017).

Natural (1S)-111: [ ]$^{25}_D$ −9.2 (c 0.1, DMSO).

DNA Alkylation of w794 DNA. Eppendorf tubes containing the 5'-end labeled DNA (9 μL) in TE buffer (10 mM Tris, 1 mM EDTA, pH 7.2) were treated with the agent in DMSO (1 μL at the specified concentration). The solution was mixed by vortexing and brief centrifugation and subsequently incubated at 37° C. for 76 h (both enantiomers of 105, 106, 107, 114, 116 and 123) and 48 h (108, 109, 110 and 111). The covalently modified DNA was separated from unbound agent by EtOH precipitation and resuspended in TE buffer (10 μL). The solution of DNA in an Eppendorf tube sealed with Teflon tape was warmed at 100° C. for 30 min to induce cleavage at the alkylation sites, allowed to cool to 25° C. and centrifuged. Formamide dye (0.03% xylene cyanol FF, 0.03% bromophenol blue, 8.7% Na$_2$EDTA 250 nM) was added (5 μL) to the DNA solution. Prior to electrophoresis, the sample was denatured by warming at 100° C. for 5 min, placed in an ice bath, and centrifuged, and the solution (4 μL) was loaded onto the gel. Sanger dideoxynucleotide sequencing reactions were run as standards adjacent to the reaction samples. Polyacrylamide gel electrophoresis (PAGE) was run on an 8% sequencing gel under denaturing conditions (8 M urea) in TBE buffer (10 mM Tris, 100 mM boric acid, 0.2 mM Na$_2$EDTA) followed by autoradiography.

DNA Alkylation of Calf Thymus DNA. An aliquot of agent (5 μL, 0.01 M in DMSO) was added to a calf thymus DNA solution (0.45 mL, 3.79 mg/mL, 10 mM sodium phosphate, pH 7.0, base-pair:agent=51:1). The DNA-agent mixtures were incubated at 37° C. for 72 h for both enantiomers of 105, 106 and 107 or at 37° C. for 48 h for 108, 109, 110 and 111. For both enantiomers of 105, 106, 108 and 110, the unreacted materials were extracted with EtOAc (0.5 mL×4). The combined extracts were dried and dissolved in EtOAc (0.9 mL) and the quantities of 105, 106, 108, and 110 were determined by UV. Additional extraction with EtOAc (0.5 mL×4) was carried out, and the amounts of combined material were determined by UV. No additional material was recovered. For the ionic agents 107, 109 and 111, the unreacted materials were recovered from the supernatants of EtOH precipitation of the DNA. The EtOH in the supernatant was removed by a stream of N$_2$. The supernatants were diluted to 0.9 mL with H$_2$O and the recovered quantities of 107, 109, and 111 were determined by UV.

These studies were conducted alongside control reactions conducted in the absence of DNA. An aliquot of agent (5 μL, 0.01 M in DMSO) was added to sodium phosphate buffer (0.45 mL, 10 mM, pH 7.0). The agent-buffer mixtures were incubated at 37° C. for 72 h for both enantiomers of 105, 106 and 107 or at 37° C. for 48 h for 108, 109, 110 and 111. For 105, 106, 108 and 110, the materials were extracted with EtOAc (0.5 mL×4). The combined extracts were dried and dissolved in EtOAc (0.9 mL) and the agent quantities were determined by UV. For the ionic agents 107, 109 and 111, the agent-buffer mixtures were diluted to 0.9 mL with H$_2$O and their quantities were determined by UV.

3-[N-(tert-Butyloxycarbonyl)-N-(3-methyl-2-buten-1-yl)]amino-1-benzyloxynaphthalene (205). A suspension of NaH (0.53 g, 22.0 mmol) in anhydrous DMF (10 mL) at 25° C. under Ar was treated with a solution of 204 (5.98 g, 17.0 mmol; Boger, D. L.; Yun, W.; Teegarden, B. R. J. Org. Chem. 1992, 57, 2873) in DMF (50 mL), and the reaction mixture was stirred at 25° C. for 0.5 h. The mixture was cooled to 0° C., and 4-bromo-2-methyl-2-butene (5.9 mL, 51.0 mmol) was added slowly to the mixture. The mixture was allowed to warm to 25° C. and was stirred for 14 h before being poured into H$_2$O (60 mL). The organic layer was separated and the aqueous layer extracted with EtOAc (3×50 mL). The combined organic solutions were washed with H$_2$O (70 mL), saturated aqueous NaCl (100 mL), dried (MgSO$_4$) and concentrated under reduced pressure. Chromatography (SiO$_2$, 15% EtOAc-hexane) gave 205 (6.91 g, 7.10 g theoretical, 97%) as a white solid: mp 89–90.5° C.; $^1$H NMR (CDCl$_3$, 400 MHz) δ8.25 (d, 1H, J=8.1 Hz, C8-H), 7.71 (d, 1H, J=7.4 Hz, C5-H), 7.45 (m, 7H), 7.22 (br s, 1H, C4-H), 6.77 (br s, 1H, C2-H), 5.30 (m, 1H, C2'-H), 5.20 (s, 2H, CH$_2$Ph), 4.25 (br d, 2H, J=6.6 Hz, C1'-H), 1.67 (s, 3H, CH$_3$), 1.51 (s, 3H, CH$_3$), 1.42 (s, 9H, C(CH$_3$)$_3$); $^{13}$C NMR (CDCl$_3$, 100 MHz) δ154.8, 154.4, 140.5, 136.7, 134.3, 134.1, 128.4, 127.8, 127.2, 127.1, 126.6, 124.8, 123.9, 121.9, 120.9, 116.7, 105.9, 79.9, 70.0, 48.2, 28.2 (3C), 25.3, 17.7; IR (solid film) v$_{max}$ 2974, 1694, 1412, 1163 cm$^{-1}$; FABHRMS (NBA-NaI) m/z 417.2291 (M$^+$, C$_{27}$H$_{31}$NO$_3$ requires 417.2304).

Anal. Calcd for C$_{27}$H$_{31}$NO$_3$: C, 77.67; H, 7.48; N, 3.35. Found: C, 77.30; H, 7.60; N, 3.30.

3-[N-(tert-Butyloxycarbonyl)-N-(formylmethyl)]amino-1-benzyloxynaphthalene (206). A solution of 205 (3.31 g, 7.94 mmol) in 5:1 CH$_2$Cl$_2$—CH$_3$OH (350 mL) at −78° C. was treated with a stream of 3% O$_3$/O$_2$ (160 L/h, 4 min). The reaction mixture was quenched quickly with the addition of 14 mL of Me$_2$S and the resulting mixture was stirred at 25° C. (12 h) before the solvent was removed in vacuo. Chromatography (SiO$_2$, 10–20% EtOAc-hexane gradient elution) yielded 206 (2.55 g, 3.15 g theoretical, 81%) as a white solid: mp 96.0–98.0° C.; $^1$H NMR (CDCl$_3$, 400 MHz) δ9.73 (s, 1H, CHO), 8.27 (dd, 1H, J=1.5, 7.9 Hz, C8-H), 7.71 (dd, 1H, J=1.4, 7.4 Hz, C5-H), 7.43 (m, 7H), 7.23 (br s, 1H, C4-H), 6.85 (br s, 1H, C2-H), 5.22 (s, 2H, CH$_2$Ph), 4.39 (s, 2H, CH$_2$CHO), 1.42 (s, 9H, C(CH$_3$)$_3$); $^{13}$C MM (CDCl$_3$, 100 MHz) δ198.1, 154.8, 140.3, 136.7, 134.1, 128.7, 128.1, 127.43, 127.39, 127.0, 125.4, 124.4, 122.1, 116.5, 105.4, 81.6, 70.3, 60.5, 28.2 (3C); IR (solid film) $v_{max}$ 2976, 1736, 1693, 1368 cm$^{-1}$; FABHRMS (NBA-NaI) m/z 414.1672 (M+Na$^+$, $C_{24}H_{25}NO_4$ requires 414.1681).

Anal. Calcd for $C_{24}H_{25}NO_4$: C, 73.64; H, 6.44; N, 3.58. Found: C, 73.50; H, 6.41; N, 3.67.

3-[N-(tert-Butyloxycarbonyl)-N-(3,3-difluoro-2-hydroxy-3-phenylsulfonyl-1-propyl)]amino-1-benzyloxynaphthalene (207). A solution of 206 (33.1 mg, 0.085 mmol) and PhSO$_2$CF$_2$H (31.0 mg, 0.16 mmol) in anhydrous THF (3.5 mL) and HMPA (0.5 mL) was cooled to −78° C. under Ar. A solution of 1.14 M LiHMDS in THF (200 μL, 0.20 mmol) was added dropwise and the resulting orange solution was allowed to warm to 25° C. and stirred for 4 h. The reaction mixture was poured into saturated aqueous NaCl (10 mL) and extracted with Et$_2$O (3×15 mL). The organic layers were combined, dried (MgSO$_4$), filtered, and concentrated under reduced pressure. Chromatography (SiO$_2$, 10% EtOAc-hexane) afforded recovered 206 (10.0 mg, 30%) and 211 (25.2 mg, 49.4 mg theoretical, 51%; 73% based on recovered 206) as a white foam: mp 45–46.5° C.; $^1$H NMR (CDCl$_3$, 400 MHz) δ8.29 (d, 1H, J=7.8 Hz, C8-H), 7.94 (d, 1H, J=7.5 Hz, C5-H), 7.76 (m, 2H, C-6 and C-7H), 7.47 (m, 10H), 7.18 (br s, 1H, C4-H), 6.72 (br s, 1H, C2-H), 5.25 (d, 1H, J=11.6 Hz, CHHPh), 5.21 (d, 1H, J=11.5 Hz, CHHPh), 4.65 (m, 1H, OH), 4.50 (m, 1H, C2'-H), 4.31 (br t, 1H, J=6.0 Hz, C1'-H), 3.89 (br d, 1H, J=14.0 Hz, C1'-H), 1.36 (s, 9H, C(CH$_3$)$_3$); $^{13}$C NMR (CDCl$_3$, 100 MHz) δ154.9, 139.6, 136.6, 135.3, 134.1, 133.2, 130.7, 129.1, 128.7, 128.6, 128.0, 127.6, 127.3, 127.0, 125.5, 122.6, 122.1, 117.6, 105.6, 81.9, 70.1, 69.4 (t, J=84.0 Hz), 51.0 (d, J=12.0 Hz), 28.2 (3C); $^{19}$F NMR (CDCl$_3$, 376 MHz) δ−112.0 (dd, J=40.0, 240.0 Hz), −116.9 (d, J=240.0 Hz); IR (solid film) $v_{max}$ 3390, 1771, 1367 cm$^{-1}$; FABHRMS (NBA-CsI) m/z 716.0899 (M+Cs, $C_{31}H_{31}F_2NO_6S$ requires 716.0894).

Anal. Calcd for $C_{31}H_{31}F_2O_6S$: C, 63.80; H, 5.35; N, 2.40. Found: C, 63.48; H, 5.11; N. 2.41.

3-[N-(tert-Butyloxycarbonyl)-N-(3,3-difluoro-2-methanesulfonyloxy-3-phenylsulfonyl-1-propyl)]amino-1-benzyloxynaphthalene (208). A solution of 207 (205 mg, 0.35 mmol) in CH$_2$Cl$_2$ (5 mL) was cooled to −30° C. under Ar and treated with Et$_3$N (0.30 mL, 3.5 mmol). After stirring for 5 min, MsCl (98 μL, 0.70 mmol) was added and the reaction mixture stirred for an additional 5 h. The reaction mixture was quenched by addition of saturated aqueous NH$_4$Cl (10 mL). The organic layer was removed and the aqueous layer was extracted with EtOAc (3×15 mL). The organic solutions were combined, dried (MgSO$_4$), filtered and concentrated under reduced pressure. Chromatography (SiO$_2$, 10% EtOAc-hexane) yielded 208 (202 mg, 232 mg theoretical, 87%) as a beige foam: mp 54.5–56.0° C; $^1$H NMR (CDCl$_3$, 400 MHz) δ8.28 (dd, 1H, J=1.2, 7.1 Hz, C8-H), 7.90 (d, 1H, J=7.7 Hz, C5-H), 7.75 (m, 2H, C6 and C7-H), 7.32–7.58 (m, 11 H), 7.00 (d, 1H, J=1.4 Hz, C2-H), 5.76 (br m, 1H, C2'-H), 5.24 (s, 2H, CH$_2$Ph), 4.44 (m, 1H, C1'-H), 4.28 (m, 1H, C1'-H), 3.04 (s, 3H, CH$_3$SO$_2$), 1.42 (s, 9H, C(CH$_3$)$_3$); $^{13}$C NMR (CDCl, 100 MHz) δ154.6, 154.3, 140.1, 137.0, 135.9, 134.1, 132.0, 130.8, 129.4, 128.5, 127.9, 127.5, 126.8, 125.3, 124.0, 122.1, 119.2, 117.0, 116.3, 106.5, 81.7, 74.6 (t, J=86.4 Hz), 70.2, 60.3, 50.1, (d, J=15.0 Hz), 39.0, 28.2 (3C), 21.0, 14.1; $^{19}$F NMR (CDCl$_3$, 376 MHz) δ−106.7 (d, J=240.0 Hz), −110.8 (br d, J=240.0 Hz); IR (solid film) $v_{max}$ 1699, 1368, 1160 cm$^{-1}$; FABHRMS (NBA-CsI) m/z 794.0678 (M+Cs$^+$, $C_{32}H_{33}F_2NO_8S_2$ requires 794.0670).

Anal. Calcd for $C_{32}H_{33}F_2NO_8S_2$: C, 58.08; H, 5.03; N, 2.12. Found: C, 58.45; H, 5.16; N, 2.02.

3-[N-(tert-Butyloxycarbonyl)-N-(3,3-difluoro-2-propen-1-yl)]amino-1-benzyloxynaphthalene (209). A solution of 208 (116 mg, 0.17 mmol) in CH$_3$OH (4 mL) cooled to 0° C. under Ar was treated with Na$_2$HPO$_4$ (99 mg, 0.70 mmol) and 5% Na(Hg) (500 mg, 1.1 mmol). After vigorous stirring at 0° C. for 1 h, the reaction mixture was allowed to warm to 25° C. where Et$_2$O (20 mL) was added. The solid Hg residue was removed by filtration through a cotton wool plug and the etheral solution was concentrated under reduced pressure. Chromatography (SiO$_2$, 3% EtOAc-hexane) afforded 209 as a colorless oil (57 mg, 74 mg theoretical, 77%) which crystallized in the refrigerator to give a white solid: mp 57.0–59.0° C.; $^1$H NMR (CDCl$_3$, 400 MHz) δ8.27 (dd, 1H, J=1.0, 8.0 Hz, C8-H), 7.75 (dd, 1H, J=1.2, 8.7 Hz, C5-H), 7.50 (m, 2H, C6 and C7-H), 7.43 (m, 5H, C$_6$H$_5$), 7.21 (s, 1H, C4-H), 6.73 (s, 1H, C2-H), 5.23 (s, 2H, CH$_2$Ph), 4.46 (dtd, 1H, J=1.9, 7.8, 24.2 Hz, C2'-H), 4.49 (dd, 1H, J=1.7, 1.7, C1'-H), 4.27 (dd, 1H, J=1.7, 1.7, C1'-H), 1.43 (s, 9H, C(CH$_3$)$_3$); $^{13}$C NMR (CDCl$_3$, 100 MHz) δ160.0, 157.1, 154.8, 154.4, 154.2, 139.8, 136.8, 134.2, 128.6, 128.0, 127.5, 127.4, 126.9, 125.3, 124.4, 122.1, 117.1, 105.7, 80.8, 76.0 (dd, J=86.8, 87.2 Hz), 70.3, 43.7 (d, J=28.0 Hz), 28.2 (3C); $^{19}$F NMR (CDCl$_3$, 376 MHz) δ−87.6 (d, J=44.0 Hz), −89.0 (dd, J=24.2, 44.0 Hz); IR (film) $v_{max}$ 1746, 1703, 1581 cm$^{-1}$; FABHRMS (NBA-NaI) m/z 425.1815 (M$^+$, $C_{25}H_{25}F_2NO_3$ requires 425.1803).

Anal. Calcd for $C_{25}H_{25}F_2NO_3$: C, 70.57; H, 5.92; N, 3.29. Found: C, 70.82; H, 5.88; N, 3.05.

3-[N-(3,3-Difluoro-2-propen-1-yl)]amino-1-benzyloxynapthalene (210). A solution of 209 (700 mg, 1.64 mmol) in EtSH (4.0 mL) under Ar was treated with BF$_3$.Et$_2$O (305 μL, 2.45 mmol) and the resulting solution was stirred at 25° C. for 1 h before being quenched by the addition of H$_2$O (5 mL). The aqueous layer was extracted with Et$_2$O (3×5 mL) and the combined organic solutions were washed with saturated aqueous NaCl (15 mL), dried (MgSO$_4$), filtered and concentrated under reduced pressure. Chromatography (SiO$_2$, 5% EtOAc-hexane) gave 210 (480 mg, 530 mg theoretical, 91%) as a rust colored viscous oil: $^1$H NMR (CDCl$_3$, 400 MHz) δ8.13 (dd, 1H, J=0.5, 8.4 Hz, C8-H), 7.56 (d, 1H, J=8.2 Hz, C5-H), 7.50 (m, 2H, C6 and C7-H), 7.38 (m, 5H, C$_6$H$_5$), 7.19 (ddd, 1H, J=1.2, 4.9, 7.6 Hz, NH), 6.46 (d, 1H, J=1.8 Hz, C4-H), 6.28 (d, 1H, J=1.9 Hz, C2-H), 5.18 (br s, 2H, CH$_2$Ph), 4.47 (dtd, 1H, J=2.0, 7.7, 24.7 Hz, C2'-H), 3.86 (dd, 1H, J=1.8, 1.8 Hz, C1'-H), 3.84 (dd, 1H, J=1.8, 1.8 Hz, C1'-H); $^{13}$C NMR (CDCl$_3$, 100 MHz) δ159.7, 156.8, 155.2, 153.9, 145.2, 136.8, 135.8, 128.3, 127.8, 127.1, 126.9, 125.6, 121.9, 121.4, 120.4, 97.8, 97.5, 76.7 (t, J=78.0 Hz), 69.6, 36.6 (d, J=24.0 Hz); $^{19}$F NMR (CDCl$_3$, 376 MHz) δ−87.2 (d, J=44.0 Hz), −88.9 (dd, J=24.7, 44.0 Hz); IR (film) $v_{max}$ 3406, 2922, 2852, 1741, 1629 cm$^{-1}$; FABHRMS (NBA) m/z 325.1268 (M$^+$, $C_{20}H_{17}F_2NO$ requires 325.1278).

3-[N-(3,3-Difluoro-2-propen-1-yl)acetamido]-1-benzyloxynaphthalene (211). A solution of 210 (149 mg, 0.46 mmol) in dioxane (5 mL) under Ar was treated with DMAP (50 mg, 0.40 mmol), pyridine (0.37 mL, 4.6 mmol) and Ac$_2$O (0.2 mL, 2.3 mmol) and stirred at 25° C. for 19 h. The reaction solution was quenched by the addition of 10% aqueous HCl (10 mL) and EtoAc (10 mL). The aqueous layer was removed and extracted with EtOAc (3×5 mL). The organic solutions were combined, washed with saturated aqueous NaCl (15 mL), dried (MgSO$_4$), and concentrated under reduced pressure. Chromatography (SiO$_2$, 15% EtOAc-hexane) afforded 211 (162 mg, 169 mg theoretical, 96%) as a pale yellow oil: $^1$H NMR (CDCl$_3$, 400 MHz) δ8.33 (dd, 1H, J=1.6, 8.1 Hz, C8-H), 7.77 (dd, 1H, J=1.7, 7.5 Hz, C5-H), 7.52 (m, 5H, C$_6$H$_5$), 7.38 (m, 2H, C6 and C7-H), 7.20 (d, 1H, J=1.6 Hz, C4-H), 6.57 (d, 1H, J=1.6 Hz, C2-H), 5.25 (s, 2H, CH$_2$Ph), 4.43 (dtd, 1H, J=1.9, 7.9, 24.8 Hz, C2'-H), 4.32 (dd, 1H, J=1.6, 1.6 Hz, C1'-H), 4.30 (m, 1H, C1'-H), 1.82 (s, 3H, CH$_3$CO); $^{13}$C NMR (CDCl$_3$, 100 MHz) δ170.0, 160.0, 157.1, 155.1, 139.4, 135.9, 133.8, 128.2, 127.7, 127.2, 127.1, 126.9, 125.7, 124.7, 121.9, 118.6, 105.0, 74.9 (dd, J=75.2, 91.6 Hz), 69.8, 41.8 (d, J=28 Hz), 22.0; $^{19}$F NMR (CDCl$_3$, 376 MHz) δ−87.0 (d, J=40.0 Hz), −89.1 (dd, J=24.8, 40.0 Hz); IR (film) ν$_{max}$ 2928, 1745, 1660, 1413 cm$^{-1}$; FABHRMS (NBA-NaI) m/z 368.1740 (M+H$^+$, C$_{22}$H$_{19}$F$_2$NO requires 368.1470).

2-[N-(3,3-Difluoro-2-propen-1-yl)acetamido]-4-benzyloxy-1-nitronaphthalene (212). A mixture of 211 (581 mg, 1.58 mmol) and Bu$_4$NNO$_3$ (1.20 g, 3.90 mmol) in CH$_2$Cl$_2$ (20 mL) under Ar was treated with TFAA (0.25 mL). After stirring at 25° C. for 16 h, additional TFAA (10 μL) was added and the reaction mixture was stirred at 25° C. for an additional 4 h. The solution was quenched by the addition of saturated aqueous NaHCO$_3$ (20 mL) and CHCl$_3$ (10 mL). The organic layer was removed and the aqueous layer extracted with CHCl$_3$ (3×15 mL). The combined organic solutions were dried (MgSO$_4$), filtered and concentrated under pressure. Chromatography (SiO$_2$, 10% EtOAc-hexane) gave 212 (457 mg, 652 mg theoretical, 70%) as a yellow oil: $^1$H NMR (CDCl$_3$, 400 MHz) δ8.42 (d, 1H, J=8.0 Hz, C8-H), 7.79 (d, 1H, J=8.2 Hz, C5-H), 7.71 (dt, 1H, J=1.3, 6.9 Hz, C6 or C7-H), 7.65 (dt, 1H, J=1.3, 6.9 Hz, C7 or C6-H), 7.42 (m, 5H, C$_6$H$_5$), 6.55 (s, 1H, C3-H), 5.32 (d, 1H, J=16.7 Hz, CHHPh), 5.29 (d, 1H, J=16.7 Hz, CHHPh), 4.43 (m, 2H, C1'-H), 4.05 (m, 1H, C2'-H), 1.83 (s, 3H, CH$_3$CO); $^{13}$C NMR (CDCl$_3$, 100 MHz) δ170.0, 160.4, 157.5, 156.8, 154.6, 140.0, 135.0, 132.4, 129.8, 128.7, 128.4, 127.6, 127.1, 125.7, 125.2, 122.6, 121.9, 105.0, 74.5 (dd, J=72.4, 93.6 Hz), 70.9, 42.1 (d, J=29.6 Hz), 22.0; $^{19}$F NMR (CDCl$_3$, 376 MHz) δ−85.6 (d, J=36.0 Hz), −88.5 (dd, J=28.0, 36.0 Hz); IR (film) ν$_{max}$ 2928, 1746, 1674, 1525 cm ; FABHRMS (NBA) m/z 413.1319 (M+H, C$_{22}$H$_{18}$F$_2$N$_2$O$_4$ requires 413.1313). The regiochemistry of the nitration was confirmed by $^1$H NMR employing 1D-NOE, 2D-NOE and HMBC experiments. Carbon-carbon connectivity from the HMBC study showed connectivity of the NO$_2$ bearing carbon (δ157.5) to the C2 (δ132.6) and the C8a carbon (δ125.8). This was further supported by $^1$H NMR NOE experiments where irradiation of the C3-H resonance (δ6.55) resulted in a 5% enhancement of the OCH$_2$Ph resonance at δ5.30 and a 4% enhancement of the CH$_3$CO resonance at δ1.83. Similarly, the 2D-NOE experiment showed diagnostic crosspeaks of C3-H with OCH$_2$Ph and CH$_3$CO.

Occasionally, the isomeric nitration product, 3-[N-(3,3-difluoro-2-propen-2-yl)acetamido]-1-benzyloxy-2-nitronaphthalene (ca. 10%), could be isolated: $^1$H NMR (CDCl$_3$, 400 MHz) δ8.21 (dd, 1H, J=2.3, 7.8 Hz, C8-H), 7.91 (dd, 1H, J=2.1, 6.8 Hz, C5-H), 7.70 (m, 2H, C6 and C7-H), 7.53 (s, 1H, C4-H), 5.03 (m, 5H, C$_6$H$_5$), 5.28 (d, 1H, J=13.9 Hz, CHHPh), 5.25 (d, 1H, J=13.9 Hz, CHHPh), 4.55 (m, 2H, C2'-H and C1'-H), 3.94 (m, 1H, C1'-H), 1.91 (s, 3H, CH$_3$CO); $^{13}$C NMR (CDCl, 100 MHz) δ170.6, 160.8, 157.9, 155.0, 148.4, 140.7, 135.4, 133.9, 131.1, 129.6, 129.0, 128.9, 128.8, 128.7, 128.6, 128.3, 125.6, 123.6, 78.8, 74.6 (dd, J=92.8, 93.2 Hz), 42.4 (d, J=30.0 Hz), 22.4; $^{19}$F NMR (CDCl$_3$, 376 MHz) −85.9 (d, J=40.0 Hz), −88.8 (dd, J=28.0, 40.0 Hz); IR (film) ν$_{max}$ 3066, 2888, 1746, 1681, 1538 cm$^{-1}$; FABHRMS (NBA-NaI) m/z 413.1357 (M+H, C$_{22}$H$_{18}$F$_2$N$_2$O$_4$ requires 413.1313).

For 3-[N-(tert-butyloxycarbonyl)-N-(3,3-difluoro-2-methanesulfonyloxy-1-propyl)]amino-1-benzyloxynaphthalene: $^1$H NMR (CDCl$_3$, 400 MHz) δ8.27 (dd, 1H, J=1.3, 7.6 Hz, C8-H), 7.75 (dd, 1H, J=1.4, 7.5 Hz, C5-H), 7.45 (m, 7H), 7.25 (d, 1H, J=1.3 Hz, C4-H), 6.84 (d, 1H, J=1.5 Hz, C2-H), 5.87 (dt, 1H, J=2.9, 54.1 Hz, CF$_2$H), 5.25 (s, 2H, OCH$_2$Ph), 5.18 (m, 1H, C2'-H), 4.15 (dd, 1H, J=14.9, 14.9 Hz, C1'-H), 3.97 (dd, 1H, J=14.9, 14.9 Hz, C1'-H), 2.99 (s, 3H, CH$_3$SO$_2$), 1.39 (s, 9H, C(CH$_3$)$_3$); IR (film) ν$_{max}$ 3418, 2962, 1703, 1581, 1260 cm$^{-1}$; FABHRMS (NBA-NaI) m/z (M$^+$, C$_{26}$H$_{29}$F$_2$NO$_6$S requires 521.1684).

For 3-[N-tert-butyloxycarbonyl)-N-(3,3-difluoro-3-phenylsulfonyl-2-tosyloxy-1-propyl)]amino-1-benzyloxynaphthalene: $^1$H NMR (CDCl$_3$, 250 MHz) δ8.23 (d, 1H, J=7.5 Hz, C8-H), 7.76 (d, 1H, J=7.6 Hz, C5-H), 7.60–7.68 (m, 6H), 7.28–7.47 (m, 10H), 7.12 (br s, 1H, C4-H), 6.97 (br s, 1H, C2-H), 5.76 (m, 1H, C2'-H), 5.18 (s, 2H, CH$_2$Ph), 4.52 (m, 1H, C1-H), 4.13 (m, 1H, C1'-H), 2.53 (s, 3H, CH$_3$), 1.45 (s, 9H, C(CH$_3$)$_3$).

For 3[N-(tert)-butyloxycarbonyl)-N-(3,3-difluoro-2-hydroxy-1-propyl)]amino-1-benzyloxynaphthalene: $^1$H NMR (CDCl$_3$, 400 MHz) δ8.30 (dd, 1H, J=2.0, 7.6 Hz, C8-H), 7.74 (dd, 1H, J=2.0, 7.4 Hz, C5-H), 7.51 (m, 2H, C6 and C7-H), 7.40 (m, 6H), 6.70 (s, 1H, C2-H), 5.70 (dt, 1H, J=3.3, 55.4 Hz, CF$_2$H), 5.24 (s, 2H, OCH$_2$Ph), 5.11 (br s, 1H, OH), 4.11 (m, 1H, C2'-H), 3.98 (m, 1H, C1'-H), 3.74 (d, 1H, J=15.0 Hz, C1'-H), 1.37 (s, 9H, C(CH$_3$)$_3$); IR (film) ν$_{max}$ 3430, 2924, 1693, 1367 cm$^{-1}$; FABHRMS (NBA-NaI) m/z 443.1895 (M$^+$, C$_{25}$H$_{27}$F$_2$NO$_4$ requires 443.1980).

For 3-(5-difluoromethyl-oxazolidinon-3-yl)-1-benzyloxynaphthalene: $^1$H NMR (CDCl$_3$, 400 MHz) δ8.26 (d, 1H, J=8.2 Hz, C8-H), 7.76 (d, 1H, J=2.0 Hz, C4-H), 7.71 (d, 1H, J=8.0 Hz, C5-H), 7.33–7.56 (m, 7H), 7.05 (d, 1H, J=1.9 Hz, C2-H), 5.28 (s, 2H, CH$_2$Ph), 4.82 (m, 1H, C5'-H), 4.23 (m, 2H, C4'-H); IR (film) ν$_{max}$ 2924, 1764, 1417 cm$^{-1}$; FABHRMS (NBA-NaI) m/z 369.1104 (M$^+$, C$_{21}$H$_{17}$F$_2$NO$_3$ requires 369.1176).

For 220a: $^1$H NMR (CDCl$_3$, 400 MHz) δ8.58 (d, 1H, J=8.2 Hz, C9-H), 8.00 (d, 1H, J=8.4 Hz, C6-H), 7.64 (dt, 1H, J=1.1, 7.6 Hz, C7-H), 7.52 (dt, 1H, J=1.2, 7.6 Hz, C8-H), 7.37 (s, 1H, C4-H), 4.78 (dd, 1H, J=1.7, 7.6 Hz, C1'-H), 4.77 (dd, 1H, J=1.7, 7.6 Hz, C1'-H), 4.51 (dtd, 1H, J=1.2, 7.4, 24.0 Hz, C2'-H), 4.38 (q, 2H, J=7.2 Hz, CH$_2$CH$_3$), 2.69 (s, 3H, CH$_3$), 1.44 (t, 3H, J=7.2 Hz, CH$_2$CH$_3$); $^{13}$C NMR (CDCl$_3$, 100 MHz) δ160.3, 157.4, 154.5, 154.1, 136.01 129.2, 127.2, 126.8, 125.0, 123.5, 121.9, 121.7, 102.3, 75.1 (dd, J=24.2, 24.2 Hz), 65.1, 37.2 (d, J=7.1 Hz), 14.3, 13.8; $^{19}$F NMR (CDCl$_3$, 376 MHz) δ−85.1 (d, J=36.0 Hz), −86.1 (dd, J=24.0, 36.0 Hz); IR (film) ν$_{max}$ 2929, 1748, 1233 cm$^{-1}$; FABHRMS (NBA-NaI) m/z 347.1198 (M+$^+$H, C$_{18}$H$_{16}$F$_2$N$_2$O$_3$ requires 347.1207).

For 220b: $^1$H NMR (CDCl$_3$, 400 MHz) δ8.59 (d, 1H, J=8.2 Hz, C9-H), 7.97 (d, 1H, J=8.3 Hz, C6-H), 7.63 (t, 1H, J=7.0 Hz, C7-H), 7.51 (t, 1H, J=7.3 Hz, C8-H), 7.34 (s, 1H, C4-H), 4.80 (m, 2H, C1'-H$_2$), 4.52 (m, 1H, C2'-H), 2.65 (s, 3H, CH$_3$), 1.56 (s, 9H, C(CH$_3$)$_3$).

For 221: $^1$H NMR (CDCl$_3$, 400 MHz) δ8.19 (dd, 1H, J=2.2, 7.0 Hz, C8-H), 7.71–7.81 (m, 3H), 7.27 (s, 1H, C3-H), 4.53 (m, 2H, C1'-H and C2'-H), 4.05 (m, 1H, C1'-H), 1.92 (s, 3H, CH$_3$CO), 1.61 (s, 9H, C(CH$_3$)$_3$).

For 1-amino-4-[(tert-butyloxycarbonyl)oxy]-2-[N-(3,3-difluoro-2-propen-1-yl)acetamido]naphthalene (222): $^1$H NMR (CDCl$_3$, 400 MHz) δ7.96 (dd, 1H, J=1.8, 6.5 Hz, C5-H), 7.83 (dd, 1H, J=2.0, 6.6 Hz, C8-H), 7.57 (m, 2H, C6 and C7-H), 6.98 (s, 1H, C3-H), 4.48 (m, 2H, C1'-H and C2'-H), 4.15 (m, 1H, C1'-H), 4.31 (br s, 2H, NH$_2$), 1.89 (s, 3H, CH₃CO), 1.57 (s, 9H, C(C₃H₃)); ¹⁹F NMR (CDCl₃, 376 MHz) δ −86.2 (d, J=40.0 Hz), −88.2 (dd, J=24.0, 40.0 Hz); IR (film) $v_{max}$ 3360, 1747, 1250 cm⁻¹; FABHRMS (NBA-NaI) m/z 415.1445 (M+Na⁺, C₂₀H₂₂F₂N₂O₄ requires 415.1455).

DNA Alkylation Studies: Selectivity and Efficiency. Eppendorf tubes containing singly ³²P 5'-end-labeled w794 DNA[58] (9 μL) in TE buffer (10 mM Tris, 1 mM EDTA, pH 7.5) were treated with agents in DMSO (1 μL, at the specified concentrations). The solutions were mixed by vortexing and brief centrifugation and subsequently incubated at 25 or 4° C. for 72 h. The modified DNA was separated from unbound agent by EtOH precipitation of the DNA. The EtOH precipitations were carried out by adding t-RNA as a carrier (1 μL, 10 μg/μL), 3 M NaOAc (0.1 volume) and −20° C. EtOH (2.5 volumes). The solutions were mixed and chilled at −78° C. in a REVCO freezer for 1 h or longer. The DNA was reduced to a pellet by centrifugation at 4° C. for 15 min and washed with −20° C. 70% EtOH in TE buffer containing 0.2 M NaCl. The pellets were dried on a Savant Speed Vac concentrator and resuspended in TE buffer (10 μL). The solutions of alkylated DNA were warmed at 100° C. for 30 min to induce cleavage at the adenine N3 alkylation sites. After brief centrifugation, formamide dye solution (5 μL) was added. Prior to electrophoresis, the samples were denatured by warming at 100° C. for 5 min, placed in an ice bath, centrifuged briefly, and the supernatant (2.8 μL) was loaded onto a gel. Sanger dideoxynucleotide sequencing reactions were run as standards adjacent to the agent treated DNA reaction samples. Polyacrylamide gel electrophoresis (PAGE) was run on an 8% sequencing gel under denaturing conditions (19:1 acrylamide: N,N'-methylenebisacrylamide, 8 M urea) in TBE buffer (100 mM Tris, 100 mM boric acid, 0.2 mM Na₂EDTA). PAGE was pre-run for 30 min with formamide dye solution prior to loading the samples. Autoradiography of dried gels were carried out at −78° C. using Kodak X-Omat AR film and a Picker Spectra™ intensifying screen.

Synthesis of Compound 309

A solution of 308 (2.5 mg, 7.0 μmol; Boger et al. *J. Am. Chem. Soc.* 1992 114, 10056) in 4 M HCl-EtOAc (400 μL) was stirred at 25° C. under Ar for 30 min. The solvent was removed under a stream of N₂. After being dried in vacuo, the residue was dissolved in THF (200 μL) and treated with 200 μL of 5% aqueous NaHCO₃. The reaction mixture was stirred at 25° C. for 5 h before the solvent was removed in vacuo. PTLC (SiO₂, 0.25 mm×20×20 cm, 70% THF-hexane) afforded 309 (1.6 mg, 1.6 mg theoretical, 100%) as a cream colored solid:

Synthesis of Compounds 314, 315, 316, or 317

After being dried in vacuo, the residue, 39 (1.0 mg, 4.2 μmol, 1 equiv; vida supra), EDCI (2.9 mg, 12.6 μmol, 3 equiv; Aldrich) and either 310, 311, 312 or 313 (1.1 equiv; Aldrich) were dissolved into anhydrous DMF and the reaction mixture was stirred at 25° C. for 16 h. The solvent was removed under vacuum and the residue was dissolved in THF and loaded directly onto a silica gel column. Chromatography (SiO₂, 0.5×6 cm, 50% EtOAc-hexane) afforded 314, 315, 316, or 317 (1.7 mg, 2.0 mg theoretical, 85%) as a mustard colored solid.

Synthesis of Compounds 304, 305, 306 or 307

A solution of 314, 315, 316, or 317 (1.4 mg, 3.91 μmol) in 2:1 DMF-THF (112 μL) at 0° C. was treated with NaH (1.6 mg, 39 μmol, 60% oil dispersion) and the mixture was stirred for 30 min. The solvent was removed under a stream of N₂ and vacuum. PTLC (SiO₂, 0.25 mm×10×15 cm, 30% EtOAc-hexane) afforded 304, 305, 306 or 307.

What is claimed:

1. A compound represented by the following structure:

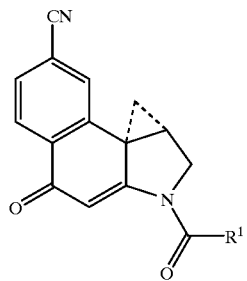

wherein

R₁ is selected from the group consisting of alkyl (C1–C6) and a radical represented by the following structure:

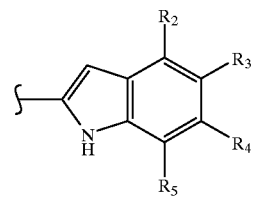

wherein

R₂ and R₃, together with the carbon atoms of the depicted vinylene group, form a group W that is an N-substituted pyrrolidine ring containing the vinylene group with the proviso that R₄ and R₅ are hydrogen, or R₂ is hydrogen and R₃ is an N-substituted subgroup represented by the following compound:

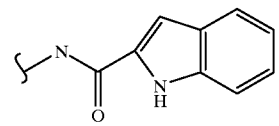

with the proviso that R₄ and R₅ are hydrogen, or

R₂ is hydrogen; R₃ is selected from the group consisting of hydrogen and OCH₃; R₄ is selected from the group consisting of hydrogen and OCH₃; and R₅ is selected from the group consisting of hydrogen and OCH₃.

2. A compound as described in claim 1 wherein the N-substituted pyrrolidine ring is represented by the following structure:

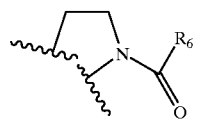

wherein

R₂ is C-linked and R₃ is N-linked to form the depicted pyroline ring;

R₆ is selected from the group consisting of NH₂ and the compound represented by the following structure:

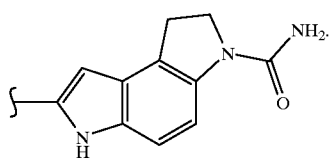

3. A compound represented by the following structure:

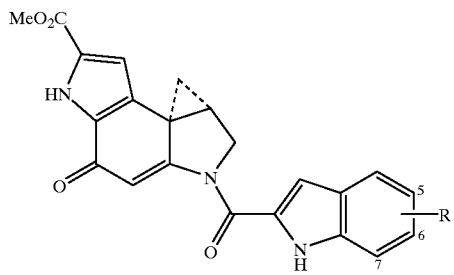

wherein R is selected from the group consisting of H and —OMe.

4. A compound represented by the following structure:

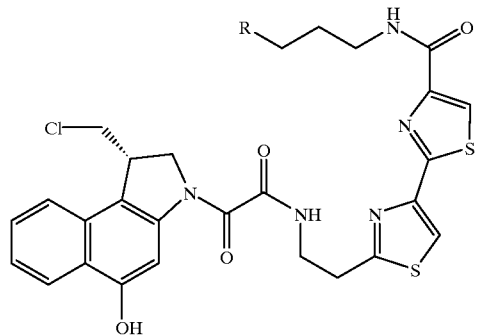

wherein R is selected from the group consisting of —SMe, —S(O)Me, and —⁺SMe₂.

5. A compound represented by the following structure:

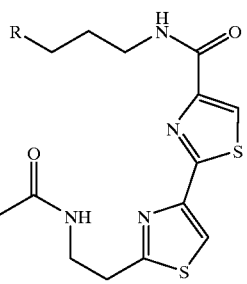

wherein R is selected from the group consisting of —SMe and —⁺Sme₂.

6. A compound represented by the following structure:

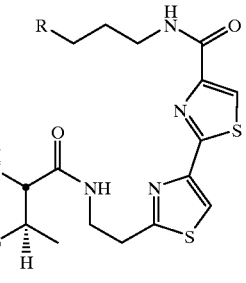

wherein R is selected from the group consisting of —SMe and —⁺Sme₂.

7. A compound represented by the following structure:

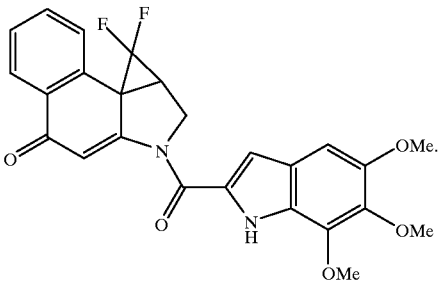

* * * * *

UNITED STATES PATENT AND TRADEMARK OFFICE
CERTIFICATE OF CORRECTION

PATENT NO : 6,060,608
DATED : May 9, 2000
INVENTOR(S) : Boger

It is certified that error appears in the above-identified patent and that said Letters Patent are hereby corrected as shown below:

In Column 1, line 8, please insert:

--This invention was made with government support under Contract Nos. CA41986 and CA55276 by the National Institutes of Health. The government has certain rights in the invention.--

Signed and Sealed this

Seventeenth Day of April, 2001

Attest:

NICHOLAS P. GODICI

Attesting Officer

Acting Director of the United States Patent and Trademark Office